United States Patent
Schreiter et al.

(10) Patent No.: US 11,385,236 B2
(45) Date of Patent: Jul. 12, 2022

(54) CHEMIGENETIC VOLTAGE INDICATORS

(71) Applicant: HOWARD HUGHES MEDICAL INSTITUTE, Chevy Chase, MD (US)

(72) Inventors: Eric R. Schreiter, Ashburn, VA (US); Luke D. Lavis, Leesburg, VA (US); Ahmed Abdelfattah, Ashburn, VA (US)

(73) Assignee: HOWARD HUGHES MEDICAL INSTITUTE, Chevy Chase, MD (US)

(*) Notice: Subject to any disclaimer, the term of this patent is extended or adjusted under 35 U.S.C. 154(b) by 527 days.

(21) Appl. No.: 16/347,765

(22) PCT Filed: Nov. 30, 2017

(86) PCT No.: PCT/US2017/063998
§ 371 (c)(1),
(2) Date: May 6, 2019

(87) PCT Pub. No.: WO2018/102577
PCT Pub. Date: Jun. 7, 2018

(65) Prior Publication Data
US 2020/0025769 A1    Jan. 23, 2020

Related U.S. Application Data

(60) Provisional application No. 62/428,066, filed on Nov. 30, 2016.

(51) Int. Cl.
| | |
|---|---|
| *G01N 33/58* | (2006.01) |
| *C07K 14/195* | (2006.01) |
| *C07K 14/215* | (2006.01) |
| *C07K 14/435* | (2006.01) |
| *C07K 14/46* | (2006.01) |
| *C07K 14/465* | (2006.01) |
| *C12N 9/14* | (2006.01) |
| *G01N 21/64* | (2006.01) |
| *G01N 33/566* | (2006.01) |

(52) U.S. Cl.
CPC ......... *G01N 33/582* (2013.01); *C07K 14/195* (2013.01); *C07K 14/215* (2013.01); *C07K 14/43504* (2013.01); *C07K 14/461* (2013.01); *C07K 14/465* (2013.01); *C12N 9/14* (2013.01); *C12Y 308/01005* (2013.01); *G01N 21/6428* (2013.01); *G01N 33/566* (2013.01); *C07K 2319/60* (2013.01); *G01N 2021/6439* (2013.01)

(58) Field of Classification Search
CPC ............. G01N 33/566; G01N 33/582; G01N 2021/6439; G01N 21/6428; G01N 2333/726; G01N 21/64; C07K 14/195; C07K 14/215; C07K 14/405; C07K 14/43504; C07K 14/461; C07K 14/465; C07K 14/47; C07K 2319/00; C07K 2319/60; C12N 9/14; C12Y 308/01005
See application file for complete search history.

(56) References Cited

U.S. PATENT DOCUMENTS

| | | | | |
|---|---|---|---|---|
| 2015/0182679 A1* | 7/2015 | Parker | ................ | A61F 2/2415 623/2.13 |
| 2015/0301029 A1 | 10/2015 | Eggan et al. | | |

OTHER PUBLICATIONS

Peterka et al. Neuron. (2011) 69(1): 9-21 (Year: 2011).*
Hinner et al. Current Opinions Biotechnol. (2010) 21: 766-776 (Year: 2010).*
Park et al. Process Biochem. (2014) 49: 1516-1526 (Year: 2014).*
New England Biolabs product data sheet for SNAP-Surface(R) Alexa Fluor(R) 488 downloaded from https://www.neb.sg/products/s9129-snap-surface-alexa-fluor-488#Product%20Information on Mar. 9, 2022 (Year: 2022).*
Han et al. PLOS ONE (2013) 8(11): e81295, 9 pages (Year: 2013).*
Lin, M.Z., et al. Genetically encoded indicators of neuronal activity. Nat. Neurosci. 19, 1142-1153, doi:10.1038/nn.4359 (2016).
Grimm, J.B., et al. A general method to improve fluorophores for live-cell and single-molecule microscopy. Nat. Methods 12, 244-250, 243 p following 250, doi:10.1038/nmeth.3256 (2015).
Hochbaum, D.R., et al. All-optical electrophysiology in mammalian neurons using engineered microbial rhodopsins. Nat. Methods 11, 825-833, doi:10.1038/nmeth.3000 (2014).
Gong, Y., et al. High-speed recording of neural spikes in awake mice and flies with a fluorescent voltage sensor. Science (80-.). 350, 1361-1366 (2015).
Los, G.V., et al. HaloTag: A novel protein labeling technology for cell imaging and protein analysis. ACS Chem. Biol. 3, 373-382 (2008).
Encell, L.P., et al. Development of a dehalogenase-based protein fusion tag capable of rapid, selective and covalent attachment to customizable ligands. Curr. Chem. Genomics 6, 55-71 (2012).
Keppler, A., et al. A general method for the covalent labeling of fusion proteins with small molecules in vivo. Nat. Biotechnol. 21, 86-89 (2002).

(Continued)

*Primary Examiner* — Susan M Hanley
(74) *Attorney, Agent, or Firm* — Stites & Harbison, PLLC; Mandy Wilson Decker; Samuel A. Raque

(57) ABSTRACT

Provided herein are a voltage indicator and a method of measuring voltage. The voltage indicator includes a membrane-localized voltage-sensitive protein coupled to a capture protein. The method of measuring voltage includes administering a voltage indicator including a membrane-localized voltage-sensitive protein coupled to a capture protein, and determining changes in fluorescence of a small-molecule fluorescent dye captured by the capture protein.

20 Claims, 20 Drawing Sheets

Specification includes a Sequence Listing.

(56) References Cited

OTHER PUBLICATIONS

Grimm, J. B. et al. A general method to fine-tune fluorophores for live-cell and in vivo imaging. Nat. Methods 14, 987 (2017).
Platisa, J., et al. Directed Evolution of Key Residues in Fluorescent Protein Inverses the Polarity of Voltage Sensitivity in the Genetically Encoded Indicator ArcLight. ACS Chem. Neurosci. 8, 513-523 (2017).
Chamberland, S. et al. Fast two-photon imaging of subcellular voltage dynamics in neuronal tissue with genetically encoded indicators. Elife 6, e25690 (2017).
Abdelfattah, A. S. et al. A bright and fast red fluorescent protein voltage indicator that reports neuronal activity in organotypic brain slices. J. Neurosci. 36, 2458-2472 (2016).
Abdelfattah, A.S., et al. Ratiometric and photoconvertible fluorescent protein-based voltage indicator prototypes. Chem. Commun. 104, 40-50 (2016).
Woodford, C.R. et al. Improved PeT molecules for optically sensing voltage in neurons. J. Am. Chem. Soc. 137, 1817-1824(2015).
Grenier, V., et al. A Small-Molecule Photoactivatable Optical Sensor of Transmembrane Potential. J. Am. Chem. Soc. 137, 10894-10897 (2015).
Huang, Y.L., et al. A Photostable Silicon Rhodamine Platform for Optical Voltage Sensing. J. Am. Chem. Soc. 137, 10767-10776(2015).
Zou, P. et al. Bright and fast multicoloured voltage reporters via electrochromic FRET. Nat. Commun. 5, 4625 (2014).
St-Pierre, F. et al. High-fidelity optical reporting of neuronal electrical activity with an ultrafast fluorescent voltage sensor. Nat Neurosci. 17, 884-889 (2014).
Gong, Y., et al. Imaging neural spiking in brain tissue using FRET-opsin protein voltage sensors. Nat. Commun. 5, 3674 (2014).
Treger, J.S., et al. Real-time imaging of electrical signals with an infrared FDA-approved dye. Biophys. J. 107, L09-L012 (2014).
Han, Z. et al. Fluorescent protein voltage probes derived from ArcLight that respond to membrane voltage changes with fast kinetics. PLoS One 8, e81295 (2013).
Gong, Y., et al. Enhanced Archaerhodopsin Fluorescent Protein Voltage Indicators. PLoS One 8, e66959 (2013).
Barnett, L., et al. A fluorescent, genetically-encoded voltage probe capable of resolving action potentials. PLoS One 7, e43454 (2012).
Akemann, W. et al. Imaging neural circuit dynamics with a voltage-sensitive fluorescent protein. J. Neurophysiol. 108, 2323-2337 (2012).
Jin, L. et al. Single action potentials and subthreshold electrical events imaged in neurons with a fluorescent protein voltage probe. Neuron 75, 779-785 (2012).
Yan, P. et al. Palette of fluorinated voltage-sensitive hemicyanine dyes. Proc. Natl. Acad. Sci. 109, 20443-20448 (2012).
Miller, E.W. et al. Optically monitoring voltage in neurons by photo-induced electron transfer through molecular wires. Proc. Natl. Acad. Sci. 109, 2114-2119 (2012).
Kralj, J.M., et al. Electrical spiking in *Escherichia coli* probed with a fluorescent voltage-indicating protein. Science (80-.). 333, 345-348 (2011).
Kralj, J.M., et al. Optical recording of action potentials in mammalian neurons using a microbial rhodopsin. Nat. Methods 9, 90-95 (2011).
Lebeuf, R., et al. Straightforward synthesis of the near-Infrared fluorescent voltagesensitive dye RH1691 and analogues thereof. Org. Lett. 11, 4822-4825 (2009).
Bradley, J., et al. Submillisecond Optical Reporting of Membrane Potential In Situ Using a Neuronal Tracer Dye. J. Neurosci. 29, 9197-9209 (2009).
Gautier, A. et al. An Engineered Protein Tag for Multiprotein Labeling in Living Cells. Chem. Biol. 15, 128-136 (2008).
Fromherz, P., et al. ANNINE-6plus, a voltage-sensitive dye with good solubility, strong membrane binding and high sensitivity. Eur. Biophys. J. 37, 509-514 (2008).
Sjulson, L., et al. Rational Optimization and Imaging In Vivo of a Genetically Encoded Optical Voltage Reporter. J. Neurosci. 28, 5582-5593 (2008).
Knopfel, T., et al. Optical recordings of membrane potential using genetically targeted voltage-sensitive fluorescent proteins. Methods 30, 42-48 (2003).
Guerrero, G., et al. Tuning FlaSh: redesign of the dynamics, voltage range, and color of the genetically encoded optical sensor of membrane potential. Biophys. J. 83, 3607-3618 (2002).
Ataka, K., et al. A genetically targetable fluorescent probe of channel gating with rapid kinetics. Biophys. J. 82, 509-516 (2002).
Siegel, M.S., et al. A genetically encoded optical probe of membrane voltage. Neuron 19, 735-741 (1997).
United States Patent and Trademark Office, International Search Report issued in corresponding Application No. PCT/US2017/063998, dated Feb. 8, 2018.
Bedbrook, C.N., et al. Genetically Encoded Spy Peptide Fusion System to Detect Plasma Membrane-Localized Proteins In Vivo. Chemistry and Biology. Aug. 20, 2015; vol. 22, No. 8; pp. 1108-1121; p. 1114, col. 2, paragraph 1; 01: 10.1016/j.chembiol.2015.06.020.
Grimm, J.B., et al. Bright Photoactivatable Fluorophores for Single-Molecule Imaging. Nature Methods. Oct. 24, 2016; vol. 13, No. 12; pp. 1-19; abstract; p. 10, paragraph 2 ; DOI: 10.1038/nmeth.4034.
Murata, Y., et al. Phosphoinositide Phosphatase Activity Coupled to an Intrinsic Voltage Sensor. May 18, 2005; vol. 435, No. 7046; pp. 1239-1243; abstract; p. 1243, col. 1, paragraph 3; DOI: 10.1038/nature03650.
Jing, C., et al. Chemical Tags for Labeling Proteins Inside Living Cells. Accounts of Chemical Research. Aug. 31, 2011; vol. 44, No. 9; pp. 1-17; p. 3, paragraph 2; DOI: 10.1021/ar200099f.
Yang, H.H., et al. Genetically Encoded Voltage Indicators: Opportunities and Challenges. The Journal of Neuroscience. Sep. 28, 2016; vol. 36, No. 39; pp. 9977-9989; p. 9978, col. 1, paragraph 4; DOI: 10.1523/JNEUROSCI.1095-16.2016.

* cited by examiner

FIG. 15A  FIG. 15B

SEQUENCE LISTING

```
<160> NUMBER OF SEQ ID NOS: 32

<210> SEQ ID NO 1
<211> LENGTH: 1767
<212> TYPE: DNA
<213> ORGANISM: Artificial
<220> FEATURE:
<223> OTHER INFORMATION: QuasAr2-HaloTag Ligand

<400> SEQUENCE: 1
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240 gtcggggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg ccccgaggt ggcatctacc     540
```

```
tttaacacccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgacatggca    780
gaaatcggta ctggctttcc attcgacccc cattatgtgg aagtcctggg cgagcgcatg    840
cactacgtcg atgttggtcc gcgcgatggc accctgtgc tgttcctgca cggtaacccg     900
acctcctcct acgtgtggcg caacatcatc ccgcatgttg caccgaccca tcgctgcatt    960
gctccagacc tgatcggtat gggcaaatcc gacaaaccag acctgggtta tttcttcgac   1020
gaccacgtcc gcttcatgga tgccttcatc gaagccctgg gtctggaaga ggtcgtcctg   1080
gtcattcacg actggggctc cgctctgggt ttccactggg ccaagcgcaa tccagagcgc   1140
gtcaaaggta ttgcatttat ggagttcatc cgccctatcc cgacctggga cgaatggcca   1200
gaatttgccc gcgagacctt ccaggccttc cgcaccaccg acgtcggccg caagctgatc   1260
atcgatcaga acgttttat cgagggtacg ctgccgatgg tgtcgtccg cccgctgact     1320
gaagtcgaga tggaccatta ccgcgagccg ttcctgaatc ctgttgaccg cgagccactg   1380
tggcgcttcc caaacgagct gccaatcgcc ggtgagccag cgaacatcgt cgcgctggtc   1440
gaagaataca tggactggct gcaccagtcc cctgtcccga agctgctgtt ctggggcacc   1500
ccaggcgttc tgatcccacc ggccgaagcc gctcgcctgg ccaaaagcct gcctaactgc   1560
aaggctgtgg acatcggccc gggtctgaat ctgctgcaag aagacaaccc ggacctgatc   1620
ggcagcgaga tcgcgcgctg gctgtcgacg ctcgagattt ccggcgagcc aaccactaag   1680
agtagaatca caagcgaagg cgagtacatc ccctggatc aaatagacat aaatgtaggt    1740
ggatttttgtt atgagaatga agtataa                                      1767
```

<210> SEQ ID NO 2  
<211> LENGTH: 588  
<212> TYPE: PRT  
<213> ORGANISM: Artificial  
<220> FEATURE:  
<223> OTHER INFORMATION: QuasAr2-HaloTag Ligand

<400> SEQUENCE: 2

```
Met Val Ser Ile Ala Leu Gln Ala Gly Tyr Asp Leu Leu Gly Asp Gly
1               5                   10                  15
Arg Pro Glu Thr Leu Trp Leu Gly Ile Gly Thr Leu Leu Met Leu Ile
            20                  25                  30
Gly Thr Phe Tyr Phe Leu Val Arg Gly Trp Gly Val Thr Asp Lys Asp
        35                  40                  45
Ala Arg Glu Tyr Tyr Ala Val Thr Ile Leu Val Ser Gly Ile Ala Ser
    50                  55                  60
Ala Ala Tyr Leu Ser Met Phe Phe Gly Ile Gly Leu Thr Glu Val Ser
65                  70                  75                  80
Val Gly Gly Glu Met Leu Asp Ile Tyr Tyr Ala Arg Tyr Ala Gln Trp
                85                  90                  95
Leu Phe Thr Thr Pro Leu Leu Leu Leu His Leu Ala Leu Leu Ala Lys
            100                 105                 110
Val Asp Arg Val Thr Ile Gly Thr Leu Val Gly Val Asp Ala Leu Met
        115                 120                 125
Ile Val Thr Gly Leu Ile Gly Ala Leu Ser His Thr Ala Ile Ala Arg
    130                 135                 140
```

```
Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
            165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
            245                 250                 255

Ala Asp Met Ala Glu Ile Gly Thr Gly Phe Pro Phe Asp Pro His Tyr
            260                 265                 270

Val Glu Val Leu Gly Glu Arg Met His Tyr Val Asp Val Gly Pro Arg
            275                 280                 285

Asp Gly Thr Pro Val Leu Phe Leu His Gly Asn Pro Thr Ser Ser Tyr
            290                 295                 300

Val Trp Arg Asn Ile Ile Pro His Val Ala Pro Thr His Arg Cys Ile
305                 310                 315                 320

Ala Pro Asp Leu Ile Gly Met Gly Lys Ser Asp Lys Pro Asp Leu Gly
            325                 330                 335

Tyr Phe Phe Asp Asp His Val Arg Phe Met Asp Ala Phe Ile Glu Ala
            340                 345                 350

Leu Gly Leu Glu Glu Val Val Leu Val Ile His Asp Trp Gly Ser Ala
            355                 360                 365

Leu Gly Phe His Trp Ala Lys Arg Asn Pro Glu Arg Val Lys Gly Ile
            370                 375                 380

Ala Phe Met Glu Phe Ile Arg Pro Ile Pro Thr Trp Asp Glu Trp Pro
385                 390                 395                 400

Glu Phe Ala Arg Glu Thr Phe Gln Ala Phe Arg Thr Thr Asp Val Gly
            405                 410                 415

Arg Lys Leu Ile Ile Asp Gln Asn Val Phe Ile Glu Gly Thr Leu Pro
            420                 425                 430

Met Gly Val Val Arg Pro Leu Thr Glu Val Glu Met Asp His Tyr Arg
            435                 440                 445

Glu Pro Phe Leu Asn Pro Val Asp Arg Glu Pro Leu Trp Arg Phe Pro
            450                 455                 460

Asn Glu Leu Pro Ile Ala Gly Glu Pro Ala Asn Ile Val Ala Leu Val
465                 470                 475                 480

Glu Glu Tyr Met Asp Trp Leu His Gln Ser Pro Val Pro Lys Leu Leu
            485                 490                 495

Phe Trp Gly Thr Pro Gly Val Leu Ile Pro Pro Ala Glu Ala Ala Arg
            500                 505                 510

Leu Ala Lys Ser Leu Pro Asn Cys Lys Ala Val Asp Ile Gly Pro Gly
            515                 520                 525

Leu Asn Leu Leu Gln Glu Asp Asn Pro Asp Leu Ile Gly Ser Glu Ile
            530                 535                 540

Ala Arg Trp Leu Ser Thr Leu Glu Ile Ser Gly Glu Pro Thr Thr Lys
545                 550                 555                 560

Ser Arg Ile Thr Ser Glu Gly Glu Tyr Ile Pro Leu Asp Gln Ile Asp
```

Ile Asn Val Gly Gly Phe Cys Tyr Glu Asn Glu Val
              580                 585

<210> SEQ ID NO 3
<211> LENGTH: 1755
<212> TYPE: DNA
<213> ORGANISM: Artificial
<220> FEATURE:
<223> OTHER INFORMATION: QuasAr2-HaloTag-4 Ligand

<400> SEQUENCE: 3

| | | | |
|---|---|---|---|
| atggtaagta tcgctctgca ggctggttac gacctactgg gtgacggcag acctgaaacc | 60 |
| ctgtggctgg gcatcggcac tctgctgatg ctgattggaa ccttctactt tctggtccgc | 120 |
| ggatggggag tcaccgataa ggatgcccgg gaatattacg ctgtgactat cctggtgtcc | 180 |
| ggaatcgcat ccgccgcata tctgtctatg ttctttggta tcgggcttac tgaggtgtcc | 240 |
| gtcggggcg aaatgttgga tatctattat gccaggtacg cccagtggct gtttaccacc | 300 |
| ccacttctgc tgctgcacct ggcccttctc gctaaggtgg atcgggtgac catcggcacc | 360 |
| ctggtgggtg tggacgccct gatgatcgtc actggcctca tcggagcctt gagccacacg | 420 |
| gccatagcca gatacagttg gtggttgttc tctacaattt gcatgatagt ggtgctctat | 480 |
| gttctggcta catccctgcg atctgctgca aaggagcggg ccccgaggt ggcatctacc | 540 |
| tttaacaccc tgacagctct ggtcttggtg ctgtggaccg cttaccctat cctgtggatc | 600 |
| ataggcactg agggcgctgg cgtggtgggc ctgggcatcg aaactctgct gtttatggtg | 660 |
| ttggacgtga ctgccaaggt cggctttggc tttatcctgt tgagatcccg ggctattctg | 720 |
| ggcgacaccg aggcaccaga acccagtgcc ggtgccgatg tcatggcaga aatcggtact | 780 |
| ggctttccat tcgaccccca ttatgtggaa gtcctgggcg agcgcatgca ctacgtcgat | 840 |
| gttggtccgc gcgatggcac ccctgtgctg ttcctgcacg gtaacccgac ctcctcctac | 900 |
| gtgtggcgca acatcatccc gcatgttgca ccgacccatc gctgcattgc tccagacctg | 960 |
| atcggtatgg gcaaatccga caaaccagac ctgggttatt tcttcgacga ccacgtccgc | 1020 |
| ttcatggatg ccttcatcga agccctgggt ctggaagagg tcgtcctggt cattcacgac | 1080 |
| tggggctccg ctctgggttt ccactgggcc aagcgcaatc cagagcgcgt caaaggtatt | 1140 |
| gcatttatgg agttcatccg ccctatcccg acctgggacg aatggccaga atttgcccgc | 1200 |
| gagaccttcc aggccttccg caccaccgac gtcggccgca agctgatcat cgatcagaac | 1260 |
| gtttttatcg agggtacgct gccgatgggt gtcgtccgcc cgctgactga agtcgagatg | 1320 |
| gaccattacc gcgagccgtt cctgaatcct gttgaccgcg agccactgtg gcgcttccca | 1380 |
| aacgagctgc caatcgccgg tgagccagcg aacatcgtcg cgctggtcga agaatacatg | 1440 |
| gactggctgc accagtcccc tgtcccgaag ctgctgttct ggggcacccc aggcgttctg | 1500 |
| atcccaccgg ccgaagccgc tcgcctggcc aaaagcctgc ctaactgcaa ggctgtggac | 1560 |
| atcggcccgg gtctgaatct gctgcaagaa gacaacccgg acctgatcgg cagcgagatc | 1620 |
| gcgcgctggc tgtcgacgct cgagatttcc ggcgagccaa ccactaagag tagaatcaca | 1680 |
| agcgaaggcg agtacatccc cctggatcaa atagacataa atgtaggtgg attttgttat | 1740 |
| gagaatgaag tataa | 1755 |

<210> SEQ ID NO 4
<211> LENGTH: 584
<212> TYPE: PRT

<213> ORGANISM: Artificial
<220> FEATURE:
<223> OTHER INFORMATION: QuasAr2-HaloTag-4 Ligand

<400> SEQUENCE: 4

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Met Ala
                245                 250                 255

Glu Ile Gly Thr Gly Phe Pro Phe Asp Pro His Tyr Val Glu Val Leu
            260                 265                 270

Gly Glu Arg Met His Tyr Val Asp Val Gly Pro Arg Asp Gly Thr Pro
        275                 280                 285

Val Leu Phe Leu His Gly Asn Pro Thr Ser Ser Tyr Val Trp Arg Asn
    290                 295                 300

Ile Ile Pro His Val Ala Pro Thr His Arg Cys Ile Ala Pro Asp Leu
305                 310                 315                 320

Ile Gly Met Gly Lys Ser Asp Lys Pro Asp Leu Gly Tyr Phe Phe Asp
                325                 330                 335

Asp His Val Arg Phe Met Asp Ala Phe Ile Glu Ala Leu Gly Leu Glu
            340                 345                 350

Glu Val Val Leu Val Ile His Asp Trp Gly Ser Ala Leu Gly Phe His
        355                 360                 365

Trp Ala Lys Arg Asn Pro Glu Arg Val Lys Gly Ile Ala Phe Met Glu
    370                 375                 380

Phe Ile Arg Pro Ile Pro Thr Trp Asp Glu Trp Pro Glu Phe Ala Arg
```

```
                385                 390                 395                 400
        Glu Thr Phe Gln Ala Phe Arg Thr Thr Asp Val Gly Arg Lys Leu Ile
                        405                 410                 415

Ile Asp Gln Asn Val Phe Ile Glu Gly Thr Leu Pro Met Gly Val Val
                        420                 425                 430

Arg Pro Leu Thr Glu Val Glu Met Asp His Tyr Arg Glu Pro Phe Leu
                        435                 440                 445

Asn Pro Val Asp Arg Glu Pro Leu Trp Arg Phe Pro Asn Glu Leu Pro
                        450                 455                 460

Ile Ala Gly Glu Pro Ala Asn Ile Val Ala Leu Val Glu Glu Tyr Met
        465                 470                 475                 480

Asp Trp Leu His Gln Ser Pro Val Pro Lys Leu Leu Phe Trp Gly Thr
                        485                 490                 495

Pro Gly Val Leu Ile Pro Pro Ala Glu Ala Ala Arg Leu Ala Lys Ser
                        500                 505                 510

Leu Pro Asn Cys Lys Ala Val Asp Ile Gly Pro Gly Leu Asn Leu Leu
                        515                 520                 525

Gln Glu Asp Asn Pro Asp Leu Ile Gly Ser Glu Ile Ala Arg Trp Leu
                        530                 535                 540

Ser Thr Leu Glu Ile Ser Gly Glu Pro Thr Thr Lys Ser Arg Ile Thr
        545                 550                 555                 560

Ser Glu Gly Glu Tyr Ile Pro Leu Asp Gln Ile Asp Ile Asn Val Gly
                        565                 570                 575

Gly Phe Cys Tyr Glu Asn Glu Val
                        580

<210> SEQ ID NO 5
<211> LENGTH: 1743
<212> TYPE: DNA
<213> ORGANISM: Artificial
<220> FEATURE:
<223> OTHER INFORMATION: QuasAr2-HaloTag-8 Ligand

<400> SEQUENCE: 5
atggtaagta tcgctctgca ggctggttac gacctactgg gtgacggcag acctgaaacc          60
ctgtggctgg gcatcggcac tctgctgatg ctgattggaa ccttctactt tctggtccgc         120
ggatggggag tcaccgataa ggatgcccgg gaatattacg ctgtgactat cctggtgtcc         180
ggaatcgcat ccgccgcata tctgtctatg ttctttggta tcgggcttac tgaggtgtcc         240
gtcgggggcg aaatgttgga tatctattat gccaggtacg cccagtggct gtttaccacc         300
ccacttctgc tgctgcacct ggcccttctc gctaaggtgg atcgggtgac catcggcacc         360
ctggtgggtg tggacgccct gatgatcgtc actggcctca tcggagcctt gagccacacg         420
gccatagcca gatacagttg gtggttgttc tctacaattt gcatgatagt ggtgctctat         480
gttctggcta catccctgcg atctgctgca aaggagcggg ccccgaggt ggcatctacc          540 tttaacaccc tgacagctct ggtcttggtg ctgtggaccg cttaccctat cctgtggatc         600
ataggcactg agggcgctgg cgtggtgggc ctgggcatcg aaactctgct gtttatggtg         660
ttggacgtga ctgccaaggt cggctttggc tttatcctgt tgagatcccg ggctattctg         720
ggcgacaccg aggcaccaga acccagtgcc atggcagaaa tcggtactgg cttccattc          780 gacccccatt atgtggaagt cctgggcgag cgcatgcact acgtcgatgt tggtccgcgc         840
gatggcaccc tgtgtctgtt cctgcacggt aaccgaccct cctcctacgt gtggcgcaac         900
atcatcccgc atgttgcacc gacccatcgc tgcattgctc cagacctgat cggtatgggc         960
```

| aaatccgaca aaccagacct gggttatttc ttcgacgacc acgtccgctt catggatgcc | 1020 |
| ttcatcgaag ccctgggtct ggaagaggtc gtcctggtca ttcacgactg gggctccgct | 1080 |
| ctgggtttcc actgggccaa gcgcaatcca gagcgcgtca aggtattgc atttatggag | 1140 |
| ttcatccgcc ctatcccgac ctgggacgaa tggccagaat tgcccgcga gaccttccag | 1200 |
| gccttccgca ccaccgacgt cggccgcaag ctgatcatcg atcagaacgt ttttatcgag | 1260 |
| ggtacgctgc cgatgggtgt cgtccgcccg ctgactgaag tcgagatgga ccattaccgc | 1320 |
| gagccgttcc tgaatcctgt tgaccgcgag ccactgtggc gcttcccaaa cgagctgcca | 1380 |
| atcgccggtg agccagcgaa catcgtcgcg ctggtcgaag aatacatgga ctggctgcac | 1440 |
| cagtcccctg tcccgaagct gctgttctgg ggcaccccag gcgttctgat cccaccggcc | 1500 |
| gaagccgctc gcctggccaa aagcctgcct aactgcaagg ctgtggacat cggcccgggt | 1560 |
| ctgaatctgc tgcaagaaga caacccggac ctgatcggca gcgagatcgc gcgctggctg | 1620 |
| tcgacgctcg agatttccgg cgagccaacc actaagagta gaatcacaag cgaaggcgag | 1680 |
| tacatccccc tggatcaaat agacataaat gtaggtggat tttgttatga gaatgaagta | 1740 |
| taa | 1743 |

<210> SEQ ID NO 6
<211> LENGTH: 580
<212> TYPE: PRT
<213> ORGANISM: Artificial
<220> FEATURE:
<223> OTHER INFORMATION: QuasAr2-HaloTag-8 Ligand

<400> SEQUENCE: 6

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
    195                 200                 205

Val Gly Leu Gly Ile Glu Thr Leu Leu Phe Met Val Leu Asp Val Thr

```
                210                 215                 220
Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Met Ala Glu Ile Gly Thr
                245                 250                 255

Gly Phe Pro Phe Asp Pro His Tyr Val Glu Val Leu Gly Glu Arg Met
                260                 265                 270

His Tyr Val Asp Val Gly Pro Arg Asp Gly Thr Pro Val Leu Phe Leu
            275                 280                 285

His Gly Asn Pro Thr Ser Ser Tyr Val Trp Arg Asn Ile Ile Pro His
        290                 295                 300

Val Ala Pro Thr His Arg Cys Ile Ala Pro Asp Leu Ile Gly Met Gly
305                 310                 315                 320

Lys Ser Asp Lys Pro Asp Leu Gly Tyr Phe Phe Asp Asp His Val Arg
                325                 330                 335

Phe Met Asp Ala Phe Ile Glu Ala Leu Gly Leu Glu Glu Val Val Leu
                340                 345                 350

Val Ile His Asp Trp Gly Ser Ala Leu Gly Phe His Trp Ala Lys Arg
            355                 360                 365

Asn Pro Glu Arg Val Lys Gly Ile Ala Phe Met Glu Phe Ile Arg Pro
        370                 375                 380

Ile Pro Thr Trp Asp Glu Trp Pro Glu Phe Ala Arg Glu Thr Phe Gln
385                 390                 395                 400

Ala Phe Arg Thr Thr Asp Val Gly Arg Lys Leu Ile Ile Asp Gln Asn
                405                 410                 415

Val Phe Ile Glu Gly Thr Leu Pro Met Gly Val Val Arg Pro Leu Thr
                420                 425                 430

Glu Val Glu Met Asp His Tyr Arg Glu Pro Phe Leu Asn Pro Val Asp
            435                 440                 445

Arg Glu Pro Leu Trp Arg Phe Pro Asn Glu Leu Pro Ile Ala Gly Glu
        450                 455                 460

Pro Ala Asn Ile Val Ala Leu Val Glu Glu Tyr Met Asp Trp Leu His
465                 470                 475                 480

Gln Ser Pro Val Pro Lys Leu Leu Phe Trp Gly Thr Pro Gly Val Leu
                485                 490                 495

Ile Pro Pro Ala Glu Ala Ala Arg Leu Ala Lys Ser Leu Pro Asn Cys
                500                 505                 510

Lys Ala Val Asp Ile Gly Pro Gly Leu Asn Leu Leu Gln Glu Asp Asn
            515                 520                 525

Pro Asp Leu Ile Gly Ser Glu Ile Ala Arg Trp Leu Ser Thr Leu Glu
        530                 535                 540

Ile Ser Gly Glu Pro Thr Thr Lys Ser Arg Ile Thr Ser Glu Gly Glu
545                 550                 555                 560

Tyr Ile Pro Leu Asp Gln Ile Asp Ile Asn Val Gly Gly Phe Cys Tyr
                565                 570                 575

Glu Asn Glu Val
            580

<210> SEQ ID NO 7
<211> LENGTH: 1731
<212> TYPE: DNA
<213> ORGANISM: Artificial
<220> FEATURE:
<223> OTHER INFORMATION: QuasAr2-HaloTag-12 Ligand
```

<400> SEQUENCE: 7

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aggagcgggg ccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaat ggcagaaatc ggtactggct ttccattcga ccccattat      780
gtggaagtcc tgggcgagcg catgcactac gtcgatgttg tccgcgcga tggcacccct      840
gtgctgttcc tgcacggtaa cccgacctcc tcctacgtgt ggcgcaacat catcccgcat     900
gttgcaccga cccatcgctg cattgctcca gacctgatcg gtatgggcaa atccgacaaa     960
ccagacctgg gttatttctt cgacgaccac gtccgcttca tggatgcctt catcgaagcc    1020
ctgggtctgg aagaggtcgt cctggtcatt cacgactggg gctccgctct gggtttccac    1080
tgggccaagc gcaatccaga gcgcgtcaaa ggtattgcat ttatggagtt catccgccct    1140
atcccgacct gggacgaatg gccagaattt gcccgcgaga ccttccaggc cttccgcacc    1200
accgacgtcg gccgcaagct gatcatcgat cagaacgttt ttatcgaggg tacgctgccg    1260
atgggtgtcg tccgcccgct gactgaagtc gagatggacc attaccgcga gccgttcctg    1320
aatcctgttg accgcgagcc actgtggcgc ttcccaaacg agctgccaat cgccggtgag    1380
ccagcgaaca tcgtcgcgct ggtcgaagaa tacatggact ggctgcacca gtcccctgtc    1440
ccgaagctgc tgttctgggg cacccccagg cgttctgatcc caccggccga agccgctcgc    1500
ctggccaaaa gctgcctaa ctgcaaggct gtggacatcg gcccgggtct gaatctgctg     1560
caagaagaca acccggacct gatcggcagc gagatcgcgc gctggctgtc gacgctcgag    1620
atttccggcg agccaaccac taagagtaga atcacaagcg aaggcgagta catcccctg     1680
gatcaaatag acataaatgt aggtggattt tgttatgaga atgaagtata a              1731
```

<210> SEQ ID NO 8
<211> LENGTH: 576
<212> TYPE: PRT
<213> ORGANISM: Artificial
<220> FEATURE:
<223> OTHER INFORMATION: QuasAr2-HaloTag-12 Ligand

<400> SEQUENCE: 8

```
Met Val Ser Ile Ala Leu Gln Ala Gly Tyr Asp Leu Leu Gly Asp Gly
  1               5                  10                  15

Arg Pro Glu Thr Leu Trp Leu Gly Ile Gly Thr Leu Leu Met Leu Ile
                 20                  25                  30

Gly Thr Phe Tyr Phe Leu Val Arg Gly Trp Gly Val Thr Asp Lys Asp
             35                  40                  45
```

```
Ala Arg Glu Tyr Tyr Ala Val Thr Ile Leu Val Ser Gly Ile Ala Ser
 50              55                  60

Ala Ala Tyr Leu Ser Met Phe Phe Gly Ile Gly Leu Thr Glu Val Ser
 65              70                  75                      80

Val Gly Gly Glu Met Leu Asp Ile Tyr Tyr Ala Arg Tyr Ala Gln Trp
                 85                  90                  95

Leu Phe Thr Thr Pro Leu Leu Leu Leu His Leu Ala Leu Leu Ala Lys
                100             105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Met Ala Glu Ile Gly Thr Gly Phe Pro Phe
                245                 250                 255

Asp Pro His Tyr Val Glu Val Leu Gly Glu Arg Met His Tyr Val Asp
            260                 265                 270

Val Gly Pro Arg Asp Gly Thr Pro Val Leu Phe Leu His Gly Asn Pro
            275                 280                 285

Thr Ser Ser Tyr Val Trp Arg Asn Ile Ile Pro His Val Ala Pro Thr
            290                 295                 300

His Arg Cys Ile Ala Pro Asp Leu Ile Gly Met Gly Lys Ser Asp Lys
305                 310                 315                 320

Pro Asp Leu Gly Tyr Phe Phe Asp Asp His Val Arg Phe Met Asp Ala
                325                 330                 335

Phe Ile Glu Ala Leu Gly Leu Glu Glu Val Val Leu Val Ile His Asp
                340                 345                 350

Trp Gly Ser Ala Leu Gly Phe His Trp Ala Lys Arg Asn Pro Glu Arg
            355                 360                 365

Val Lys Gly Ile Ala Phe Met Glu Phe Ile Arg Pro Ile Pro Thr Trp
            370                 375                 380

Asp Glu Trp Pro Glu Phe Ala Arg Glu Thr Phe Gln Ala Phe Arg Thr
385                 390                 395                 400

Thr Asp Val Gly Arg Lys Leu Ile Ile Asp Gln Asn Val Phe Ile Glu
                405                 410                 415

Gly Thr Leu Pro Met Gly Val Val Arg Pro Leu Thr Glu Val Glu Met
                420                 425                 430

Asp His Tyr Arg Glu Pro Phe Leu Asn Pro Val Asp Arg Glu Pro Leu
            435                 440                 445

Trp Arg Phe Pro Asn Glu Leu Pro Ile Ala Gly Glu Pro Ala Asn Ile
450                 455                 460

Val Ala Leu Val Glu Glu Tyr Met Asp Trp Leu His Gln Ser Pro Val
```

```
        465               470               475               480
Pro Lys Leu Leu Phe Trp Gly Thr Pro Gly Val Leu Ile Pro Pro Ala
                    485               490               495

Glu Ala Ala Arg Leu Ala Lys Ser Leu Pro Asn Cys Lys Ala Val Asp
                500               505               510

Ile Gly Pro Gly Leu Asn Leu Leu Gln Glu Asp Asn Pro Asp Leu Ile
            515               520               525

Gly Ser Glu Ile Ala Arg Trp Leu Ser Thr Leu Glu Ile Ser Gly Glu
        530               535               540

Pro Thr Thr Lys Ser Arg Ile Thr Ser Glu Gly Glu Tyr Ile Pro Leu
545               550               555               560

Asp Gln Ile Asp Ile Asn Val Gly Gly Phe Cys Tyr Glu Asn Glu Val
                565               570               575
```

<210> SEQ ID NO 9
<211> LENGTH: 1719
<212> TYPE: DNA
<213> ORGANISM: Artificial
<220> FEATURE:
<223> OTHER INFORMATION: QuasAr2-HaloTag-16 Ligand

<400> SEQUENCE: 9

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgcccc tgatgatcgt cactggcctc atcggagcct gagccacacg     420
gccatagcca gatacagttg gtggttgttc tctacaattt gcatgatagt ggtgctctat     480
gttctggcta catccctgcg atctgctgca aaggagcggg ccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggaaatcgg tactggcttt ccattcgacc ccattatgt ggaagtcctg     780
ggcgagcgca tgcactacgt cgatgttggt ccgcgcgatg caccccctgt gctgttcctg     840
cacggtaacc cgacctcctc ctacgtgtgg cgcaacatca tcccgcatgt tgcaccgacc     900
catcgctgca ttgctccaga cctgatcggt atgggcaaat ccgacaaacc agacctgggt     960
tatttcttcg acgaccacgt ccgcttcatg gatgccttca tcgaagccct gggtctggaa    1020
gaggtcgtcc tggtcattca cgactggggc tccgctctgg gtttccactg gccaagcgc     1080
aatccagagc gcgtcaaagg tattgcattt atggagttca tccgcccat cccgacctgg    1140
gacgaatggc cagaatttgc ccgcgagacc ttccaggcct tccgcaccac cgacgtcggc    1200
cgcaagctga tcatcgatca gaacgttttt atcgagggta cgctgccgat gggtgtcgtc    1260
cgcccgctga ctgaagtcga gatggaccat accgcgagc cgttcctgaa tcctgttgac    1320
cgcgagccac tgtggcgctt cccaaacgag ctgccaatcg ccggtgagcc agcgaacatc    1380
gtcgcgctgg tcgaagaata catggactgg ctgcaccagt cccctgtccc gaagctgctg    1440
ttctggggca ccccaggcgt tctgatccca ccggccgaag ccgctcgcct ggccaaaagc    1500
```

-continued

```
ctgcctaact gcaaggctgt ggacatcggc ccgggtctga atctgctgca agaagacaac   1560
ccggacctga tcggcagcga gatcgcgcgc tggctgtcga cgctcgagat ttccggcgag   1620
ccaaccacta agagtagaat cacaagcgaa ggcgagtaca tcccctgga tcaaatagac    1680 ataaatgtag gtggattttg ttatgagaat gaagtataa                           1719
```

```
<210> SEQ ID NO 10
<211> LENGTH: 572
<212> TYPE: PRT
<213> ORGANISM: Artificial
<220> FEATURE:
<223> OTHER INFORMATION: QuasAr2-HaloTag-16 Ligand

<400> SEQUENCE: 10
```

| | | | | | | | | | | | | | | |
|---|---|---|---|---|---|---|---|---|---|---|---|---|---|---|
| Met | Val | Ser | Ile | Ala | Leu | Gln | Ala | Gly | Tyr | Asp | Leu | Leu | Gly | Asp | Gly |
| 1 | | | | 5 | | | | | 10 | | | | | 15 | |
| Arg | Pro | Glu | Thr | Leu | Trp | Leu | Gly | Ile | Gly | Thr | Leu | Leu | Met | Leu | Ile |
| | | | 20 | | | | | 25 | | | | | 30 | | |
| Gly | Thr | Phe | Tyr | Phe | Leu | Val | Arg | Gly | Trp | Gly | Val | Thr | Asp | Lys | Asp |
| | | | 35 | | | | 40 | | | | | 45 | | | |
| Ala | Arg | Glu | Tyr | Tyr | Ala | Val | Thr | Ile | Leu | Val | Ser | Gly | Ile | Ala | Ser |
| | 50 | | | | | 55 | | | | | 60 | | | | |
| Ala | Ala | Tyr | Leu | Ser | Met | Phe | Phe | Gly | Ile | Gly | Leu | Thr | Glu | Val | Ser |
| 65 | | | | | 70 | | | | | 75 | | | | | 80 |
| Val | Gly | Gly | Glu | Met | Leu | Asp | Ile | Tyr | Tyr | Ala | Arg | Tyr | Ala | Gln | Trp |
| | | | | 85 | | | | | 90 | | | | | 95 | |
| Leu | Phe | Thr | Thr | Pro | Leu | Leu | Leu | Leu | His | Leu | Ala | Leu | Leu | Ala | Lys |
| | | | 100 | | | | | 105 | | | | | 110 | | |
| Val | Asp | Arg | Val | Thr | Ile | Gly | Thr | Leu | Val | Gly | Val | Asp | Ala | Leu | Met |
| | | | 115 | | | | | 120 | | | | | 125 | | |
| Ile | Val | Thr | Gly | Leu | Ile | Gly | Ala | Leu | Ser | His | Thr | Ala | Ile | Ala | Arg |
| | 130 | | | | | 135 | | | | | 140 | | | | |
| Tyr | Ser | Trp | Trp | Leu | Phe | Ser | Thr | Ile | Cys | Met | Ile | Val | Val | Leu | Tyr |
| 145 | | | | | 150 | | | | | 155 | | | | | 160 |
| Val | Leu | Ala | Thr | Ser | Leu | Arg | Ser | Ala | Ala | Lys | Glu | Arg | Gly | Pro | Glu |
| | | | | 165 | | | | | 170 | | | | | 175 | |
| Val | Ala | Ser | Thr | Phe | Asn | Thr | Leu | Thr | Ala | Leu | Val | Leu | Val | Leu | Trp |
| | | | 180 | | | | | 185 | | | | | 190 | | |
| Thr | Ala | Tyr | Pro | Ile | Leu | Trp | Ile | Ile | Gly | Thr | Glu | Gly | Ala | Gly | Val |
| | | | 195 | | | | | 200 | | | | | 205 | | |
| Val | Gly | Leu | Gly | Ile | Glu | Thr | Leu | Leu | Phe | Met | Val | Leu | Asp | Val | Thr |
| | 210 | | | | | 215 | | | | | 220 | | | | |
| Ala | Lys | Val | Gly | Phe | Gly | Phe | Ile | Leu | Leu | Arg | Ser | Arg | Ala | Ile | Leu |
| 225 | | | | | 230 | | | | | 235 | | | | | 240 |
| Gly | Asp | Thr | Glu | Glu | Ile | Gly | Thr | Gly | Phe | Pro | Phe | Asp | Pro | His | Tyr |
| | | | | 245 | | | | | 250 | | | | | 255 | |
| Val | Glu | Val | Leu | Gly | Glu | Arg | Met | His | Tyr | Val | Asp | Val | Gly | Pro | Arg |
| | | | 260 | | | | | 265 | | | | | 270 | | |
| Asp | Gly | Thr | Pro | Val | Leu | Phe | Leu | His | Gly | Asn | Pro | Thr | Ser | Ser | Tyr |
| | | | 275 | | | | | 280 | | | | | 285 | | |
| Val | Trp | Arg | Asn | Ile | Ile | Pro | His | Val | Ala | Pro | Thr | His | Arg | Cys | Ile |
| | 290 | | | | | 295 | | | | | 300 | | | | |
| Ala | Pro | Asp | Leu | Ile | Gly | Met | Gly | Lys | Ser | Asp | Lys | Pro | Asp | Leu | Gly |
| 305 | | | | | 310 | | | | | 315 | | | | | 320 |

Tyr Phe Phe Asp Asp His Val Arg Phe Met Asp Ala Phe Ile Glu Ala
            325                 330                 335

Leu Gly Leu Glu Glu Val Val Leu Val Ile His Asp Trp Gly Ser Ala
        340                 345                 350

Leu Gly Phe His Trp Ala Lys Arg Asn Pro Glu Arg Val Lys Gly Ile
        355                 360                 365

Ala Phe Met Glu Phe Ile Arg Pro Ile Pro Thr Trp Asp Glu Trp Pro
370                 375                 380

Glu Phe Ala Arg Glu Thr Phe Gln Ala Phe Arg Thr Thr Asp Val Gly
385                 390                 395                 400

Arg Lys Leu Ile Ile Asp Gln Asn Val Phe Ile Glu Gly Thr Leu Pro
                405                 410                 415

Met Gly Val Val Arg Pro Leu Thr Glu Val Glu Met Asp His Tyr Arg
            420                 425                 430

Glu Pro Phe Leu Asn Pro Val Asp Arg Glu Pro Leu Trp Arg Phe Pro
        435                 440                 445

Asn Glu Leu Pro Ile Ala Gly Glu Pro Ala Asn Ile Val Ala Leu Val
    450                 455                 460

Glu Glu Tyr Met Asp Trp Leu His Gln Ser Pro Val Pro Lys Leu Leu
465                 470                 475                 480

Phe Trp Gly Thr Pro Gly Val Leu Ile Pro Pro Ala Glu Ala Ala Arg
                485                 490                 495

Leu Ala Lys Ser Leu Pro Asn Cys Lys Ala Val Asp Ile Gly Pro Gly
            500                 505                 510

Leu Asn Leu Leu Gln Glu Asp Asn Pro Asp Leu Ile Gly Ser Glu Ile
        515                 520                 525

Ala Arg Trp Leu Ser Thr Leu Glu Ile Ser Gly Glu Pro Thr Thr Lys
530                 535                 540

Ser Arg Ile Thr Ser Glu Gly Glu Tyr Ile Pro Leu Asp Gln Ile Asp
545                 550                 555                 560

Ile Asn Val Gly Gly Phe Cys Tyr Glu Asn Glu Val
                565                 570

<210> SEQ ID NO 11
<211> LENGTH: 1713
<212> TYPE: DNA
<213> ORGANISM: Artificial
<220> FEATURE:
<223> OTHER INFORMATION: QuasAr2-HaloTag-18 Ligand

<400> SEQUENCE: 11
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240 gtcggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg ccccgaggt ggcatctacc     540 tttaacaccc tgcagctctc tggtcttgtg ctgtggaccg cttaccctat cctgtggatc     600
ataggcactg agggcgctgg cgtggtgggc ctgggcatcg aaactctgct gtttatggtg     660

```
ttggacgtga ctgccaaggt cggctttggc tttatcctgt tgagatcccg ggctattctg      720
ggcgacacca tcggtactgg ctttccattc gaccccatt atgtggaagt cctgggcgag       780
cgcatgcact acgtcgatgt tggtccgcgc gatggcaccc ctgtgctgtt cctgcacggt      840
aacccgacct cctcctacgt gtggcgcaac atcatcccgc atgttgcacc gacccatcgc      900
tgcattgctc cagacctgat cggtatgggc aaatccgaca accagacct gggttatttc       960 ttcgacgacc acgtccgctt catggatgcc ttcatcgaag ccctgggtct ggaagaggtc     1020
gtcctggtca ttcacgactg ggctccgct ctgggttttcc actgggccaa gcgcaatcca     1080
gagcgcgtca aggtattgc atttatggag ttcatccgcc ctatcccgac ctgggacgaa      1140
tggccagaat tgcccgcga ccttccag gccttccgca ccaccgacgt cggccgcaag         1200
ctgatcatcg atcagaacgt ttttatcgag ggtacgctgc cgatgggtgt cgtccgcccg    1260
ctgactgaag tcgagatgga ccattaccgc gagccgttcc tgaatcctgt tgaccgcgag     1320
ccactgtggc gcttcccaaa cgagctgcca atcgccggtg agccagcgaa catcgtcgcg    1380
ctggtcgaag aatacatgga ctggctgcac cagtcccctg tcccgaagct gctgttctgg     1440
ggcaccccag gcgttctgat cccaccggcc gaagccgctc gcctggccaa agcctgcct     1500 aactgcaagg ctgtggacat cggcccgggt ctgaatctgc tgcaagaaga caacccggac    1560
ctgatcggca gcgagatcgc gcgctggctg tcgacgctcg agatttccgg cgagccaacc    1620
actaagagta gaatcacaag cgaaggcgag tacatccccc tggatcaaat agacataaat   1680
gtaggtggat tttgttatga gaatgaagta taa                                  1713
```

<210> SEQ ID NO 12
<211> LENGTH: 570
<212> TYPE: PRT
<213> ORGANISM: Artificial
<220> FEATURE:
<223> OTHER INFORMATION: QuasAr2-HaloTag-18 Ligand

<400> SEQUENCE: 12

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Ser Gly Ile Ala Ser
        50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175
```

```
Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Arg Ser Arg Ala Ile Leu
225                 230                 235                 240

Gly Asp Thr Ile Gly Thr Gly Phe Pro Phe Asp Pro His Tyr Val Glu
                245                 250                 255

Val Leu Gly Glu Arg Met His Tyr Val Asp Val Gly Pro Arg Asp Gly
            260                 265                 270

Thr Pro Val Leu Phe Leu His Gly Asn Pro Thr Ser Ser Tyr Val Trp
        275                 280                 285

Arg Asn Ile Ile Pro His Val Ala Pro Thr His Arg Cys Ile Ala Pro
290                 295                 300

Asp Leu Ile Gly Met Gly Lys Ser Asp Lys Pro Asp Leu Gly Tyr Phe
305                 310                 315                 320

Phe Asp Asp His Val Arg Phe Met Asp Ala Phe Ile Glu Ala Leu Gly
                325                 330                 335

Leu Glu Glu Val Val Leu Val Ile His Asp Trp Gly Ser Ala Leu Gly
            340                 345                 350

Phe His Trp Ala Lys Arg Asn Pro Glu Arg Val Lys Gly Ile Ala Phe
        355                 360                 365

Met Glu Phe Ile Arg Pro Ile Pro Thr Trp Asp Glu Trp Pro Glu Phe
    370                 375                 380

Ala Arg Glu Thr Phe Gln Ala Phe Arg Thr Thr Asp Val Gly Arg Lys
385                 390                 395                 400

Leu Ile Ile Asp Gln Asn Val Phe Ile Glu Gly Thr Leu Pro Met Gly
                405                 410                 415

Val Val Arg Pro Leu Thr Glu Val Glu Met Asp His Tyr Arg Glu Pro
            420                 425                 430

Phe Leu Asn Pro Val Asp Arg Glu Pro Leu Trp Arg Phe Pro Asn Glu
        435                 440                 445

Leu Pro Ile Ala Gly Glu Pro Ala Asn Ile Val Ala Leu Val Glu Glu
    450                 455                 460

Tyr Met Asp Trp Leu His Gln Ser Pro Val Pro Lys Leu Leu Phe Trp
465                 470                 475                 480

Gly Thr Pro Gly Val Leu Ile Pro Pro Ala Glu Ala Arg Leu Ala
                485                 490                 495

Lys Ser Leu Pro Asn Cys Lys Ala Val Asp Ile Gly Pro Gly Leu Asn
            500                 505                 510

Leu Leu Gln Glu Asp Asn Pro Asp Leu Ile Gly Ser Glu Ile Ala Arg
        515                 520                 525

Trp Leu Ser Thr Leu Glu Ile Ser Gly Glu Pro Thr Thr Lys Ser Arg
    530                 535                 540

Ile Thr Ser Glu Gly Glu Tyr Ile Pro Leu Asp Gln Ile Asp Ile Asn
545                 550                 555                 560

Val Gly Gly Phe Cys Tyr Glu Asn Glu Val
                565                 570

<210> SEQ ID NO 13
<211> LENGTH: 1707
```

<212> TYPE: DNA
<213> ORGANISM: Artificial
<220> FEATURE:
<223> OTHER INFORMATION: QuasAr2-HaloTag-20 Ligand

<400> SEQUENCE: 13

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcggggcg aaatgttgga tatctattat gccaggtacg cccagtggct gtttaccacc     300
ccacttctgc tgctgcacct ggccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aggagcggg ccccgaggt ggcatctacc     540
tttaacaccc tgacagctct ggtcttggtg ctgtggaccg cttaccctat cctgtggatc     600
ataggcactg agggcgctgg cgtggtgggc ctggcatcg aaactctgct gtttatggtg     660
ttggacgtga ctgccaaggt cggctttggc tttatcctgt tgagatcccg ggctattctg     720
ggcgacacca ctggctttcc attcgacccc cattatgtgg aagtcctggg cgagcgcatg     780
cactacgtcg atgttggtcc gcgcgatggc acccctgtgc tgttcctgca cggtaacccg     840
acctcctcct acgtgtggcg caacatcatc ccgcatgttg caccgaccca tcgctgcatt     900
gctccagacc tgatcggtat gggcaaatcc gacaaaccag acctgggtta tttcttcgac     960
gaccacgtcc gcttcatgga tgccttcatc gaagccctgg gtctggaaga ggtcgtcctg    1020
gtcattcacg actggggctc cgctctgggt ttccactggg ccaagcgcaa tccagagcgc    1080
gtcaaaggta ttgcatttat ggagttcatc cgccctatcc cgacctggga cgaatggcca    1140
gaatttgccc gcgagacctt ccaggccttc cgcaccaccg acgtcggccg caagctgatc    1200
atcgatcaga acgtttttat cgagggtacg ctgccgatgg gtgtcgtccg cccgctgact    1260
gaagtcgaga tggaccatta ccgcgagccg ttcctgaatc ctgttgaccg cgagccactg    1320
tggcgcttcc caaacgagct gccaatcgcc ggtgagccag cgaacatcgt cgcgctggtc    1380
gaagaataca tggactggct gcaccagtcc cctgtcccga gctgctgtt ctggggcacc    1440
ccaggcgttc tgatcccacc ggccgaagcc gctcgcctgg ccaaaagcct gcctaactgc    1500
aaggctgtgg acatcggccc gggtctgaat ctgctgcaag aagacaaccc ggacctgatc    1560
ggcagcgaga tcgcgcgctg gctgtcgacg ctcgagattt ccggcgagcc aaccactaag    1620
agtagaatca aagcgaagg cgagtacatc ccctggatc aaatagacat aaatgtaggt    1680
ggattttgtt atgagaatga agtataa                                        1707
```

<210> SEQ ID NO 14
<211> LENGTH: 568
<212> TYPE: PRT
<213> ORGANISM: Artificial
<220> FEATURE:
<223> OTHER INFORMATION: QuasAr2-HaloTag-20 Ligand

<400> SEQUENCE: 14

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
```

-continued

```
                20                  25                  30
Gly Thr Phe Tyr Phe Leu Val Arg Gly Trp Gly Val Thr Asp Lys Asp
            35                  40                  45
Ala Arg Glu Tyr Tyr Ala Val Thr Ile Leu Val Ser Gly Ile Ala Ser
50                  55                  60
Ala Ala Tyr Leu Ser Met Phe Phe Gly Ile Gly Leu Thr Glu Val Ser
65                  70                  75                  80
Val Gly Gly Glu Met Leu Asp Ile Tyr Tyr Ala Arg Tyr Ala Gln Trp
                85                  90                  95
Leu Phe Thr Thr Pro Leu Leu Leu His Leu Ala Leu Leu Ala Lys
            100                 105                 110
Val Asp Arg Val Thr Ile Gly Thr Leu Val Gly Val Asp Ala Leu Met
            115                 120                 125
Ile Val Thr Gly Leu Ile Gly Ala Leu Ser His Thr Ala Ile Ala Arg
            130                 135                 140
Tyr Ser Trp Trp Leu Phe Ser Thr Ile Cys Met Ile Val Val Leu Tyr
145                 150                 155                 160
Val Leu Ala Thr Ser Leu Arg Ser Ala Ala Lys Glu Arg Gly Pro Glu
            165                 170                 175
Val Ala Ser Thr Phe Asn Thr Leu Thr Ala Leu Val Leu Val Leu Trp
            180                 185                 190
Thr Ala Tyr Pro Ile Leu Trp Ile Ile Gly Thr Glu Gly Ala Gly Val
            195                 200                 205
Val Gly Leu Gly Ile Glu Thr Leu Leu Phe Met Val Leu Asp Val Thr
            210                 215                 220
Ala Lys Val Gly Phe Gly Phe Ile Leu Leu Arg Ser Arg Ala Ile Leu
225                 230                 235                 240
Gly Asp Thr Thr Gly Phe Pro Phe Asp Pro His Tyr Val Glu Val Leu
            245                 250                 255
Gly Glu Arg Met His Tyr Val Asp Val Gly Pro Arg Asp Gly Thr Pro
            260                 265                 270
Val Leu Phe Leu His Gly Asn Pro Thr Ser Ser Tyr Val Trp Arg Asn
            275                 280                 285
Ile Ile Pro His Val Ala Pro Thr His Arg Cys Ile Ala Pro Asp Leu
            290                 295                 300
Ile Gly Met Gly Lys Ser Asp Lys Pro Asp Leu Gly Tyr Phe Phe Asp
305                 310                 315                 320
Asp His Val Arg Phe Met Asp Ala Phe Ile Glu Ala Leu Gly Leu Glu
            325                 330                 335
Glu Val Val Leu Val Ile His Asp Trp Gly Ser Ala Leu Gly Phe His
            340                 345                 350
Trp Ala Lys Arg Asn Pro Glu Arg Val Lys Gly Ile Ala Phe Met Glu
            355                 360                 365
Phe Ile Arg Pro Ile Pro Thr Trp Asp Glu Trp Pro Glu Phe Ala Arg
            370                 375                 380
Glu Thr Phe Gln Ala Phe Arg Thr Thr Asp Val Gly Arg Lys Leu Ile
385                 390                 395                 400
Ile Asp Gln Asn Val Phe Ile Glu Gly Thr Leu Pro Met Gly Val Val
            405                 410                 415
Arg Pro Leu Thr Glu Val Glu Met Asp His Tyr Arg Glu Pro Phe Leu
            420                 425                 430
Asn Pro Val Asp Arg Glu Pro Leu Trp Arg Phe Pro Asn Glu Leu Pro
            435                 440                 445
```

```
Ile Ala Gly Glu Pro Ala Asn Ile Val Ala Leu Val Glu Glu Tyr Met
        450                 455                 460
Asp Trp Leu His Gln Ser Pro Val Pro Lys Leu Leu Phe Trp Gly Thr
465                 470                 475                 480
Pro Gly Val Leu Ile Pro Pro Ala Glu Ala Ala Arg Leu Ala Lys Ser
                485                 490                 495
Leu Pro Asn Cys Lys Ala Val Asp Ile Gly Pro Gly Leu Asn Leu Leu
            500                 505                 510
Gln Glu Asp Asn Pro Asp Leu Ile Gly Ser Glu Ile Ala Arg Trp Leu
        515                 520                 525
Ser Thr Leu Glu Ile Ser Gly Glu Pro Thr Thr Lys Ser Arg Ile Thr
    530                 535                 540
Ser Glu Gly Glu Tyr Ile Pro Leu Asp Gln Ile Asp Ile Asn Val Gly
545                 550                 555                 560
Gly Phe Cys Tyr Glu Asn Glu Val
                565

<210> SEQ ID NO 15
<211> LENGTH: 1701
<212> TYPE: DNA
<213> ORGANISM: Artificial
<220> FEATURE:
<223> OTHER INFORMATION: QuasAr2-HaloTag-22 Ligand

<400> SEQUENCE: 15
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtctatg ttctttggta tcgggcttac tgaggtgtcc     240
gtcgggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aaggagcggg cccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacacct ttccattcga cccccattat gtggaagtcc tgggcgagcg catgcactac     780
gtcgatgttg tccgcgcga tggcaccccct gtgctgttcc tgcacggtaa cccgacctcc     840
tcctacgtgt ggcgcaacat catcccgcat gttgcaccga cccatcgctg cattgctcca     900
gacctgatcg gtatgggcaa atccgacaaa ccagacctgg ttatttctt cgacgaccac     960
gtccgcttca tggatgcctt catcgaagcc ctgggtctgg aagaggtcgt cctggtcatt    1020
cacgactggg gctccgctct gggttttcca ctgggccaag cgcaatccaga gcgcgtcaaa    1080
ggtattgcat ttatggagtt catccgccct atcccgacct gggacgaatg ccagaatttt    1140
gcccgcgaga ccttccaggc cttccgcacc accgacgtcg ccgcaagct gatcatcgat    1200
cagaacgttt ttatcgaggg tacgctgccg atgggtgtcg tccgcccgct gactgaagtc    1260
gagatggacc attaccgcga gccgttcctg aatcctgttg accgcgagcc actgtggcgc    1320
```

```
ttcccaaacg agctgccaat cgccggtgag ccagcgaaca tcgtcgcgct ggtcgaagaa    1380
tacatggact ggctgcacca gtcccctgtc ccgaagctgc tgttctgggg cacccccaggc   1440 gttctgatcc caccggccga agccgctcgc ctggccaaaa gcctgcctaa ctgcaaggct    1500
gtggacatcg gcccgggtct gaatctgctg caagaagaca acccggacct gatcggcagc    1560
gagatcgcgc gctggctgtc gacgctcgag atttccggcg agccaaccac taagagtaga    1620
atcacaagcg aaggcgagta catccccctg gatcaaatag acataaatgt aggtggattt    1680
tgttatgaga atgaagtata a                                              1701
```

<210> SEQ ID NO 16
<211> LENGTH: 566
<212> TYPE: PRT
<213> ORGANISM: Artificial
<220> FEATURE:
<223> OTHER INFORMATION: QuasAr2-HaloTag-22 Ligand

<400> SEQUENCE: 16

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Ser Gly Ile Ala Ser
        50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu His Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Phe Pro Phe Asp Pro His Tyr Val Glu Val Leu Gly Glu
                245                 250                 255

Arg Met His Tyr Val Asp Val Gly Pro Arg Asp Gly Thr Pro Val Leu
            260                 265                 270

Phe Leu His Gly Asn Pro Thr Ser Ser Tyr Val Trp Arg Asn Ile Ile
        275                 280                 285

Pro His Val Ala Pro Thr His Arg Cys Ile Ala Pro Asp Leu Ile Gly
```

```
                290             295             300
    Met Gly Lys Ser Asp Lys Pro Asp Leu Gly Tyr Phe Phe Asp Asp His
    305                 310                 315                 320

Val Arg Phe Met Asp Ala Phe Ile Glu Ala Leu Gly Leu Glu Glu Val
                    325                 330                 335

Val Leu Val Ile His Asp Trp Gly Ser Ala Leu Gly Phe His Trp Ala
                340                 345                 350

Lys Arg Asn Pro Glu Arg Val Lys Gly Ile Ala Phe Met Glu Phe Ile
                355                 360                 365

Arg Pro Ile Pro Thr Trp Asp Glu Trp Pro Glu Phe Ala Arg Glu Thr
                370                 375                 380

Phe Gln Ala Phe Arg Thr Thr Asp Val Gly Arg Lys Leu Ile Ile Asp
    385                 390                 395                 400

Gln Asn Val Phe Ile Glu Gly Thr Leu Pro Met Gly Val Val Arg Pro
                        405                 410                 415

Leu Thr Glu Val Glu Met Asp His Tyr Arg Glu Pro Phe Leu Asn Pro
                    420                 425                 430

Val Asp Arg Glu Pro Leu Trp Arg Phe Pro Asn Glu Leu Pro Ile Ala
                435                 440                 445

Gly Glu Pro Ala Asn Ile Val Ala Leu Val Glu Glu Tyr Met Asp Trp
    450                 455                 460

Leu His Gln Ser Pro Val Pro Lys Leu Leu Phe Trp Gly Thr Pro Gly
    465                 470                 475                 480

Val Leu Ile Pro Pro Ala Glu Ala Ala Arg Leu Ala Lys Ser Leu Pro
                    485                 490                 495

Asn Cys Lys Ala Val Asp Ile Gly Pro Gly Leu Asn Leu Leu Gln Glu
                    500                 505                 510

Asp Asn Pro Asp Leu Ile Gly Ser Glu Ile Ala Arg Trp Leu Ser Thr
                515                 520                 525

Leu Glu Ile Ser Gly Glu Pro Thr Thr Lys Ser Arg Ile Thr Ser Glu
                530                 535                 540

Gly Glu Tyr Ile Pro Leu Asp Gln Ile Asp Ile Asn Val Gly Gly Phe
    545                 550                 555                 560

Cys Tyr Glu Asn Glu Val
                    565
```

<210> SEQ ID NO 17
<211> LENGTH: 1797
<212> TYPE: DNA
<213> ORGANISM: Artificial
<220> FEATURE:
<223> OTHER INFORMATION: QuasAr2-cpHaloTag Ligand

<400> SEQUENCE: 17

| | |
|---|---|
| atggtaagta tcgctctgca ggctggttac gacctactgg gtgacggcag acctgaaacc | 60 |
| ctgtggctgg gcatcggcac tctgctgatg ctgattggaa ccttctactt tctggtccgc | 120 |
| ggatggggag tcaccgataa ggatgcccgg gaatattacg ctgtgactat cctggtgtcc | 180 |
| ggaatcgcat ccgccgcata tctgtctatg ttctttggta tcgggcttac tgaggtgtcc | 240 |
| gtcggggggcg aaatgttgga tatctattat gccaggtacg cccagtggct gtttaccacc | 300 |
| ccacttctgc tgctgcacct ggcccttctc gctaaggtgg atcgggtgac catcggcacc | 360 |
| ctggtgggtg tggacgccct gatgatcgtc actggcctca tcggagcctt gagccacacg | 420 |
| gccatagcca gatacagttg gtggttgttc tctacaattt gcatgatagt ggtgctctat | 480 |

|  |  |
|---|---|
| gttctggcta catccctgcg atctgctgca aaggagcggg gccccgaggt ggcatctacc | 540 |
| tttaacaccc tgacagctct ggtcttggtg ctgtggaccg cttaccctat cctgtggatc | 600 |
| ataggcactg agggcgctgg cgtggtgggc ctgggcatcg aaactctgct gtttatggtg | 660 |
| ttggacgtga ctgccaaggt cggctttggc tttatcctgt tgagatcccg ggctattctg | 720 |
| ggcgacaccg aggcaccaga acccagtgcc ggtgccgatg tcagtgccgc cgacaccttc | 780 |
| caggccttcc gcaccaccga cgtcggccgc aagctgatca tcgatcagaa cgttttatc | 840 |
| gagggtacgc tgccgatggg tgtcgtccgc ccgctgactg aagtcgagat ggaccattac | 900 |
| cgcgagccgt tcctgaatcc tgttgaccgc gagccactgt ggcgcttccc aaacgagctg | 960 |
| ccaatcgccg gtgagccagc gaacatcgtc gcgctggtcg aagaatacat ggactggctg | 1020 |
| caccagtccc ctgtcccgaa gctgctgttc tggggcaccc caggcgttct gatcccaccg | 1080 |
| gccgaagccc tcgcctggc caaaagcctg cctaactgca aggctgtgga catcggcccg | 1140 |
| ggtctgaatc tgctgcaaga agacaacccg gacctgatcg gcagcgagat cgcgcgctgg | 1200 |
| ctgtcgacgc tcgagatttc cggcgagcca accactggag gcagcggagg cacaggaggc | 1260 |
| agcggaggca caggaggcag catggcagaa atcggtactg gctttccatt cgacccccat | 1320 |
| tatgtggaag tcctgggcga gcgcatgcac tacgtcgatg ttggtccgcg cgatggcacc | 1380 |
| cctgtgctgt tcctgcacgg taacccgacc tcctcctacg tgtggcgcaa catcatcccg | 1440 |
| catgttgcac cgaccatcg ctgcattgct ccagacctga tcggtatggg caaatccgac | 1500 |
| aaaccagacc tgggttattt cttcgacgac cacgtccgct tcatggatgc cttcatcgaa | 1560 |
| gccctgggtc tggaagaggt cgtcctggtc attcacgact ggggctccgc tctgggtttc | 1620 |
| cactgggcca gcgcaatcc agagcgcgtc aaaggtattg catttatgga gttcatccgc | 1680 |
| cctatcccga cctgggacga atggccaaag agtagaatca aagcgaagg cgagtacatc | 1740 |
| cccctggatc aaatagacat aaatgtaggt ggattttgtt atgagaatga agtataa | 1797 |

<210> SEQ ID NO 18
<211> LENGTH: 598
<212> TYPE: PRT
<213> ORGANISM: Artificial
<220> FEATURE:
<223> OTHER INFORMATION: QuasAr2-cpHaloTag Ligand

<400> SEQUENCE: 18

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
```

```
            130                 135                 140
Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Thr Phe Gln Ala Phe Arg Thr Thr Asp Val Gly Arg Lys Leu
            260                 265                 270

Ile Ile Asp Gln Asn Val Phe Ile Glu Gly Thr Leu Pro Met Gly Val
            275                 280                 285

Val Arg Pro Leu Thr Glu Val Glu Met Asp His Tyr Arg Glu Pro Phe
            290                 295                 300

Leu Asn Pro Val Asp Arg Glu Pro Leu Trp Arg Phe Pro Asn Glu Leu
305                 310                 315                 320

Pro Ile Ala Gly Glu Pro Ala Asn Ile Val Ala Leu Val Glu Glu Tyr
                325                 330                 335

Met Asp Trp Leu His Gln Ser Pro Val Pro Lys Leu Leu Phe Trp Gly
            340                 345                 350

Thr Pro Gly Val Leu Ile Pro Pro Ala Glu Ala Ala Arg Leu Ala Lys
            355                 360                 365

Ser Leu Pro Asn Cys Lys Ala Val Asp Ile Gly Pro Gly Leu Asn Leu
            370                 375                 380

Leu Gln Glu Asp Asn Pro Asp Leu Ile Gly Ser Glu Ile Ala Arg Trp
385                 390                 395                 400

Leu Ser Thr Leu Glu Ile Ser Gly Glu Pro Thr Thr Gly Gly Ser Gly
                405                 410                 415

Gly Thr Gly Gly Ser Gly Gly Thr Gly Gly Ser Met Ala Glu Ile Gly
                420                 425                 430

Thr Gly Phe Pro Phe Asp Pro His Tyr Val Glu Val Leu Gly Glu Arg
            435                 440                 445

Met His Tyr Val Asp Val Gly Pro Arg Asp Gly Thr Pro Val Leu Phe
            450                 455                 460

Leu His Gly Asn Pro Thr Ser Ser Tyr Val Trp Arg Asn Ile Ile Pro
465                 470                 475                 480

His Val Ala Pro Thr His Arg Cys Ile Ala Pro Asp Leu Ile Gly Met
                485                 490                 495

Gly Lys Ser Asp Lys Pro Asp Leu Gly Tyr Phe Phe Asp Asp His Val
            500                 505                 510

Arg Phe Met Asp Ala Phe Ile Glu Ala Leu Gly Leu Glu Glu Val Val
            515                 520                 525

Leu Val Ile His Asp Trp Gly Ser Ala Leu Gly Phe His Trp Ala Lys
            530                 535                 540

Arg Asn Pro Glu Arg Val Lys Gly Ile Ala Phe Met Glu Phe Ile Arg
545                 550                 555                 560
```

```
Pro Ile Pro Thr Trp Asp Glu Trp Pro Lys Ser Arg Ile Thr Ser Glu
                565                 570                 575

Gly Glu Tyr Ile Pro Leu Asp Gln Ile Asp Ile Asn Val Gly Gly Phe
            580                 585                 590

Cys Tyr Glu Asn Glu Val
        595
```

<210> SEQ ID NO 19
<211> LENGTH: 1365
<212> TYPE: DNA
<213> ORGANISM: Artificial
<220> FEATURE:
<223> OTHER INFORMATION: QuasAr2-SNAP-Tag Ligand

<400> SEQUENCE: 19

```
atggtaagta tcgctctgca ggctggttac gacctactgg gtgacggcag acctgaaacc      60
ctgtggctgg gcatcggcac tctgctgatg ctgattggaa ccttctactt tctggtccgc     120
ggatggggag tcaccgataa ggatgcccgg gaatattacg ctgtgactat cctggtgtcc     180
ggaatcgcat ccgccgcata tctgtcatgt tctttggta tcgggcttac tgaggtgtcc     240
gtcggggggcg aaatgttgga tatctattat gccaggtacg cccagtggct gtttaccacc     300
ccacttctgc tgctgcacct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
gttctggcta catccctgcg atctgctgca aggagcgggg ccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggacaaaga ctgcgaaatg aagcgcacca ccctggatag ccctctgggc     780
aagctggaac tgtctgggtg cgaacagggc ctgcaccgta tcatcttcct gggcaaagga     840
acatctgccg ccgacgccgt ggaagtgcct gccccagccg ccgtgctggg cggaccagag     900
ccactgatgc aggccaccgc ctggctcaac gcctactttc accagcctga ggccatcgag     960
gagttccctg tgccagccct gcaccaccca gtgttccagc aggagagctt accccgccag    1020
gtgctgtgga aactgctgaa agtggtgaag ttcggagagg tcatcagcta cagccacctg    1080
gccgccctgg ccggcaatcc cgccgccacc gccgccgtga aaaccgccct gagcggaaat    1140
cccgtgccca ttctgatccc ctgccaccgg gtggtgcagg cgacctgga cgtgggggc    1200
tacgagggcg gctcgccgt gaaagagtgg ctgctggccc acgagggcca cagactgggc    1260
aagcctgggc tgggtaagag tagaatcaca agcgaaggcg agtacatccc cctggatcaa    1320
atagacataa atgtaggtgg attttgttat gagaatgaag tataa                   1365
```

<210> SEQ ID NO 20
<211> LENGTH: 454
<212> TYPE: PRT
<213> ORGANISM: Artificial
<220> FEATURE:
<223> OTHER INFORMATION: QuasAr2-SNAP-Tag Ligand

<400> SEQUENCE: 20

```
Met Val Ser Ile Ala Leu Gln Ala Gly Tyr Asp Leu Leu Gly Asp Gly
1               5                   10                  15
```

-continued

```
Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Ser Gly Ile Ala Ser
50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Gln Trp
                85                  90                  95

Leu Phe Thr Thr Pro Leu Leu Leu Leu His Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Asp Lys Asp Cys Glu Met Lys Arg Thr Thr Leu Asp
                245                 250                 255

Ser Pro Leu Gly Lys Leu Glu Leu Ser Gly Cys Glu Gln Gly Leu His
            260                 265                 270

Arg Ile Ile Phe Leu Gly Lys Gly Thr Ser Ala Ala Asp Ala Val Glu
            275                 280                 285

Val Pro Ala Pro Ala Ala Val Leu Gly Gly Pro Glu Pro Leu Met Gln
290                 295                 300

Ala Thr Ala Trp Leu Asn Ala Tyr Phe His Gln Pro Glu Ala Ile Glu
305                 310                 315                 320

Glu Phe Pro Val Pro Ala Leu His His Pro Val Phe Gln Gln Glu Ser
                325                 330                 335

Phe Thr Arg Gln Val Leu Trp Lys Leu Leu Lys Val Val Lys Phe Gly
            340                 345                 350

Glu Val Ile Ser Tyr Ser His Leu Ala Ala Leu Ala Gly Asn Pro Ala
            355                 360                 365

Ala Thr Ala Ala Val Lys Thr Ala Leu Ser Gly Asn Pro Val Pro Ile
370                 375                 380

Leu Ile Pro Cys His Arg Val Val Gln Gly Asp Leu Asp Val Gly Gly
385                 390                 395                 400

Tyr Glu Gly Gly Leu Ala Val Lys Glu Trp Leu Leu Ala His Glu Gly
                405                 410                 415

His Arg Leu Gly Lys Pro Gly Leu Gly Lys Ser Arg Ile Thr Ser Glu
            420                 425                 430

Gly Glu Tyr Ile Pro Leu Asp Gln Ile Asp Ile Asn Val Gly Gly Phe
```

Cys Tyr Glu Asn Glu Val
    450

<210> SEQ ID NO 21
<211> LENGTH: 1812
<212> TYPE: DNA
<213> ORGANISM: Artificial
<220> FEATURE:
<223> OTHER INFORMATION: HaloTag-QuasAr2 Ligand

<400> SEQUENCE: 21

| | | | | | |
|---|---|---|---|---|---|
| atggagacag | acacactcct | gctatgggta | ctgctgctct | gggttccagg | ttccactggt | 60 |
| gacatcggta | ctggctttcc | attcgacccc | cattatgtgg | aagtcctggg | cgagcgcatg | 120 |
| cactacgtcg | atgttggtcc | gcgcgatggc | acccctgtgc | tgttcctgca | cggtaacccg | 180 |
| acctcctcct | acgtgtggcg | caacatcatc | ccgcatgttg | caccgaccca | tcgctgcatt | 240 |
| gctccagacc | tgatcggtat | gggcaaatcc | gacaaaccag | acctgggtta | tttcttcgac | 300 |
| gaccacgtcc | gcttcatgga | tgccttcatc | gaagccctgg | gtctggaaga | ggtcgtcctg | 360 |
| gtcattcacg | actggggctc | cgctctgggt | ttccactggg | ccaagcgcaa | tccagagcgc | 420 |
| gtcaaaggta | ttgcatttat | ggagttcatc | cgccctatcc | cgacctggga | cgaatggcca | 480 |
| gaatttgccc | gcgagacctt | ccaggccttc | cgcaccaccg | acgtcggccg | caagctgatc | 540 |
| atcgatcaga | acgtttttat | cgagggtacg | ctgccgatgg | tgtcgtccg | ccgctgact | 600 |
| gaagtcgaga | tggaccatta | ccgcgagccg | ttcctgaatc | ctgttgaccg | cgagccactg | 660 |
| tggcgcttcc | caaacgagct | gccaatcgcc | ggtgagccag | cgaacatcgt | cgcgctggtc | 720 |
| gaagaataca | tggactggct | gcaccagtcc | cctgtcccga | gctgctgtt | ctggggcacc | 780 |
| ccaggcgttc | tgatcccacc | ggccgaagcc | gctcgcctgg | ccaaaagcct | gcctaactgc | 840 |
| aaggctgtgg | acatcggccc | gggtctgaat | ctgctgcaag | aagacaaccc | ggacctgatc | 900 |
| ggcagcgaga | tcgcgcgctg | gctgtcgacg | ctcgagattt | ccggcgagcc | aaccactatg | 960 |
| gtaagtatcg | ctctgcaggc | tggttacgac | ctactgggtg | acggcagacc | tgaaaccctg | 1020 |
| tggctgggca | tcggcactct | gctgatgctg | attggaacct | tctactttct | ggtccgcgga | 1080 |
| tggggagtca | ccgataagga | tgcccgggaa | tattacgctg | tgactatcct | ggtgtccgga | 1140 |
| atcgcatccg | ccgcatatct | gtctatgttc | tttggtatcg | gcttactga | ggtgtccgtc | 1200 |
| gggggcgaaa | tgttggatat | ctattatgcc | aggtacgccc | agtggctgtt | taccacccca | 1260 |
| cttctgctgc | tgcacctggc | ccttctcgct | aaggtggatc | gggtgaccat | cggcaccctg | 1320 |
| gtgggtgtgg | acgccctgat | gatcgtcact | ggcctcatcg | agccttgag | ccacacggcc | 1380 |
| atagccagat | acagttggtg | ttgttctct | acaatttgca | tgatagtggt | gctctatgtt | 1440 |
| ctggctacat | ccctgcgatc | tgctgcaaag | gagcggggcc | ccgaggtggc | atctacctt | 1500 |
| aacaccctga | cagctctggt | cttggtgctg | tggaccgctt | accctatcct | gtggatcata | 1560 |
| ggcactgagg | gcgctggcgt | ggtgggcctg | ggcatcgaaa | ctctgctgtt | tatggtgttg | 1620 |
| gacgtgactg | ccaaggtcgg | ctttggcttt | atcctgttga | gatcccgggc | tattctgggc | 1680 |
| gacaccgagg | caccagaacc | cagtgccggt | gccgatacgt | tgaagagtag | aatcacaagc | 1740 |
| gaaggcgagt | acatcccct | ggatcaaata | gacataaatg | taggtggatt | tgttatgag | 1800 |
| aatgaagtat | aa | | | | | 1812 |

<210> SEQ ID NO 22

<211> LENGTH: 603
<212> TYPE: PRT
<213> ORGANISM: Artificial
<220> FEATURE:
<223> OTHER INFORMATION: HaloTag-QuasAr2 Ligand

<400> SEQUENCE: 22

```
Met Glu Thr Asp Thr Leu Leu Leu Trp Val Leu Leu Leu Trp Val Pro
1               5                   10                  15

Gly Ser Thr Gly Asp Ile Gly Thr Gly Phe Pro Phe Asp Pro His Tyr
            20                  25                  30

Val Glu Val Leu Gly Glu Arg Met His Tyr Val Asp Val Gly Pro Arg
        35                  40                  45

Asp Gly Thr Pro Val Leu Phe Leu His Gly Asn Pro Thr Ser Ser Tyr
    50                  55                  60

Val Trp Arg Asn Ile Ile Pro His Val Ala Pro Thr His Arg Cys Ile
65                  70                  75                  80

Ala Pro Asp Leu Ile Gly Met Gly Lys Ser Asp Lys Pro Asp Leu Gly
                85                  90                  95

Tyr Phe Phe Asp Asp His Val Arg Phe Met Asp Ala Phe Ile Glu Ala
            100                 105                 110

Leu Gly Leu Glu Glu Val Val Leu Val Ile His Asp Trp Gly Ser Ala
        115                 120                 125

Leu Gly Phe His Trp Ala Lys Arg Asn Pro Glu Arg Val Lys Gly Ile
    130                 135                 140

Ala Phe Met Glu Phe Ile Arg Pro Ile Pro Thr Trp Asp Glu Trp Pro
145                 150                 155                 160

Glu Phe Ala Arg Glu Thr Phe Gln Ala Phe Arg Thr Thr Asp Val Gly
                165                 170                 175

Arg Lys Leu Ile Ile Asp Gln Asn Val Phe Ile Glu Gly Thr Leu Pro
            180                 185                 190

Met Gly Val Val Arg Pro Leu Thr Glu Val Glu Met Asp His Tyr Arg
        195                 200                 205

Glu Pro Phe Leu Asn Pro Val Asp Arg Glu Pro Leu Trp Arg Phe Pro
    210                 215                 220

Asn Glu Leu Pro Ile Ala Gly Glu Pro Ala Asn Ile Val Ala Leu Val
225                 230                 235                 240

Glu Glu Tyr Met Asp Trp Leu His Gln Ser Pro Val Pro Lys Leu Leu
                245                 250                 255

Phe Trp Gly Thr Pro Gly Val Leu Ile Pro Pro Ala Glu Ala Ala Arg
            260                 265                 270

Leu Ala Lys Ser Leu Pro Asn Cys Lys Ala Val Asp Ile Gly Pro Gly
        275                 280                 285

Leu Asn Leu Leu Gln Glu Asp Asn Pro Asp Leu Ile Gly Ser Glu Ile
    290                 295                 300

Ala Arg Trp Leu Ser Thr Leu Glu Ile Ser Gly Glu Pro Thr Thr Met
305                 310                 315                 320

Val Ser Ile Ala Leu Gln Ala Gly Tyr Asp Leu Leu Gly Asp Gly Arg
                325                 330                 335

Pro Glu Thr Leu Trp Leu Gly Ile Gly Thr Leu Met Leu Ile Gly
            340                 345                 350

Thr Phe Tyr Phe Leu Val Arg Gly Trp Gly Val Thr Asp Lys Asp Ala
        355                 360                 365

Arg Glu Tyr Tyr Ala Val Thr Ile Leu Val Ser Gly Ile Ala Ser Ala
    370                 375                 380
```

Ala Tyr Leu Ser Met Phe Phe Gly Ile Gly Leu Thr Glu Val Ser Val
385                 390                 395                 400

Gly Gly Glu Met Leu Asp Ile Tyr Tyr Ala Arg Tyr Ala Gln Trp Leu
            405                 410                 415

Phe Thr Thr Pro Leu Leu Leu Leu His Leu Ala Leu Leu Ala Lys Val
            420                 425                 430

Asp Arg Val Thr Ile Gly Thr Leu Val Gly Val Asp Ala Leu Met Ile
            435                 440                 445

Val Thr Gly Leu Ile Gly Ala Leu Ser His Thr Ala Ile Ala Arg Tyr
450                 455                 460

Ser Trp Trp Leu Phe Ser Thr Ile Cys Met Ile Val Val Leu Tyr Val
465                 470                 475                 480

Leu Ala Thr Ser Leu Arg Ser Ala Ala Lys Glu Arg Gly Pro Glu Val
            485                 490                 495

Ala Ser Thr Phe Asn Thr Leu Thr Ala Leu Val Leu Val Leu Trp Thr
            500                 505                 510

Ala Tyr Pro Ile Leu Trp Ile Ile Gly Thr Glu Gly Ala Gly Val Val
            515                 520                 525

Gly Leu Gly Ile Glu Thr Leu Leu Phe Met Val Leu Asp Val Thr Ala
530                 535                 540

Lys Val Gly Phe Gly Phe Ile Leu Leu Arg Ser Arg Ala Ile Leu Gly
545                 550                 555                 560

Asp Thr Glu Ala Pro Glu Pro Ser Ala Gly Ala Asp Thr Leu Lys Ser
            565                 570                 575

Arg Ile Thr Ser Glu Gly Glu Tyr Ile Pro Leu Asp Gln Ile Asp Ile
            580                 585                 590

Asn Val Gly Gly Phe Cys Tyr Glu Asn Glu Val
            595                 600

<210> SEQ ID NO 23
<211> LENGTH: 1659
<212> TYPE: DNA
<213> ORGANISM: Artificial
<220> FEATURE:
<223> OTHER INFORMATION: Ace2N-HaloTag Ligand

<400> SEQUENCE: 23
atggctgacg tggaaaccga gaccggcatg attgcacagt ggattgtctt tgctattatg      60
gctgctgctg ctattgcttt tggagtggct gtgcactttc ggccttcaga gctgaagagc     120
gcatactata tcaacattgc catctgcact atcgccgcta ccgcttacta tgcaatggcc     180
gtgaactacc aggacctgac aatgaatggt gaaaggcagg tggtctacgc aagatatatt     240
aactgggtgc tgaccacacc actgctcctg ctcgatctca tcgtcatgac caagatgggc     300
ggagtgatga tttcttgggt catcggcgca gacattttca tgatcgtgtt tggtattctg     360
ggcgccttcg aggatgaaca caagttcaaa tgggtgtact ttatcgctgg atgtgtgatg     420
caggcagtcc tgcatacgg gatgtataac gccacttgga agacgatct gaagaaaagc      480 cccgagtacc atagctccta tgtcagtctg ctcgtcttcc tgtcaatcct ctgggtgttt     540
tatcctgtcg tgtgggcttt cgggtctggt agtggcgtgc tgtccgtcga caatgaggcc     600
attctcatgg gaatcctgga tgtgctcgct aagccactgt ttggaatggg gtgcctcatt     660
gcccatgaga ctatcttcaa gatcggtact ggctttccat cgaccccca ttatgtggaa     720 gtcctgggcg agcgcatgca ctacgtcgat gttggtccgc gcgatggcac ccctgtgctg     780

```
ttcctgcacg gtaacccgac ctcctcctac gtgtggcgca acatcatccc gcatgttgca      840
ccgacccatc gctgcattgc tccagacctg atcggtatgg gcaaatccga caaaccagac      900
ctgggttatt tcttcgacga ccacgtccgc ttcatggatg ccttcatcga agccctgggt      960
ctggaagagg tcgtcctggt cattcacgac tggggctccg ctctgggttt ccactgggcc     1020
aagcgcaatc agagcgcgt caaaggtatt gcatttatgg agttcatccg ccctatcccg     1080
acctgggacg aatggccaga atttgcccgc gagaccttcc aggccttccg caccaccgac     1140
gtcggccgca agctgatcat cgatcagaac gttttttatcg agggtacgct gccgatgggt     1200
gtcgtccgcc cgctgactga agtcgagatg gaccattacc gcgagccgtt cctgaatcct     1260
gttgaccgcg agccactgtg gcgcttccca acgagctgc caatcgccgg tgagccagcg     1320
aacatcgtcg cgctggtcga agaatacatg gactggctgc accagtcccc tgtcccgaag     1380
ctgctgttct ggggcacccc aggcgttctg atcccaccgg ccgaagccgc tcgcctggcc     1440
aaaagcctgc taactgcaa ggctgtggac atcggcccgg tctgaatct gctgcaagaa     1500
gacaacccgg acctgatcgg cagcgagatc gcgcgctggc tgtcgacgct cgagatttcc     1560
ggcgagccaa ccactaagag caggatcacc agcgagggcg agtacatccc cctggaccag     1620
atcgacatca acgtgttctg ctacgagaac gaggtgtaa                           1659
```

<210> SEQ ID NO 24
<211> LENGTH: 552
<212> TYPE: PRT
<213> ORGANISM: Artificial
<220> FEATURE:
<223> OTHER INFORMATION: Ace2N-HaloTag Ligand

<400> SEQUENCE: 24

```
Met Ala Asp Val Glu Thr Glu Thr Gly Met Ile Ala Gln Trp Ile Val
1               5                   10                  15

Phe Ala Ile Met Ala Ala Ala Ile Ala Phe Gly Val Ala Val His
                20                  25                  30

Phe Arg Pro Ser Glu Leu Lys Ser Ala Tyr Tyr Ile Asn Ile Ala Ile
            35                  40                  45

Cys Thr Ile Ala Ala Thr Ala Tyr Tyr Ala Met Ala Val Asn Tyr Gln
        50                  55                  60

Asp Leu Thr Met Asn Gly Glu Arg Gln Val Val Tyr Ala Arg Tyr Ile
65                  70                  75                  80

Asn Trp Val Leu Thr Thr Pro Leu Leu Leu Asp Leu Ile Val Met
                85                  90                  95

Thr Lys Met Gly Gly Val Met Ile Ser Trp Val Ile Gly Ala Asp Ile
                100                 105                 110

Phe Met Ile Val Phe Gly Ile Leu Gly Ala Phe Glu Asp Glu His Lys
            115                 120                 125

Phe Lys Trp Val Tyr Phe Ile Ala Gly Cys Val Met Gln Ala Val Leu
        130                 135                 140

Thr Tyr Gly Met Tyr Asn Ala Thr Trp Lys Asp Leu Lys Lys Ser
145                 150                 155                 160

Pro Glu Tyr His Ser Ser Tyr Val Ser Leu Leu Val Phe Leu Ser Ile
                165                 170                 175

Leu Trp Val Phe Tyr Pro Val Val Trp Ala Phe Gly Ser Gly Ser Gly
                180                 185                 190

Val Leu Ser Val Asp Asn Glu Ala Ile Leu Met Gly Ile Leu Asp Val
            195                 200                 205
```

Leu Ala Lys Pro Leu Phe Gly Met Gly Cys Leu Ile Ala His Glu Thr
    210                 215                 220

Ile Phe Lys Ile Gly Thr Gly Phe Pro Phe Asp Pro His Tyr Val Glu
225                 230                 235                 240

Val Leu Gly Glu Arg Met His Tyr Val Asp Val Gly Pro Arg Asp Gly
                245                 250                 255

Thr Pro Val Leu Phe Leu His Gly Asn Pro Thr Ser Ser Tyr Val Trp
            260                 265                 270

Arg Asn Ile Ile Pro His Val Ala Pro Thr His Arg Cys Ile Ala Pro
        275                 280                 285

Asp Leu Ile Gly Met Gly Lys Ser Asp Lys Pro Asp Leu Gly Tyr Phe
290                 295                 300

Phe Asp Asp His Val Arg Phe Met Asp Ala Phe Ile Glu Ala Leu Gly
305                 310                 315                 320

Leu Glu Glu Val Val Leu Val Ile His Asp Trp Gly Ser Ala Leu Gly
                325                 330                 335

Phe His Trp Ala Lys Arg Asn Pro Glu Arg Val Lys Gly Ile Ala Phe
            340                 345                 350

Met Glu Phe Ile Arg Pro Ile Pro Thr Trp Asp Glu Trp Pro Glu Phe
        355                 360                 365

Ala Arg Glu Thr Phe Gln Ala Phe Arg Thr Thr Asp Val Gly Arg Lys
370                 375                 380

Leu Ile Ile Asp Gln Asn Val Phe Ile Glu Gly Thr Leu Pro Met Gly
385                 390                 395                 400

Val Val Arg Pro Leu Thr Glu Val Glu Met Asp His Tyr Arg Glu Pro
                405                 410                 415

Phe Leu Asn Pro Val Asp Arg Glu Pro Leu Trp Arg Phe Pro Asn Glu
            420                 425                 430

Leu Pro Ile Ala Gly Glu Pro Ala Asn Ile Val Ala Leu Val Glu Glu
        435                 440                 445

Tyr Met Asp Trp Leu His Gln Ser Pro Val Pro Lys Leu Leu Phe Trp
450                 455                 460

Gly Thr Pro Gly Val Leu Ile Pro Pro Ala Glu Ala Ala Arg Leu Ala
465                 470                 475                 480

Lys Ser Leu Pro Asn Cys Lys Ala Val Asp Ile Gly Pro Gly Leu Asn
                485                 490                 495

Leu Leu Gln Glu Asp Asn Pro Asp Leu Ile Gly Ser Glu Ile Ala Arg
            500                 505                 510

Trp Leu Ser Thr Leu Glu Ile Ser Gly Glu Pro Thr Thr Lys Ser Arg
        515                 520                 525

Ile Thr Ser Glu Gly Glu Tyr Ile Pro Leu Asp Gln Ile Asp Ile Asn
530                 535                 540

Val Phe Cys Tyr Glu Asn Glu Val
545                 550

<210> SEQ ID NO 25
<211> LENGTH: 1614
<212> TYPE: DNA
<213> ORGANISM: Artificial
<220> FEATURE:
<223> OTHER INFORMATION: CiVSD-HaloTag Ligand

<400> SEQUENCE: 25 atggaggat tcgacggttc agatttagt cctccagctg atttagttgg cgttggcggt    60
gcagtcatgc ggaacgtcgt tgacgtcacg ataaatggtg acgtcactgc tccgccgaaa   120

```
gcagcgccaa gaaaaagtga atcggtaaag aaagttcatt ggaatgatgt agaccaagga      180
ccgagtgaaa aaccagagac aagacaggag gaacgaatag atatacccga gatttcaggt      240
ctatggtggg gcgagaatga acatggagtg ggcggtggga gaatggagat acctactact      300
ggtgtaggtc gcgtccagtt tcgtgtccga gcagtgattg atcatctagg gatgcgagcc      360
tttggagtct tcctaattct cttggacatc atcctcatga tcattgatct cagtcttcca      420
ggaaaaagtg aatcttcaca atcctttat gacgggttgg ctttggctct ttcttgttat       480
ttcatgctgg atttaggatt aaggatattt gcctacgggc ccaagaattt cttcaccaac      540
ccctgggagg ttgctgatgg cttgattatc gttgtcacat cgtcgtcac gatattttac       600 actgtgttag atgaatactt tcaagaaaca ggagccgatg gtttggggca gttggttgtg      660
ttggcccgtt tgctgcgtgt ggttcgatta gcaagaatat tttattccca tcaacaaatc      720
ggtactggct ttccattcga ccccattat gtggaagtcc tgggcgagcg catgcactac       780
gtcgatgttg gtccgcgcga tggcacccct gtgctgttcc tgcacggtaa cccgacctcc      840
tcctacgtgt ggcgcaacat catcccgcat gttgcaccga cccatcgctg cattgctcca      900
gacctgatcg gtatgggcaa atccgacaaa ccagacctgg gttatttctt cgacgaccac      960
gtccgcttca tggatgcctt catcgaagcc ctgggtctgg aagaggtcgt cctggtcatt     1020
cacgactggg gctccgctct gggttttcca ctgggccaag cgcaatccaga gcgcgtcaaa    1080 ggtattgcat ttatggagtt catccgccct atcccgacct gggacgaatg gccagaattt     1140
gcccgcgaga ccttccaggc cttcgcacc accgacgtcg gccgcaagct gatcatcgat      1200
cagaacgttt ttatcgaggg tacgctgccg atgggtgtcg tccgcccgct gactgaagtc     1260
gagatggacc attaccgcga gccgttcctg aatcctgttg accgcgagcc actgtggcgc    1320
ttcccaaacg agctgccaat cgccggtgag ccagcgaaca tcgtcgcgct ggtcgaagaa    1380
tacatggact ggctgcacca gtcccctgtc ccgaagctgc tgttctgggg caccccaggc     1440
gttctgatcc caccggccga agccgctcgc ctggccaaaa gcctgcctaa ctgcaaggct    1500
gtggacatcg gcccggggtct gaatctgctg caagaagaca acccggacct gatcggcagc     1560
gagatcgcgc gctggctgtc gacgctcgag atttccggcg agccaaccac ttaa             1614
```

<210> SEQ ID NO 26
<211> LENGTH: 537
<212> TYPE: PRT
<213> ORGANISM: Artificial
<220> FEATURE:
<223> OTHER INFORMATION: CiVSD-HaloTag Ligand

<400> SEQUENCE: 26

```
Met Glu Gly Phe Asp Gly Ser Asp Phe Ser Pro Pro Ala Asp Leu Val
1               5                   10                  15

Gly Val Gly Gly Ala Val Met Arg Asn Val Val Asp Val Thr Ile Asn
                20                  25                  30

Gly Asp Val Thr Ala Pro Pro Lys Ala Ala Pro Arg Lys Ser Glu Ser
            35                  40                  45

Val Lys Lys Val His Trp Asn Asp Val Asp Gln Gly Pro Ser Glu Lys
        50                  55                  60

Pro Glu Thr Arg Gln Glu Arg Ile Asp Ile Pro Glu Ile Ser Gly
65                  70                  75                  80

Leu Trp Trp Gly Glu Asn Glu His Gly Val Gly Gly Arg Met Glu
                85                  90                  95
```

```
Ile Pro Thr Thr Gly Val Gly Arg Val Gln Phe Arg Val Arg Ala Val
            100                 105                 110
Ile Asp His Leu Gly Met Arg Ala Phe Gly Val Phe Leu Ile Leu Leu
            115                 120                 125
Asp Ile Ile Leu Met Ile Ile Asp Leu Ser Leu Pro Gly Lys Ser Glu
        130                 135                 140
Ser Ser Gln Ser Phe Tyr Asp Gly Leu Ala Leu Ala Leu Ser Cys Tyr
145                 150                 155                 160
Phe Met Leu Asp Leu Gly Leu Arg Ile Phe Ala Tyr Gly Pro Lys Asn
                165                 170                 175
Phe Phe Thr Asn Pro Trp Glu Val Ala Asp Gly Leu Ile Ile Val Val
            180                 185                 190
Thr Phe Val Val Thr Ile Phe Tyr Thr Val Leu Asp Glu Tyr Phe Gln
        195                 200                 205
Glu Thr Gly Ala Asp Gly Leu Gly Gln Leu Val Val Leu Ala Arg Leu
    210                 215                 220
Leu Arg Val Val Arg Leu Ala Arg Ile Phe Tyr Ser His Gln Gln Ile
225                 230                 235                 240
Gly Thr Gly Phe Pro Phe Asp Pro His Tyr Val Glu Val Leu Gly Glu
                245                 250                 255
Arg Met His Tyr Val Asp Val Gly Pro Arg Asp Gly Thr Pro Val Leu
            260                 265                 270
Phe Leu His Gly Asn Pro Thr Ser Ser Tyr Val Trp Arg Asn Ile Ile
        275                 280                 285
Pro His Val Ala Pro Thr His Arg Cys Ile Ala Pro Asp Leu Ile Gly
    290                 295                 300
Met Gly Lys Ser Asp Lys Pro Asp Leu Gly Tyr Phe Phe Asp Asp His
305                 310                 315                 320
Val Arg Phe Met Asp Ala Phe Ile Glu Ala Leu Gly Leu Glu Glu Val
                325                 330                 335
Val Leu Val Ile His Asp Trp Gly Ser Ala Leu Gly Phe His Trp Ala
            340                 345                 350
Lys Arg Asn Pro Glu Arg Val Lys Gly Ile Ala Phe Met Glu Phe Ile
        355                 360                 365
Arg Pro Ile Pro Thr Trp Asp Glu Trp Pro Glu Phe Ala Arg Glu Thr
    370                 375                 380
Phe Gln Ala Phe Arg Thr Thr Asp Val Gly Arg Lys Leu Ile Ile Asp
385                 390                 395                 400
Gln Asn Val Phe Ile Glu Gly Thr Leu Pro Met Gly Val Val Arg Pro
                405                 410                 415
Leu Thr Glu Val Glu Met Asp His Tyr Arg Glu Pro Phe Leu Asn Pro
            420                 425                 430
Val Asp Arg Glu Pro Leu Trp Arg Phe Pro Asn Glu Leu Pro Ile Ala
        435                 440                 445
Gly Glu Pro Ala Asn Ile Val Ala Leu Val Glu Glu Tyr Met Asp Trp
    450                 455                 460
Leu His Gln Ser Pro Val Pro Lys Leu Leu Phe Trp Gly Thr Pro Gly
465                 470                 475                 480
Val Leu Ile Pro Pro Ala Glu Ala Ala Arg Leu Ala Lys Ser Leu Pro
                485                 490                 495
Asn Cys Lys Ala Val Asp Ile Gly Pro Gly Leu Asn Leu Leu Gln Glu
            500                 505                 510
Asp Asn Pro Asp Leu Ile Gly Ser Glu Ile Ala Arg Trp Leu Ser Thr
```

515                 520                 525
Leu Glu Ile Ser Gly Glu Pro Thr Thr
          530                 535

<210> SEQ ID NO 27
<211> LENGTH: 1653
<212> TYPE: DNA
<213> ORGANISM: Artificial
<220> FEATURE:
<223> OTHER INFORMATION: CiVSD-cpHaloTag Ligand

<400> SEQUENCE: 27

| | | | | | |
|---|---|---|---|---|---|
| atggagggat | cgacggttc | agattttagt | cctccagctg | atttagttgg | cgttggcggt | 60 |
| gcagtcatgc | ggaacgtcgt | tgacgtcacg | ataaatggtg | acgtcactgc | tccgccgaaa | 120 |
| gcagcgccaa | gaaaaagtga | atcggtaaag | aaagttcatt | ggaatgatgt | agaccaagga | 180 |
| ccgagtgaaa | aaccagagac | aagacaggag | gaacgaatag | atatacccga | gatttcaggt | 240 |
| ctatggtggg | gcgagaatga | acatggagtg | ggcggtggga | gaatggagat | acctactact | 300 |
| ggtgtaggtc | gcgtccagtt | tcgtgtccga | gcagtgattg | atcatctagg | gatgcgagcc | 360 |
| tttggagtct | tcctaattct | cttggacatc | atcctcatga | tcattgatct | cagtcttcca | 420 |
| ggaaaaagtg | aatcttcaca | atccttttat | gacgggttgg | ctttggctct | tcttgttat | 480 |
| ttcatgctgg | atttaggatt | aaggatattt | gcctacgggc | caagaatttt | cttcaccaac | 540 |
| ccctgggagg | ttgctgatgg | cttgattatc | gttgtcacat | tcgtcgtcac | gatattttac | 600 |
| actgtgttag | atgaatactt | tcaagaaaca | ggagccgatg | gttgggggca | gttggttgtg | 660 |
| ttggcccgtt | tgctgcgtgt | ggttcgatta | gcaagaatat | tttattccca | tcaacaaacc | 720 |
| ttccaggcct | tccgcaccac | cgacgtcggc | cgcaagctga | tcatcgatca | gaacgttttt | 780 |
| atcgagggta | cgctgccgat | gggtgtcgtc | cgcccgctga | ctgaagtcga | gatggaccat | 840 |
| taccgcgagc | cgttcctgaa | tcctgttgac | cgcgagccac | tgtggcgctt | cccaaacgag | 900 |
| ctgccaatcg | ccggtgagcc | agcgaacatc | gtcgcgctgg | tcgaagaata | catggactgg | 960 |
| ctgcaccagt | cccctgtccc | gaagctgctg | ttctggggca | ccccaggcgt | tctgatccca | 1020 |
| ccggccgaag | ccgctcgcct | ggccaaaagc | ctgcctaact | gcaaggctgt | ggacatcggc | 1080 |
| ccgggtctga | atctgctgca | agaagacaac | ccggacctga | tcggcagcga | gatcgcgcgc | 1140 |
| tggctgtcga | cgctcgagat | tccggcgag | ccaaccactg | gaggcagcgg | cggaacagga | 1200 |
| ggctccggcg | gcaccggagg | atccatggca | gaaatcggta | ctggctttcc | attcgacccc | 1260 |
| cattatgtgg | aagtcctggg | cgagcgcatg | cactacgtcg | atgttggtcc | gcgcgatggc | 1320 |
| accctgtgc | tgttcctgca | cggtaacccg | acctcctcct | acgtgtggcg | caacatcatc | 1380 |
| ccgcatgttg | caccgaccca | tcgctgcatt | gctccagacc | tgatcggtat | gggcaaatcc | 1440 |
| gacaaaccag | acctgggtta | tttcttcgac | gaccacgtcc | gcttcatgga | tgccttcatc | 1500 |
| gaagccctgg | gtctggaaga | ggtcgtcctg | gtcattcacg | actggggctc | cgctctgggt | 1560 |
| ttccactggg | ccaagcgcaa | tccagagcgc | gtcaaaggta | ttgcatttat | ggagttcatc | 1620 |
| cgccctatcc | cgacctggga | cgaatggcca | taa | | | 1653 |

<210> SEQ ID NO 28
<211> LENGTH: 550
<212> TYPE: PRT
<213> ORGANISM: Artificial
<220> FEATURE:
<223> OTHER INFORMATION: CiVSD-cpHaloTag Ligand

<400> SEQUENCE: 28

```
Met Glu Gly Phe Asp Gly Ser Asp Phe Ser Pro Pro Ala Asp Leu Val
1               5                   10                  15
Gly Val Gly Gly Ala Val Met Arg Asn Val Asp Val Thr Ile Asn
            20                  25                  30
Gly Asp Val Thr Ala Pro Pro Lys Ala Ala Pro Arg Lys Ser Glu Ser
            35                  40                  45
Val Lys Lys Val His Trp Asn Asp Val Asp Gln Gly Pro Ser Glu Lys
50                  55                  60
Pro Glu Thr Arg Gln Glu Arg Ile Asp Ile Pro Glu Ile Ser Gly
65                  70                  75                  80
Leu Trp Trp Gly Glu Asn Glu His Gly Val Gly Gly Arg Met Glu
                85                  90                  95
Ile Pro Thr Thr Gly Val Gly Arg Val Gln Phe Arg Val Arg Ala Val
                100                 105                 110
Ile Asp His Leu Gly Met Arg Ala Phe Gly Val Phe Leu Ile Leu Leu
            115                 120                 125
Asp Ile Ile Leu Met Ile Ile Asp Leu Ser Leu Pro Gly Lys Ser Glu
130                 135                 140
Ser Ser Gln Ser Phe Tyr Asp Gly Leu Ala Leu Ala Leu Ser Cys Tyr
145                 150                 155                 160
Phe Met Leu Asp Leu Gly Leu Arg Ile Phe Ala Tyr Gly Pro Lys Asn
                165                 170                 175
Phe Phe Thr Asn Pro Trp Glu Val Ala Asp Gly Leu Ile Ile Val Val
            180                 185                 190
Thr Phe Val Val Thr Ile Phe Tyr Thr Val Leu Asp Glu Tyr Phe Gln
        195                 200                 205
Glu Thr Gly Ala Asp Gly Leu Gly Gln Leu Val Val Leu Ala Arg Leu
210                 215                 220
Leu Arg Val Val Arg Leu Ala Arg Ile Phe Tyr Ser His Gln Gln Thr
225                 230                 235                 240
Phe Gln Ala Phe Arg Thr Thr Asp Val Gly Arg Lys Leu Ile Ile Asp
                245                 250                 255
Gln Asn Val Phe Ile Glu Gly Thr Leu Pro Met Gly Val Val Arg Pro
            260                 265                 270
Leu Thr Glu Val Glu Met Asp His Tyr Arg Glu Pro Phe Leu Asn Pro
275                 280                 285
Val Asp Arg Glu Pro Leu Trp Arg Phe Pro Asn Glu Leu Pro Ile Ala
290                 295                 300
Gly Glu Pro Ala Asn Ile Val Ala Leu Val Glu Glu Tyr Met Asp Trp
305                 310                 315                 320
Leu His Gln Ser Pro Val Pro Lys Leu Leu Phe Trp Gly Thr Pro Gly
                325                 330                 335
Val Leu Ile Pro Pro Ala Glu Ala Ala Arg Leu Ala Lys Ser Leu Pro
            340                 345                 350
Asn Cys Lys Ala Val Asp Ile Gly Pro Gly Leu Asn Leu Leu Gln Glu
        355                 360                 365
Asp Asn Pro Asp Leu Ile Gly Ser Glu Ile Ala Arg Trp Leu Ser Thr
370                 375                 380
Leu Glu Ile Ser Gly Glu Pro Thr Thr Gly Ser Gly Gly Thr Gly
385                 390                 395                 400
Gly Ser Gly Gly Thr Gly Gly Ser Met Ala Glu Ile Gly Thr Gly Phe
                405                 410                 415
```

```
Pro Phe Asp Pro His Tyr Val Glu Val Leu Gly Glu Arg Met His Tyr
            420                 425                 430

Val Asp Val Gly Pro Arg Asp Gly Thr Pro Val Leu Phe Leu His Gly
        435                 440                 445

Asn Pro Thr Ser Ser Tyr Val Trp Arg Asn Ile Ile Pro His Val Ala
    450                 455                 460

Pro Thr His Arg Cys Ile Ala Pro Asp Leu Ile Gly Met Gly Lys Ser
465                 470                 475                 480

Asp Lys Pro Asp Leu Gly Tyr Phe Phe Asp Asp His Val Arg Phe Met
                485                 490                 495

Asp Ala Phe Ile Glu Ala Leu Gly Leu Glu Val Val Leu Val Ile
            500                 505                 510

His Asp Trp Gly Ser Ala Leu Gly Phe His Trp Ala Lys Arg Asn Pro
        515                 520                 525

Glu Arg Val Lys Gly Ile Ala Phe Met Glu Phe Ile Arg Pro Ile Pro
    530                 535                 540

Thr Trp Asp Glu Trp Pro
545                 550

<210> SEQ ID NO 29
<211> LENGTH: 1434
<212> TYPE: DNA
<213> ORGANISM: Artificial
<220> FEATURE:
<223> OTHER INFORMATION: DrVSD-HaloTag Ligand

<400> SEQUENCE: 29
atggagacgt ctgtgcattt taaccctggg ttagattcca agaagttaa tggtaattcg        60 gtgaaagaag aggcagaggt gcagatcgat gatggaaagg aagaaaccaa agacccagac      120
acaatgtacc atcaggtccg gaaaaagata actccttttg tgatgtcctt tggttttcgt      180 gttttttggcc tggtactgat catcttggac atcattatgg tcattgtgga cttgtctctt      240
tctgagaaga gtcgtgatgt tggaggtgca ccggagactg tttctctggt catctctttc      300
ttttttctca tcgatgtatt gctccgtgtt tatgtggagg gattcaaggt gtatttcagc      360
tcaaaactga atatagtaga tgcttgtatt gtggtcatta ctctggtggt caccatgatc      420
tacgcattct ccgatttctc aggagccagt ctgattcccc aggtggtgac attcctgagg      480
tctctgagga tcctaattct ggtacgcatc ttcagactgg cctcgcaggg agatcccatc      540
ggtactggct ttccattcga ccccattat gtggaagtcc tgggcgagcg catgcactac      600
gtcgatgttg gtccgcgcga tggcaccct gtgctgttcc tgcacggtaa cccgacctcc      660
tcctacgtgt ggcgcaacat catcccgcat gttgcaccga cccatcgctg cattgctcca      720
gacctgatcg gtatgggcaa atccgacaaa ccagacctgg ttatttcttc gacgaccac     780 gtccgcttca tggatgcctt catcgaagcc ctgggtctgg aagaggtcgt cctggtcatt      840
cacgactggg gctccgctct gggtttccac tgggccaagc gcaatccaga gcgcgtcaaa      900
ggtattgcat ttatggagtt catccgccct atcccgacct gggacgaatg gccagaattt      960
gcccgcgaga ccttccaggc cttccgcacc accgacgtcg ccgcaagct gatcatcgat     1020 cagaacgttt ttatcgaggg tacgctgccg atgggtgtcg tccgcccgct gactgaagtc     1080
gagatggacc attaccgcga gccgttcctg aatcctgttg accgcgagcc actgtggcgc     1140
ttcccaaacg agctgccaat cgccggtgag ccagcgaaca tcgtcgcgct ggtcgaagaa     1200
tacatggact ggctgcacca gtcccctgtc ccgaagctgc tgttctgggg cacccccagc     1260
```

-continued

```
gttctgatcc caccggccga agccgctcgc ctggccaaaa gcctgcctaa ctgcaaggct    1320
gtggacatcg cccgggtct gaatctgctg caagaagaca acccggacct gatcggcagc    1380
gagatcgcgc gctggctgtc gacgctcgag atttccggcg agccaaccac ttaa         1434
```

<210> SEQ ID NO 30
<211> LENGTH: 477
<212> TYPE: PRT
<213> ORGANISM: Artificial
<220> FEATURE:
<223> OTHER INFORMATION: DrVSD-HaloTag Ligand

<400> SEQUENCE: 30

```
Met Glu Thr Ser Val His Phe Asn Pro Gly Leu Asp Ser Lys Glu Val
1               5                   10                  15

Asn Gly Asn Ser Val Lys Glu Glu Ala Glu Val Gln Ile Asp Asp Gly
            20                  25                  30

Lys Glu Glu Thr Lys Asp Pro Asp Thr Met Tyr His Gln Val Arg Lys
        35                  40                  45

Lys Ile Thr Pro Phe Val Met Ser Phe Gly Phe Arg Val Phe Gly Leu
    50                  55                  60

Val Leu Ile Ile Leu Asp Ile Ile Met Val Ile Val Asp Leu Ser Leu
65                  70                  75                  80

Ser Glu Lys Ser Arg Asp Val Gly Gly Ala Pro Glu Thr Val Ser Leu
                85                  90                  95

Val Ile Ser Phe Phe Leu Ile Asp Val Leu Leu Arg Val Tyr Val
            100                 105                 110

Glu Gly Phe Lys Val Tyr Phe Ser Ser Lys Leu Asn Ile Val Asp Ala
        115                 120                 125

Cys Ile Val Val Ile Thr Leu Val Val Thr Met Ile Tyr Ala Phe Ser
    130                 135                 140

Asp Phe Ser Gly Ala Ser Leu Ile Pro Gln Val Val Thr Phe Leu Arg
145                 150                 155                 160

Ser Leu Arg Ile Leu Ile Leu Val Arg Ile Phe Arg Leu Ala Ser Gln
                165                 170                 175

Gly Asp Pro Ile Gly Thr Gly Phe Pro Phe Asp Pro His Tyr Val Glu
            180                 185                 190

Val Leu Gly Glu Arg Met His Tyr Val Asp Val Gly Pro Arg Asp Gly
        195                 200                 205

Thr Pro Val Leu Phe Leu His Gly Asn Pro Thr Ser Ser Tyr Val Trp
    210                 215                 220

Arg Asn Ile Ile Pro His Val Ala Pro Thr His Arg Cys Ile Ala Pro
225                 230                 235                 240

Asp Leu Ile Gly Met Gly Lys Ser Asp Lys Pro Asp Leu Gly Tyr Phe
                245                 250                 255

Phe Asp Asp His Val Arg Phe Met Asp Ala Phe Ile Glu Ala Leu Gly
            260                 265                 270

Leu Glu Glu Val Val Leu Val Ile His Asp Trp Gly Ser Ala Leu Gly
        275                 280                 285

Phe His Trp Ala Lys Arg Asn Pro Glu Arg Val Lys Gly Ile Ala Phe
    290                 295                 300

Met Glu Phe Ile Arg Pro Ile Pro Thr Trp Asp Glu Trp Pro Glu Phe
305                 310                 315                 320

Ala Arg Glu Thr Phe Gln Ala Phe Arg Thr Thr Asp Val Gly Arg Lys
                325                 330                 335
```

```
Leu Ile Ile Asp Gln Asn Val Phe Ile Glu Gly Thr Leu Pro Met Gly
                340                 345                 350

Val Val Arg Pro Leu Thr Glu Val Glu Met Asp His Tyr Arg Glu Pro
            355                 360                 365

Phe Leu Asn Pro Val Asp Arg Glu Pro Leu Trp Arg Phe Pro Asn Glu
    370                 375                 380

Leu Pro Ile Ala Gly Glu Pro Ala Asn Ile Val Ala Leu Val Glu Glu
385                 390                 395                 400

Tyr Met Asp Trp Leu His Gln Ser Pro Val Pro Lys Leu Leu Phe Trp
                405                 410                 415

Gly Thr Pro Gly Val Leu Ile Pro Pro Ala Glu Ala Ala Arg Leu Ala
            420                 425                 430

Lys Ser Leu Pro Asn Cys Lys Ala Val Asp Ile Gly Pro Gly Leu Asn
                435                 440                 445

Leu Leu Gln Glu Asp Asn Pro Asp Leu Ile Gly Ser Glu Ile Ala Arg
    450                 455                 460

Trp Leu Ser Thr Leu Glu Ile Ser Gly Glu Pro Thr Thr
465                 470                 475
```

<210> SEQ ID NO 31
<211> LENGTH: 1434
<212> TYPE: DNA
<213> ORGANISM: Artificial
<220> FEATURE:
<223> OTHER INFORMATION: GgVSD-HaloTag Ligand

<400> SEQUENCE: 31

```
atggagacga ctgtgaggta tgaacagggg tcagagctca ctaaaacttc gagctctcca      60
acagcagatg agcccacgat aaagattgat gatggtcgtg atgagggtaa tgaacaagac     120
agctgttcca ataccattag agaaaaaatt ccccgtttg tgatgtcatt tggattcaga     180
gtatttggag ttgtgcttat cattgtagac atcatagtgg tgattgtgga tctggccatc     240
agtgagaaga aaagaggcat tagagagatt cttgaaggtg tttccctggc tatagcactc     300
ttcttccttg ttgatgttct catgagagtg tttgttgaag gcttcaagaa ctatttccgg     360
tccaaactga atactttgga tgcagtcata gtagtgggca ctctgctaat taatatgacc     420
tactccttct ctgaccttgc tgccacagat cagatgccgc agatggttac tcttcttcga     480
gttctgagaa ttgttatctt aataagaata tttcgcctgg cttcacaggg ggatcccatc     540
ggtactggct ttccattcga cccccattat gtggaagtcc tgggcgagcg catgcactac     600
gtcgatgttg gtccgcgcga tggcaccct gtgctgttcc tgcacggtaa cccgacctcc     660
tcctacgtgt ggcgcaacat catcccgcat gttgcaccga cccatcgctg cattgctcca     720
gacctgatcg gtatgggcaa atccgacaaa ccagacctgg ttatttcttc gacgaccac     780
gtccgcttca tggatgcctt catcgaagcc ctgggtctgg aagaggtcgt cctggtcatt     840
cacgactggg gctccgctct gggtttccac tgggccaagc gcaatccaga gcgcgtcaaa     900
ggtattgcat ttatggagtt catccgccct atcccgacct gggacgaatg ccagaatttt     960
gcccgcgaga ccttccaggc cttcgcacc accgacgtcg gccgcaagct gatcatcgat    1020
cagaacgttt ttatcgaggg tacgctgccg atgggtgtcg tccgcccgct gactgaagtc    1080
gagatggacc attaccgcga gccgttcctg aatcctgttg accgcgagcc actgtggcgc    1140
ttcccaaacg agctgccaat cgccggtgag ccagcgaaca tcgtcgcgct ggtcgaagaa    1200
tacatggact ggctgcacca gtcccctgtc ccgaagctgc tgttctgggg cacccccaggc    1260
```

```
gttctgatcc caccggccga agccgctcgc ctggccaaaa gcctgcctaa ctgcaaggct    1320
gtggacatcg ccccgggtct gaatctgctg caagaagaca cccgcgacct gatcggcagc    1380
gagatcgcgc gctggctgtc gacgctcgag atttccggcg agccaaccac ttaa          1434
```

```
<210> SEQ ID NO 32
<211> LENGTH: 477
<212> TYPE: PRT
<213> ORGANISM: Artificial
<220> FEATURE:
<223> OTHER INFORMATION: GgVSD-HaloTag Ligand

<400> SEQUENCE: 32
```

| Met | Glu | Thr | Thr | Val | Arg | Tyr | Glu | Gln | Gly | Ser | Glu | Leu | Thr | Lys | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Ser Ser Pro Thr Ala Asp Glu Pro Thr Ile Lys Ile Asp Asp Gly
            20                  25                  30

Arg Asp Glu Gly Asn Glu Gln Asp Ser Cys Ser Asn Thr Ile Arg Arg
        35                  40                  45

Lys Ile Ser Pro Phe Val Met Ser Phe Gly Phe Arg Val Phe Gly Val
50                  55                  60

Val Leu Ile Ile Val Asp Ile Ile Val Ile Val Asp Leu Ala Ile
65                  70                  75                  80

Ser Glu Lys Lys Arg Gly Ile Arg Glu Ile Leu Glu Gly Val Ser Leu
                85                  90                  95

Ala Ile Ala Leu Phe Phe Leu Val Asp Val Leu Met Arg Val Phe Val
            100                 105                 110

Glu Gly Phe Lys Asn Tyr Phe Arg Ser Lys Leu Asn Thr Leu Asp Ala
        115                 120                 125

Val Ile Val Val Gly Thr Leu Leu Ile Asn Met Thr Tyr Ser Phe Ser
130                 135                 140

Asp Leu Ala Ala Thr Asp Gln Met Pro Gln Met Val Thr Leu Leu Arg
145                 150                 155                 160

Val Leu Arg Ile Val Ile Leu Ile Arg Ile Phe Arg Leu Ala Ser Gln
                165                 170                 175

Gly Asp Pro Ile Gly Thr Gly Phe Pro Phe Asp Pro His Tyr Val Glu
            180                 185                 190

Val Leu Gly Glu Arg Met His Tyr Val Asp Val Gly Pro Arg Asp Gly
        195                 200                 205

Thr Pro Val Leu Phe Leu His Gly Asn Pro Thr Ser Ser Tyr Val Trp
210                 215                 220

Arg Asn Ile Ile Pro His Val Ala Pro Thr His Arg Cys Ile Ala Pro
225                 230                 235                 240

Asp Leu Ile Gly Met Gly Lys Ser Asp Lys Pro Asp Leu Gly Tyr Phe
                245                 250                 255

Phe Asp Asp His Val Arg Phe Met Asp Ala Phe Ile Glu Ala Leu Gly
            260                 265                 270

Leu Glu Glu Val Val Leu Val Ile His Asp Trp Gly Ser Ala Leu Gly
        275                 280                 285

Phe His Trp Ala Lys Arg Asn Pro Glu Arg Val Lys Gly Ile Ala Phe
290                 295                 300

Met Glu Phe Ile Arg Pro Ile Pro Thr Trp Asp Glu Trp Pro Glu Phe
305                 310                 315                 320

Ala Arg Glu Thr Phe Gln Ala Phe Arg Thr Thr Asp Val Gly Arg Lys
                325                 330                 335

```
Leu Ile Ile Asp Gln Asn Val Phe Ile Glu Gly Thr Leu Pro Met Gly
            340             345             350

Val Val Arg Pro Leu Thr Glu Val Glu Met Asp His Tyr Arg Glu Pro
        355             360             365

Phe Leu Asn Pro Val Asp Arg Glu Pro Leu Trp Arg Phe Pro Asn Glu
    370             375             380

Leu Pro Ile Ala Gly Glu Pro Ala Asn Ile Val Ala Leu Val Glu Glu
385             390             395             400

Tyr Met Asp Trp Leu His Gln Ser Pro Val Pro Lys Leu Leu Phe Trp
            405             410             415

Gly Thr Pro Gly Val Leu Ile Pro Pro Ala Glu Ala Ala Arg Leu Ala
        420             425             430

Lys Ser Leu Pro Asn Cys Lys Ala Val Asp Ile Gly Pro Gly Leu Asn
        435             440             445

Leu Leu Gln Glu Asp Asn Pro Asp Leu Ile Gly Ser Glu Ile Ala Arg
        450             455             460

Trp Leu Ser Thr Leu Glu Ile Ser Gly Glu Pro Thr Thr
465             470             475
```

CHEMIGENETIC VOLTAGE INDICATORS

RELATED APPLICATIONS

This application claims the benefit of U.S. Provisional Application Ser. No. 62/428,066, filed Nov. 30, 2016, the entire disclosure of which is incorporated herein by this reference.

SEQUENCE LISTING

This application contains a Sequence Listing which has been submitted in ASCII format via EFS-Web and is hereby incorporated by reference in its entirety. The ASCII copy of the Sequence Listing, which was created on Nov. 30, 2017, is named 18074N-16049.txt and is 112 kilobytes in size.

TECHNICAL FIELD

The presently-disclosed subject matter generally relates to voltage indicators and methods of use thereof. More specifically, the presently-disclosed subject matter relates to chemigenetic voltage indicators and methods of measuring voltage using chemigenetic voltage indicators.

BACKGROUND

Optical imaging of membrane potential allows direct visualization of the rapid electrical signals that neurons use to communicate. Because electrical signals in neurons are fast, current optical methods are limited by the number of photons that can be collected by an imaging camera for each image of a movie.[1] Therefore, voltage indicators that emit more photons during each image, and that do so over more images before irreversible photobleaching occurs, produce qualitative improvements in the accuracy and duration of voltage measurements.

The current collection of small-molecule voltage indicator dyes are bright and produce large changes in fluorescence with changes in cell membrane potential. However, they cannot easily be targeted to specific neurons, which limits their in vivo utility because all cell membranes are stained with the dye and no individual neurons can be seen clearly. Conversely, protein-based indicators (genetically encoded voltage indicators, GEVIs) can be targeted to individual neurons or specific populations of neurons, but have limited brightness and photostability.

Accordingly, there remains a need for targeted voltage indicators that produce increased brightness and photostability.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to a voltage indicator. In some embodiments, the voltage indicator includes a membrane-localized voltage-sensitive protein coupled to a capture protein. In some embodiments, the capture protein is arranged and disposed to capture small-molecule fluorescent dyes. In one embodiment, the fluorescent dyes include azetidine-containing Janelia Fluor™ dyes. In another embodiment, the Janelia Fluor™ dyes are selected from the group consisting of Janelia Fluor™$_{505}$, Janelia Fluor™$_{525}$, Janelia Fluor™$_{549}$, Janelia Fluor™$_{585}$, Janelia Fluor™$_{646}$, and combinations thereof.

In some embodiments, the voltage sensitive protein is an opsin, such as, but not limited to, a microbial opsin. Suitable microbial opsins include, but are not limited to, QuasAr2, Ace2N, or a combination thereof. In some embodiments, the voltage sensitive protein includes at least one voltage-sensing domain selected from the group consisting of a *Ciona intestinalis* voltage-sensing domain (CiVSD), *Danio rerio* voltage-sensing domain (DrVSD), *Gallus gallus* voltage-sensing domain (GgVSD), and a combination thereof.

In some embodiments, capture protein is a covalent capture protein. In one embodiment, the covalent capture protein is selected from the group consisting of HaloTag®, SNAP-tag®, TMP-tag, βLac-tag, CLIP-tag™, or a combination thereof. In some embodiments, the capture protein is a non-covalent capture protein. In one embodiment, the non-covalent capture protein is selected from the group consisting of TMP-tag, biotin-avidin, and a combination thereof.

In some embodiments, the presently-disclosed subject matter is directed to a method of measuring voltage, the method comprising administering a voltage indicator including a membrane-localized voltage-sensitive protein coupled to a capture protein, and determining changes in fluorescence of a small-molecule fluorescent dye captured by the capture protein. In some embodiments, the changes in fluorescence are observed with a microscope. In some embodiments, the method further comprises determining changes in voltage based upon changes in fluorescence.

In some embodiments, the voltage indicator further comprises a linker between the voltage-sensitive protein and the capture protein. In some embodiments, the method further comprises modifying a length of the linker. In one embodiment, modifying the length of the linker includes removing at least one amino acid residue. In another embodiment, removing at least one amino acid residue includes removing between 1 and 22 amino acid residues. In a further embodiment, modifying the length of the linker modifies the size of a fluorescence response.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 15A-C show graphs and images illustrating fluorescence of rat hippocampal neuron expressing Ace2N-HaloTag labeled with JF$_{585}$. (A) Fluorescence micrograph of rat hippocampal neuron in culture expressing Ace2N-HaloTag labeled with JF$_{585}$. (B) Fluorescence versus voltage for cells like in (A). (C) Fluorescence (top) compared with voltage (bottom, as measured with a whole-cell patch clamp pipette) from neurons like in (A) showing action potential spikes and subthreshold depolarizations.

DESCRIPTION OF EXEMPLARY EMBODIMENTS

Figure 1:
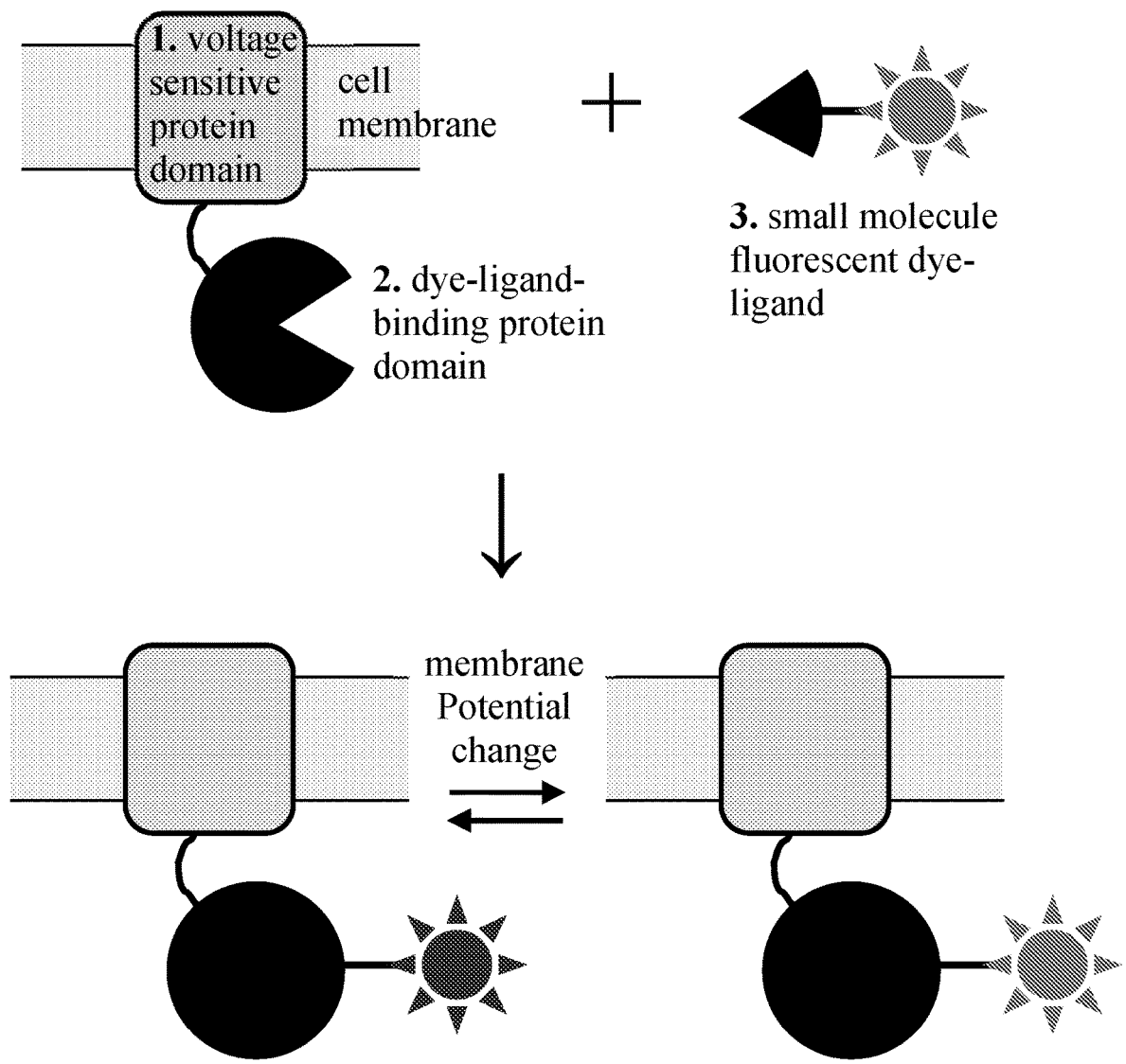
FIG. 1 is a schematic representation of the chemigenetic voltage indicators according to an embodiment of the disclosure.
Figure 2A:
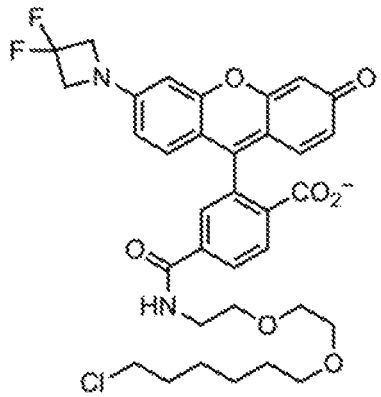
FIGS. 2A-F show chemical structures of various fluorescent dye-ligands according to an embodiment of the disclosure. The structures include JF$_{505}$-HaloTag ligand (FIG. 2A), JF$_{525}$-HaloTag ligand (FIG. 2B), JF$_{549}$-HaloTag ligand (FIG. 2C), JF$_{585}$-HaloTag ligand (FIG. 2D), JF$_{635}$-HaloTag ligand (FIG. 2E), and JF$_{549}$-SNAP-Tag ligand (FIG. 2F).
Figure 2B:
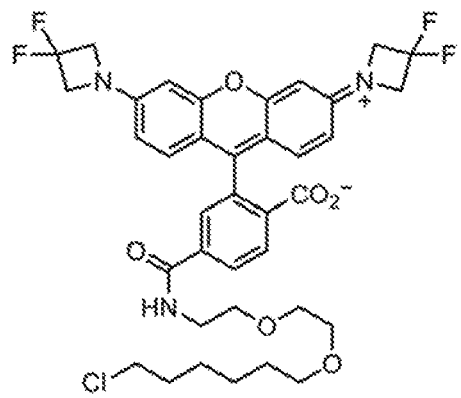
Figure 2C:
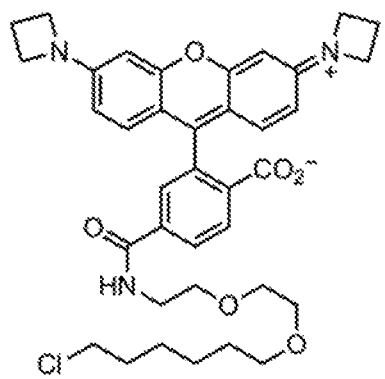
Figure 2D:
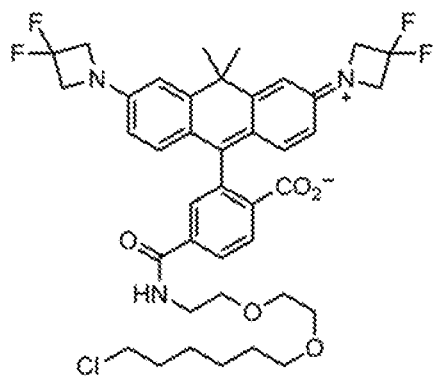
Figure 2E:
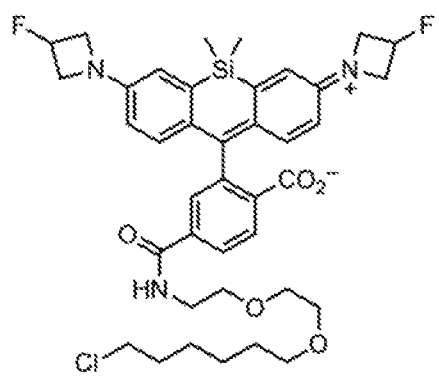
Figure 2F:
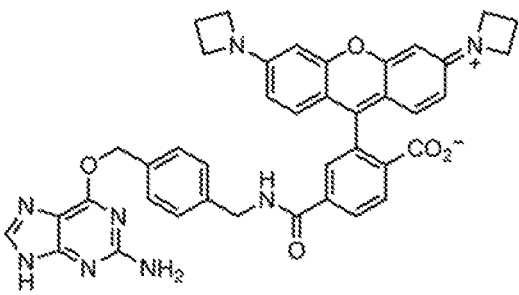

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes voltage indicators and methods of measuring voltage with voltage indicators. In some embodiments, the voltage indicators include membrane-localized voltage-sensitive proteins coupled to enzymes engineered to capture small-molecule fluorescent dyes (FIG. 1). In one embodiment, these voltage indicators combine the brightness and photostability of small-molecule dyes with the genetic targetability of proteins. In another embodiment, these voltage indicators are formed from any suitable combination of dyes, voltage sensitive proteins, and capture proteins. In a further embodiment, the voltage indicators include different inter-domain linker lengths, topological variations, or combinations thereof. The various combinations allow for modulation of fluorescence excitation and emission wavelengths of the dye, kinetics of the covalent capture protein, and kinetics of the voltage sensitive protein.

Suitable small-molecule fluorescent dyes include, but are not limited to, one or more fluorophore dyes. In one embodiment, the fluorophore dye includes a fluorophore containing one or more cyclic amine substituents. In another embodiment, the fluorophore dye includes an azetidine-containing Janelia Fluor™ dye. In a further embodiment, the Janelia Fluor™ dye includes one or more four-membered azetidine rings in place of the ubiquitous dimethylamino groups of existing fluorophores, forming small, cell-permeable fluorophores having increased brightness and photostability. Such Janelia Fluor™ dyes include, but are not limited to, Janelia Fluor™$_{505}$, Janelia Fluor™$_{525}$, Janelia Fluor™$_{549}$, Janelia Fluor™$_{585}$, Janelia Fluor™$_{635}$, and combinations thereof (FIGS. 2A-F).

Suitable voltage sensitive proteins include, but are not limited to, one or more opsins, one or more other molecules including a voltage-sensing domain, or a combination thereof. For example, in one embodiment, the voltage sensitive protein includes a microbial opsin, such as, but not limited to, QuasAr2, Ace2N. In another embodiment, the voltage sensitive protein includes a *Ciona intestinalis* voltage-sensing domain (CiVSD), *Danio rerio* voltage-sensing domain (DrVSD), *Gallus gallus* voltage-sensing domain (GgVSD), or a combination thereof.

Suitable capture proteins include any protein configured to bind a desired ligand. For example, in one embodiment, the capture protein includes a covalent capture protein. In another embodiment, the covalent capture protein includes, but is not limited to, HaloTag (FIGS. 2A-E), SNAP-tag (FIG. 2F), or a combination thereof. Other suitable covalent capture proteins include, but are not limited to, TMP-tag, βLac-tag, CLIP-tag, or a combination thereof. Additionally or alternatively, the capture protein may include a non-covalent capture proteins which capture, or bind, the desired ligand with non-covalent interactions. Suitable non-covalent capture proteins include, but are not limited to, certain TMP-tag, biotin-avidin, or a combination thereof.

The dyes, voltage sensitive proteins, and capture proteins discussed above demonstrate the modularity and generality of the instant voltage indicator design. In some embodiments, this allows for modulation of the fluorescence excitation and emission wavelengths of the dye, the chemical nature of the linker connecting the dye to the capture protein, the kinetics of the capture protein, and/or the kinetics of the voltage sensitive protein. For example, in one embodiment, the voltage sensitive protein QuasAr2 may be combined with the HaloTag or SNAP-tag capture protein, along with any suitable dye. In another embodiment, the voltage sensitive protein Ace2N may be combined with the HaloTag or SNAP-tag capture protein, along with any suitable dye. As will be understood by those of ordinary skill in the art, the dyes, voltage sensitive proteins, and capture proteins discussed above are for illustration only and are not intended to limit the scope of the instant disclosure. Accordingly, voltage indicators including any suitable dye, voltage sensitive protein, and/or capture protein substitute are expressly contemplated herein.

Figure 3A:
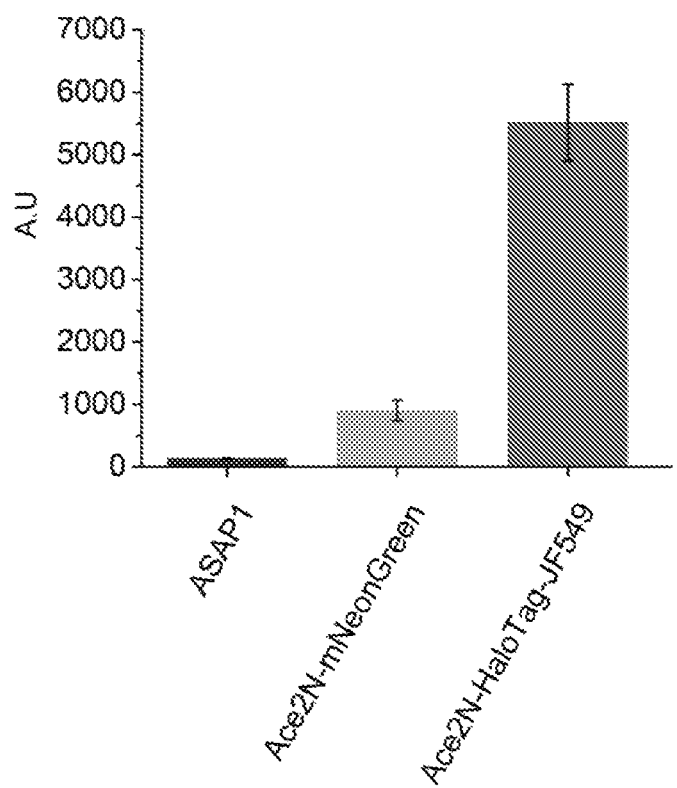
FIGS. 3A-B show graphs comparing fluorescence brightness (A) and fluorescence photobleaching rates (B) of ASAP1, Ace2N-mNeonGreen, and Ace2N-HaloTag-JF$_{549}$ in rat hippocampal neurons in culture.
Figure 3B:
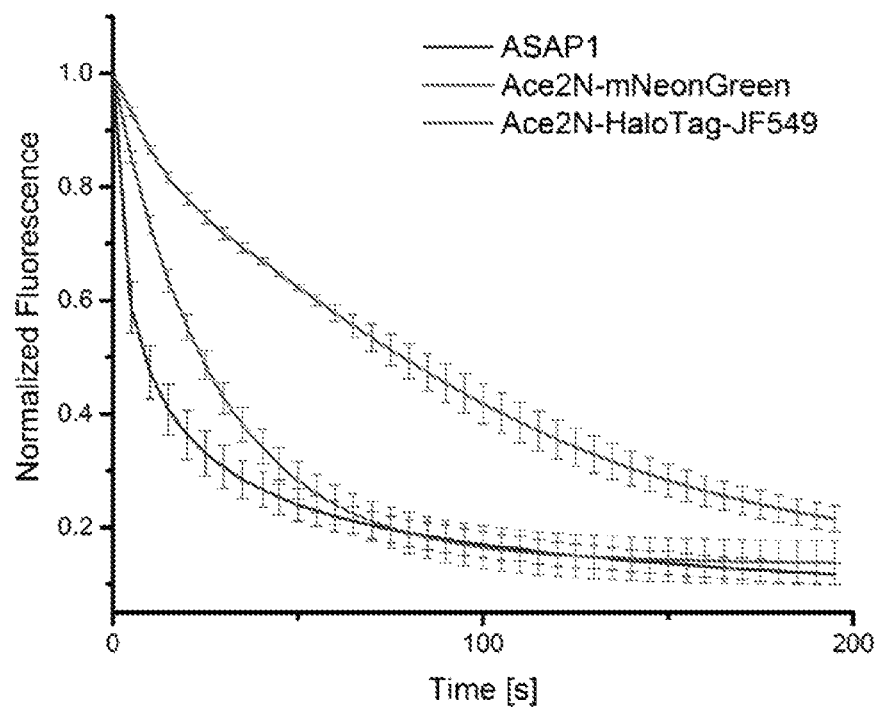

The presently-disclosed subject matter also includes methods of measuring voltage using the voltage indicators. In some embodiments, the methods include administering the voltage indicators and measuring changes in fluorescence of the dye by any suitable method. The changes in fluorescence may be measured through any suitable method such as, but not limited to, observation with a microscope, image capture, video recording, or a combination thereof. In one embodiment, the voltage indicators disclosed herein are substantially brighter and more photostable than existing GEVIs (FIGS. 3A-B). In another embodiment, the amplitude of the indicator response may be increased by shortening or eliminating the linker peptide between the voltage sensitive protein and the covalent capture protein. In further embodiment, shortening the linker peptide includes removing at least one amino acid residue therefrom. As will be appreciated by those skilled in the art, the number of amino acid residues removed may be determined by the desired amplitude and/or the specific linker peptide. In certain embodiments, the number of amino acid residues removed is at least 1, up to all but 1, between 1 and 22, between 2 and 22, 4, 8, 12, 16, 18, 20, 22, or any suitable combination, sub-combination, range, or sub-range thereof.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

The following examples describe properties of various chemigenetic voltage indicators according to the instant disclosure.

Example 1

This example compares the fluorescence response of various QuasAr2-HaloTag voltage indicators having different length linkers connecting QuasAr2 and HaloTag. To form the different lengths, amino acid residues were removed from the linker. A total of 8 voltage indicators with different linker lengths were formed, including QuasAr2-HaloTag (SEQ ID NO: 1 and SEQ ID NO: 2), QuasAr2-HaloTag-4 (SEQ ID NO: 3 and SEQ ID NO: 4), QuasAr2-HaloTag-8 (SEQ ID NO: 5 and SEQ ID NO: 6), QuasAr2-HaloTag-12 (SEQ ID NO: 7 and SEQ ID NO: 8), QuasAr2-HaloTag-16 (SEQ ID NO: 9 and SEQ ID NO: 10), QuasAr2-HaloTag-18 (SEQ ID NO: 11 and SEQ ID NO: 12), QuasAr2-HaloTag-20 (SEQ ID NO: 13 and SEQ ID NO: 14), and QuasAr2-HaloTag-22 (SEQ ID NO: 15 and SEQ ID NO: 16). The number at the end of each voltage indicator reflects the number of amino acid residues that were removed from the linker. For example, QuasAr2-HaloTag-4 is a voltage indicator where 4 amino acid residues were removed from the linker, while QuasAr2-HaloTag-12 is a voltage indicator where 12 amino acid residues were removed from the linker.

Figure 4:
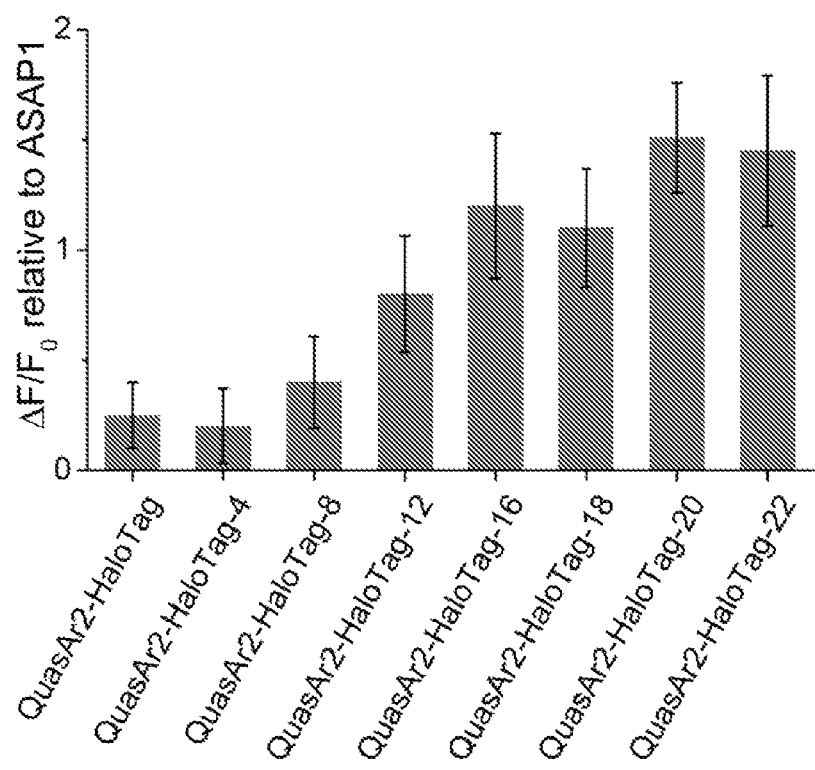
FIG. 4 shows a graph illustrating size of the fluorescence response of QuasAr2-HaloTag voltage indicators with different sized linkers connecting QuasAr2 and HaloTag. Fluorescence response measured relative to ASAP1.

The fluorescence of these voltage indicator was measure relative to ASAP1. As illustrated in FIG. 4, each different linker length provided a different size fluorescence response.

Example 2

Figure 5A:
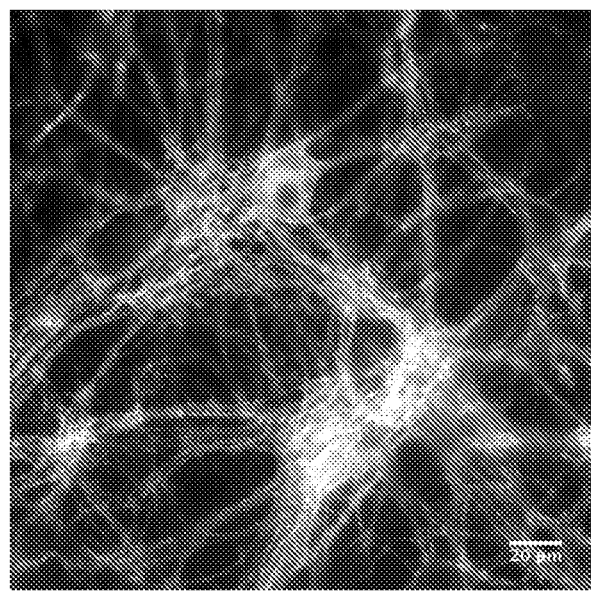
FIGS. 5A-B shows graphs and images illustrating fluorescence of rat hippocampal neurons expressing QuasAr-HaloTag labeled with JF$_{549}$. (A) Fluorescence micrograph of rat hippocampal neurons in culture expressing QuasAr-HaloTag labeled with JF$_{549}$. (B) Fluorescence traces from three regions within the image from (A) showing voltage-dependent fluorescence changes resulting from field electrode-induced depolarization of the neurons.
Figure 5B:
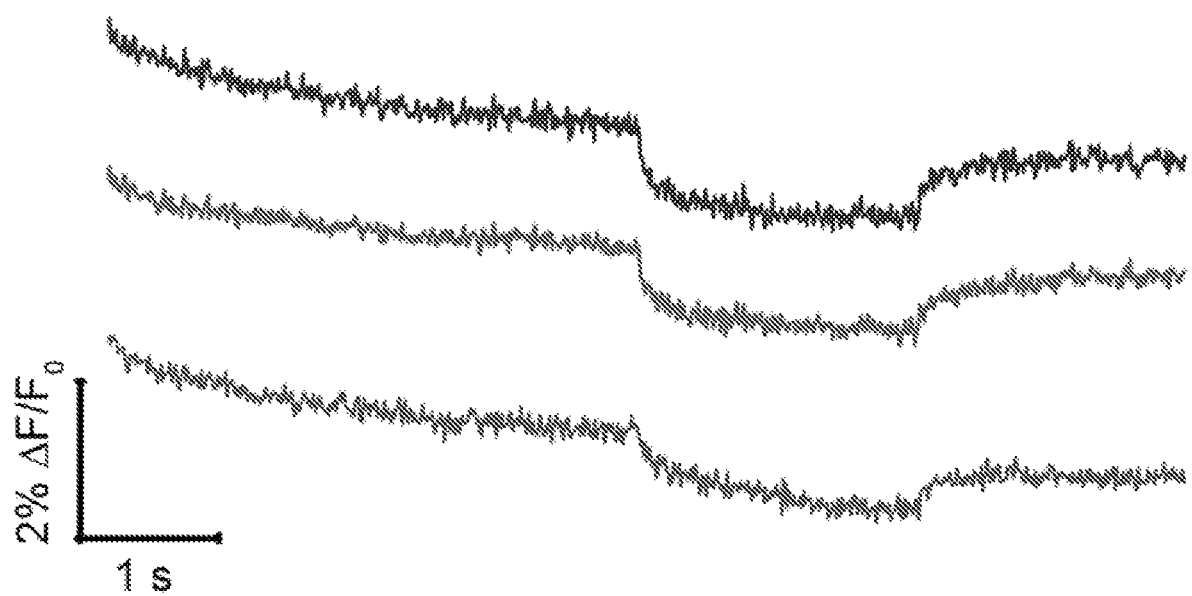
Figure 6A:
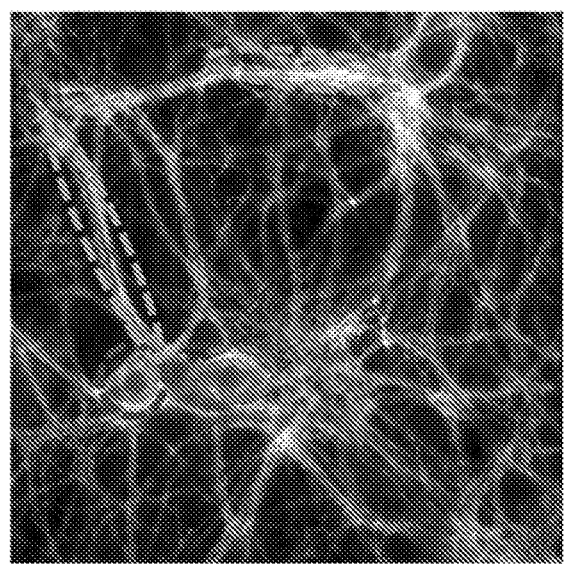
FIGS. 6A-B shows graphs and images illustrating fluorescence of rat hippocampal neurons expressing QuasAr2-HaloTag-16 labeled with JF$_{549}$. (A) Fluorescence micrograph of rat hippocampal neurons in culture expressing QuasAr2-HaloTag-16 labeled with JF$_{549}$. (B) Fluorescence traces from four regions within the image from (A) showing voltage-dependent fluorescence changes resulting from spontaneous action potentials of the neurons.
Figure 6B:
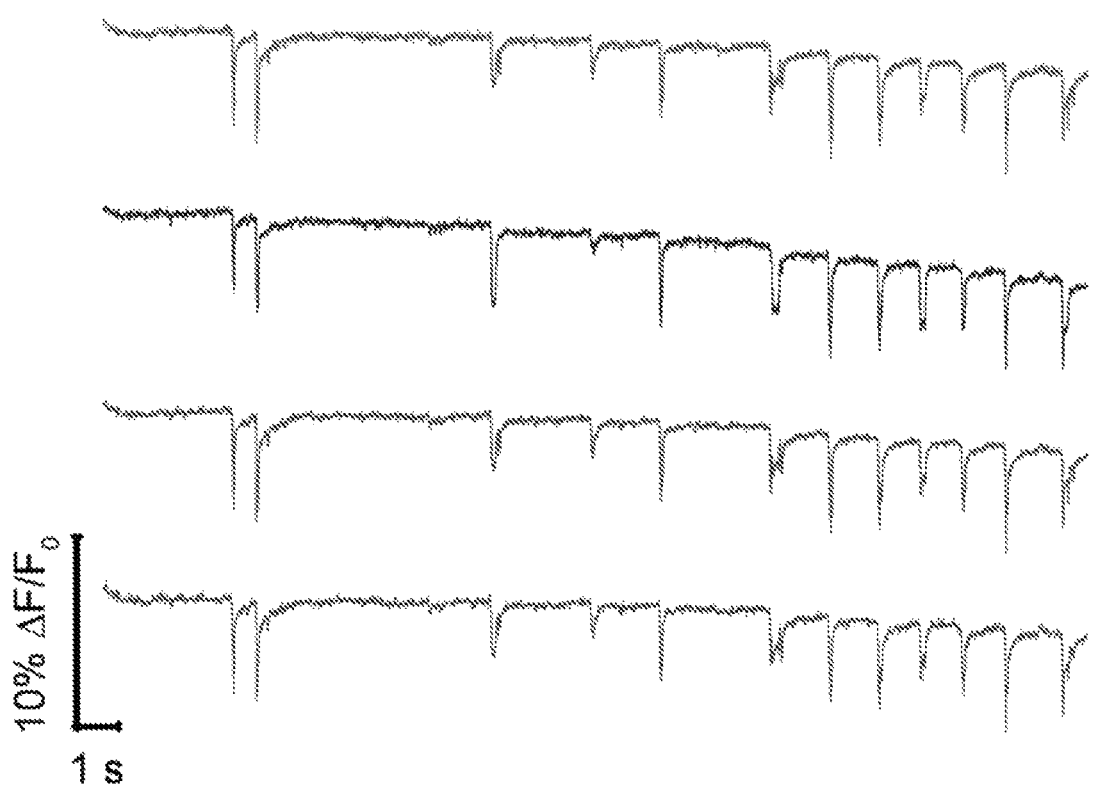
Figure 7A:
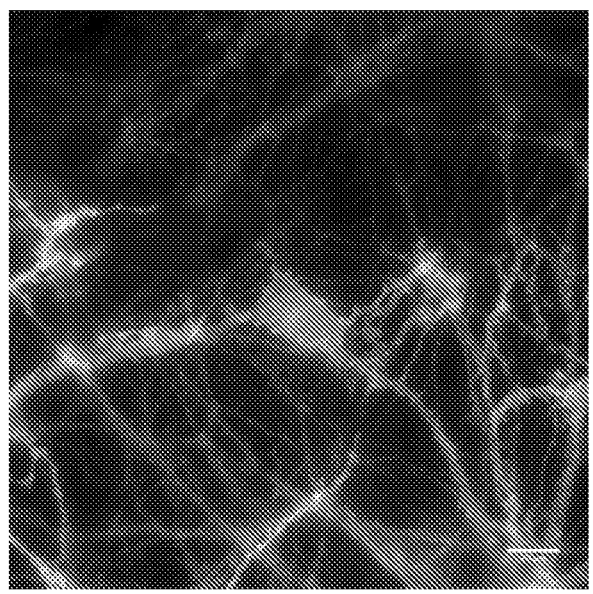
FIGS. 7A-B shows graphs and images illustrating fluorescence of rat hippocampal neurons expressing QuasAr-cpHaloTag labeled with JF$_{549}$. (A) Fluorescence micrograph of rat hippocampal neurons in culture expressing QuasAr-cpHaloTag labeled with JF$_{549}$. (B) Fluorescence traces from three regions within the image from (A) showing voltage-dependent fluorescence changes resulting from field electrode-induced depolarization of the neurons.
Figure 7B:
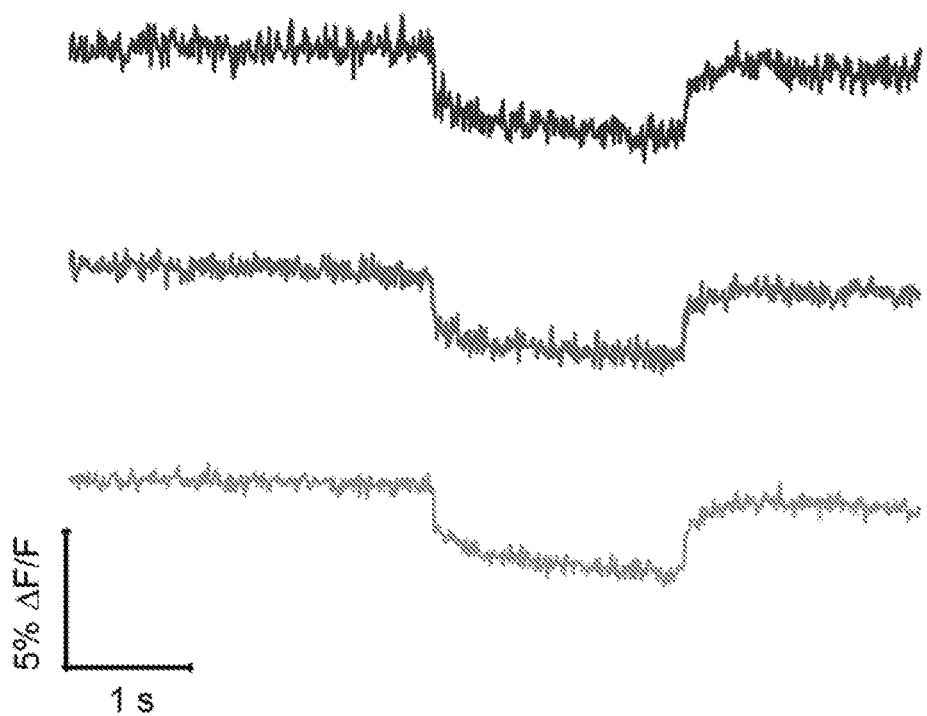
Figure 8A:
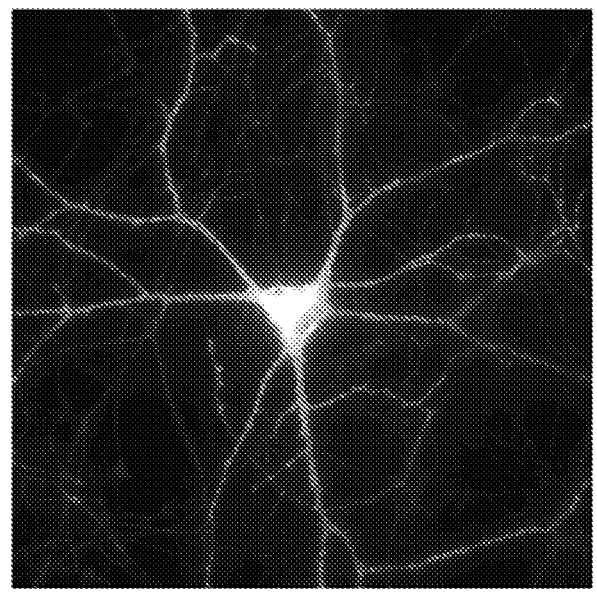
FIGS. 8A-B shows graphs and images illustrating fluorescence of rat hippocampal neurons expressing QuasAr2-SNAP-Tag labeled with JF$_{549}$. (A) Fluorescence micrograph of rat hippocampal neurons in culture expressing QuasAr2-SNAP-Tag labeled with JF$_{549}$. (B) Fluorescence traces from three regions within the image from (A) showing voltage-dependent fluorescence changes resulting from field electrode-induced action potentials of the neurons.
Figure 8B:
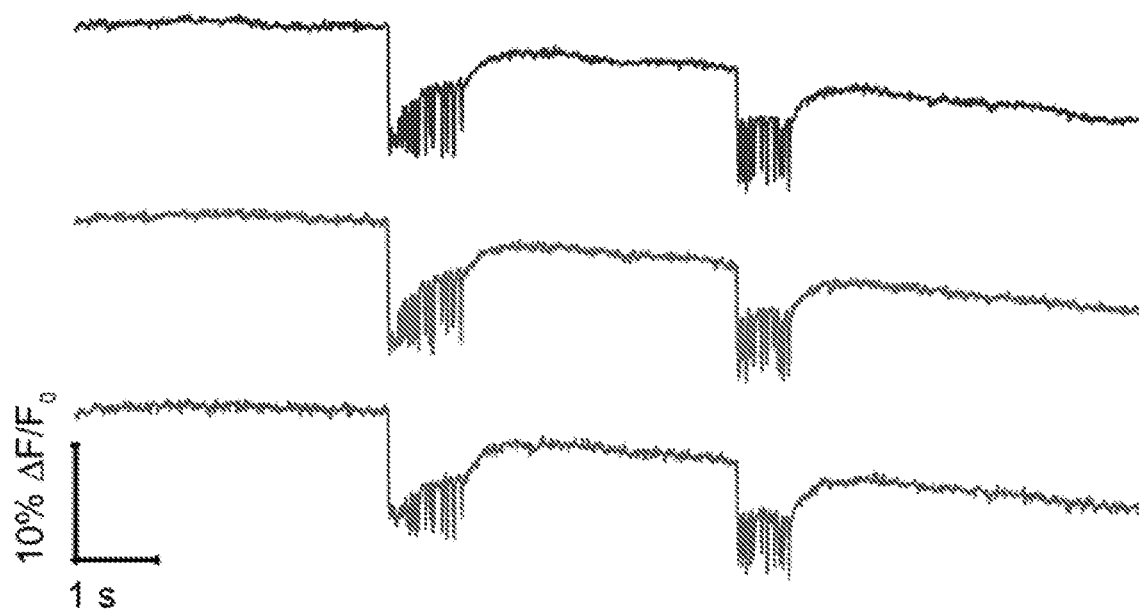
Figure 9A:
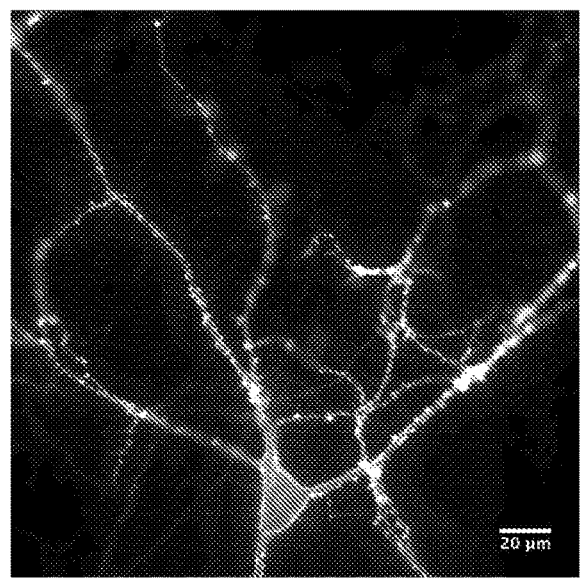
FIGS. 9A-B shows graphs and images illustrating fluorescence of rat hippocampal neurons expressing HaloTag-QuasAr2 labeled with JF$_{549}$. (A) Fluorescence micrograph of rat hippocampal neurons in culture expressing HaloTag-QuasAr2 labeled with JF$_{549}$. (B) Fluorescence traces from one region within the image from (A) showing voltage-dependent fluorescence changes resulting from field electrode-induced depolarization of the neurons.
Figure 9B:
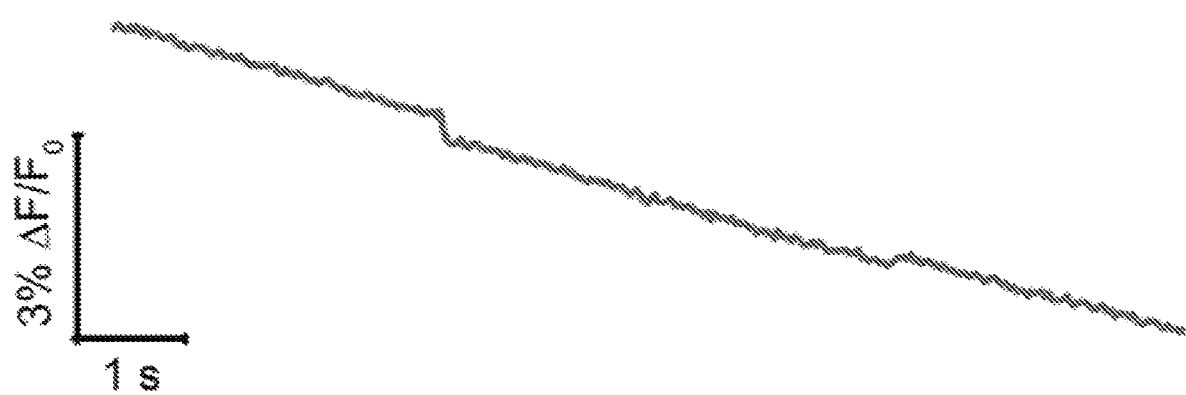
Figure 10A:
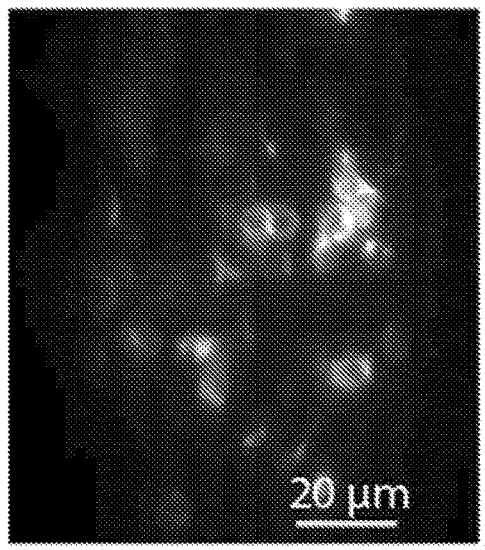
FIGS. 10A-D show graphs and images illustrating in vivo voltage imaging in zebrafish larvae (6 days post-fertilization). (A) Fluorescence micrograph of fluorescence from neurons in the larval zebrafish ventral midbrain expressing Ace2N-HaloTag and labeled with JF$_{525}$. A light sheet microscope with 488 nm excitation was use. (B) Same as (A) except with regions of interest overlayed that correspond to fluorescence traces in (C) and (D). (C) The status of a visual stimulus displayed to the fish and electrophysiological recording showing the fish's intended swimming (top), with fluorescence traces from 12 individual neurons shown in (B). (D) Zoom-in of (C) at the region indicated.
Figure 10B:
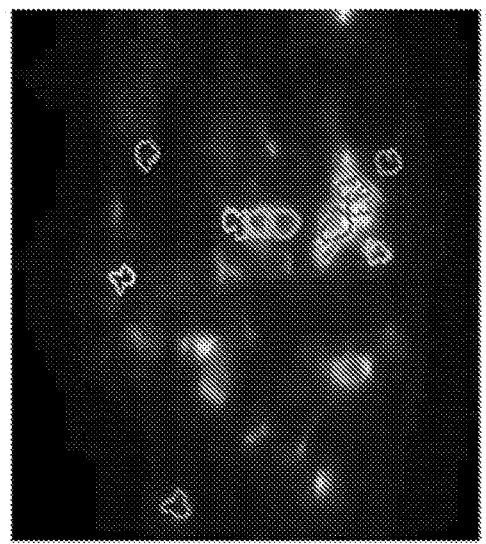
Figure 10C:
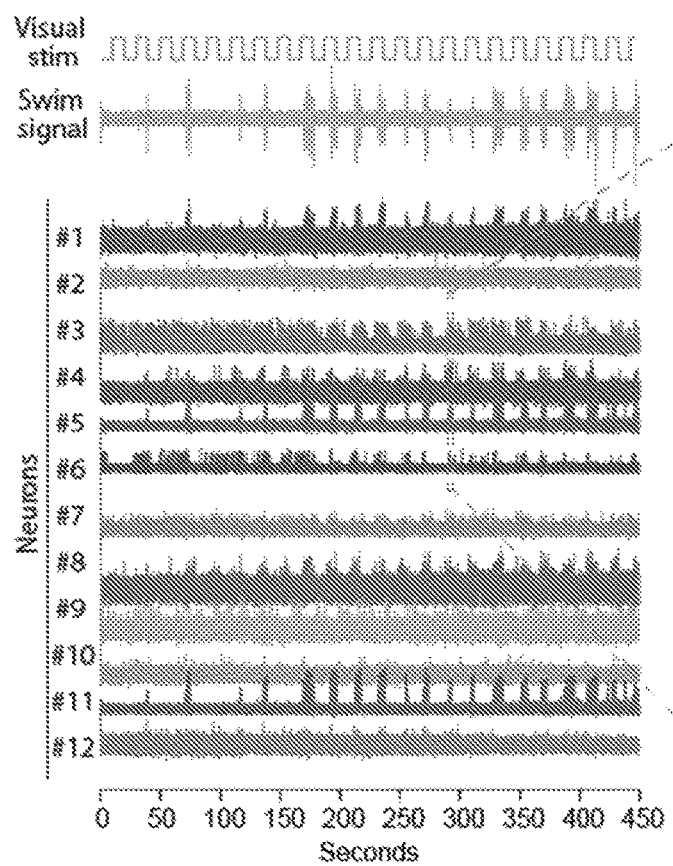
Figure 10D:
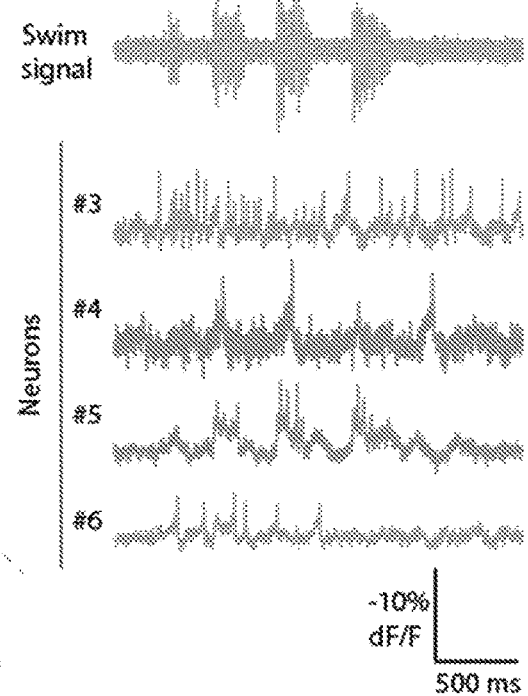

In this example, the fluorescence of various $JF_{549}$ labeled QuasAr2 containing voltage indicators was measured in rat hippocampal neurons in culture. In particular, FIGS. 5A-B show the fluorescence of rat hippocampal neurons expressing QuasAr-HaloTag (SEQ ID NO: 1 and SEQ ID NO: 2) labeled with $JF_{549}$ (FIG. 5A) and voltage-dependent fluorescence changes resulting from field electrode-induced depolarization of the neurons (FIG. 5B). FIGS. 6A-B show the fluorescence of rat hippocampal neurons expressing QuasAr2-HaloTag-16 (SEQ ID NO: 9 and SEQ ID NO: 10) labeled with $JF_{549}$ (FIG. 6A) and voltage-dependent fluorescence changes resulting from spontaneous action potentials of the neurons (FIG. 6B). FIGS. 7A-B show the fluorescence of rat hippocampal neurons expressing QuasAr-cpHaloTag (SEQ ID NO: 17 and SEQ ID NO: 18) labeled with $JF_{549}$ (FIG. 7A) and voltage-dependent fluorescence changes resulting from field electrode-induced depolarization of the neurons (FIG. 7B). FIGS. 8A-B show the fluorescence of rat hippocampal neurons expressing QuasAr2-SNAP-Tag (SEQ ID NO: 19 and SEQ ID NO: 20) labeled with $JF_{549}$ (FIG. 8A) and voltage-dependent fluorescence changes resulting from field electrode-induced depolarization of the neurons (FIG. 8B). FIGS. 9A-B show the fluorescence of rat hippocampal neurons expressing HaloTag-QuasAr2 (SEQ ID NO: 21 and SEQ ID NO: 22)

labeled with JF$_{549}$ (FIG. 9A) and voltage-dependent fluorescence changes resulting from field electrode-induced depolarization of the neurons (FIG. 9B).

Example 3

In this example, the fluorescence of Ace2N-HaloTag (SEQ ID NO: 23 and SEQ ID NO: 24) voltage indicators labeled with various fluorescent dyes was measured. As discussed below, changes in the cell membrane potential produced changes in the fluorescence of the dye when the indicators were tested in cultured rat hippocampal neurons and live zebrafish larvae.

Figure 11:
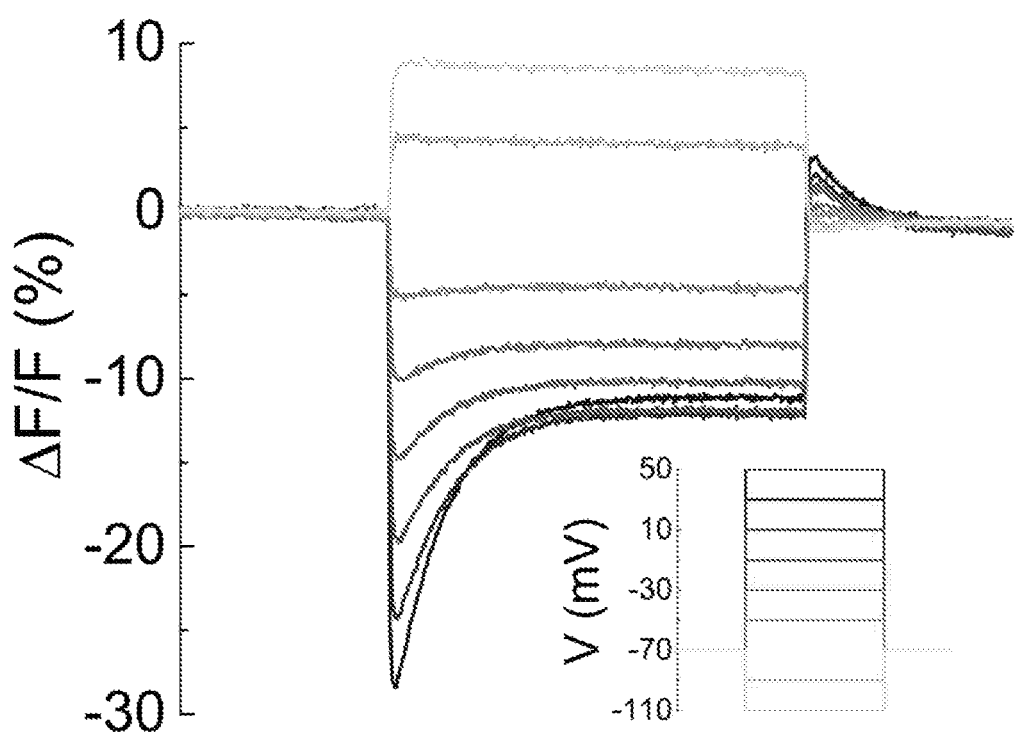
FIG. 11 shows a graph illustrating fluorescence response to voltage steps (inset) of Ace2N-HaloTag labeled with JF$_{525}$ in rat hippocampal neurons in culture.
Figure 12A:
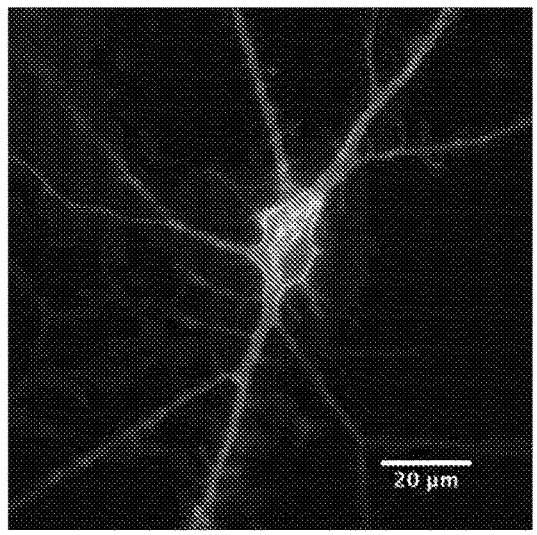
FIGS. 12A-C show graphs and images illustrating fluorescence of rat hippocampal neuron expressing Ace2N-HaloTag labeled with JF$_{505}$. (A) Fluorescence micrograph of rat hippocampal neuron in culture expressing Ace2N-HaloTag labeled with JF$_{505}$. (B) Fluorescence versus voltage for cells like in (A). (C) Fluorescence (top) compared with voltage (bottom, as measured with a whole-cell patch clamp pipette) from neurons like in (A) showing action potential spikes and subthreshold depolarizations.
Figure 12B:
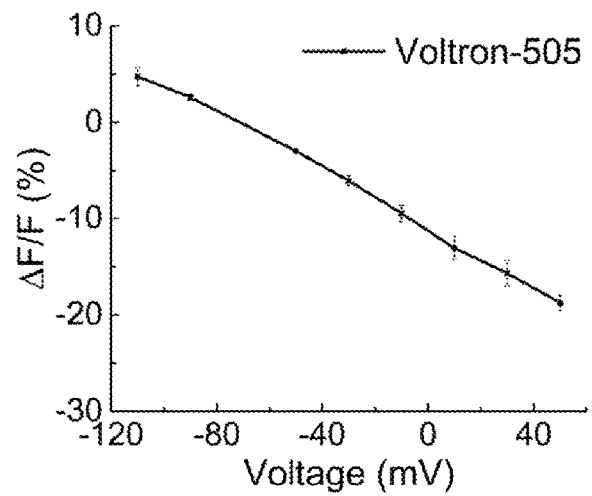
Figure 12C:
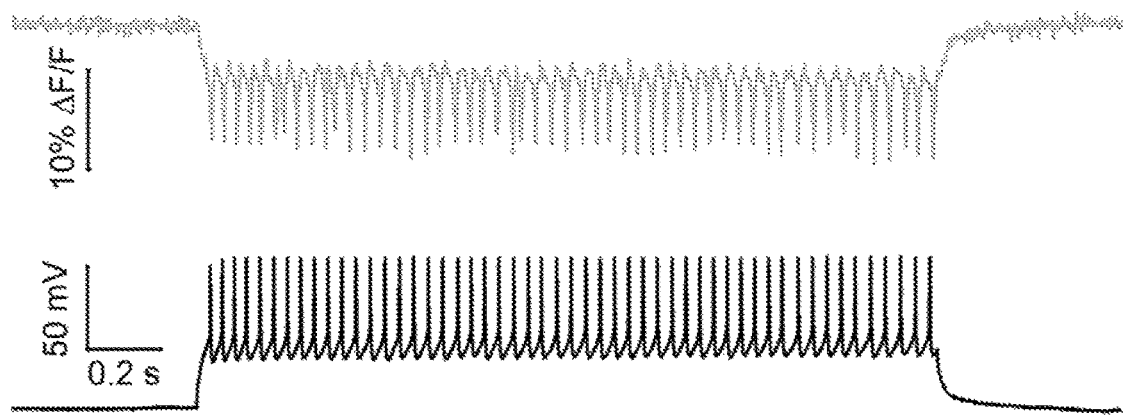
Figure 13A:
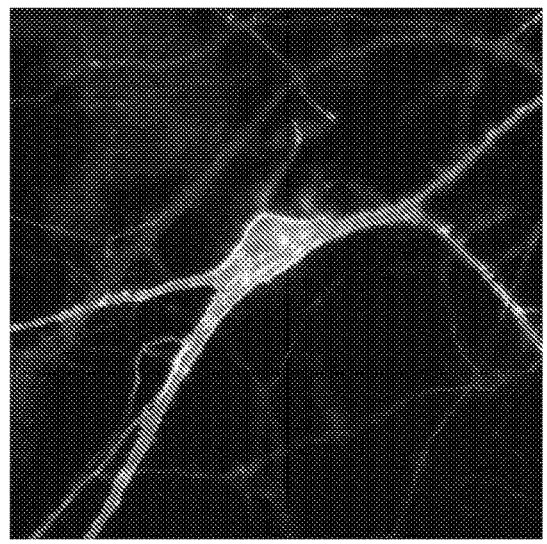
FIGS. 13A-C show graphs and images illustrating fluorescence of rat hippocampal neuron expressing Ace2N-HaloTag labeled with JF$_{525}$. (A) Fluorescence micrograph of rat hippocampal neuron in culture expressing Ace2N-HaloTag labeled with JF$_{525}$. (B) Fluorescence versus voltage for cells like in (A). (C) Fluorescence (top) compared with voltage (bottom, as measured with a whole-cell patch clamp pipette) from neurons like in (A) showing action potential spikes and subthreshold depolarizations.
Figure 13B:
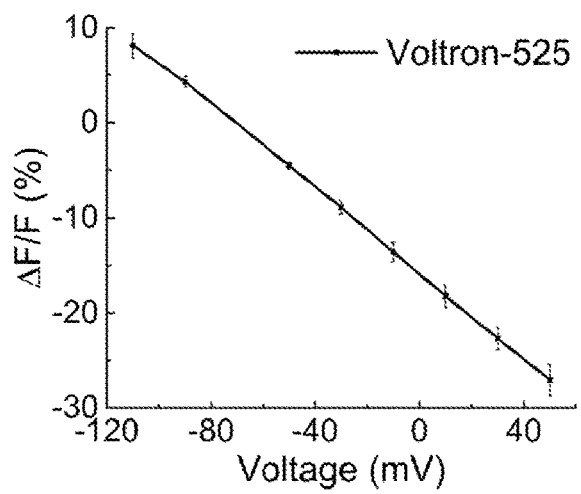
Figure 13C:
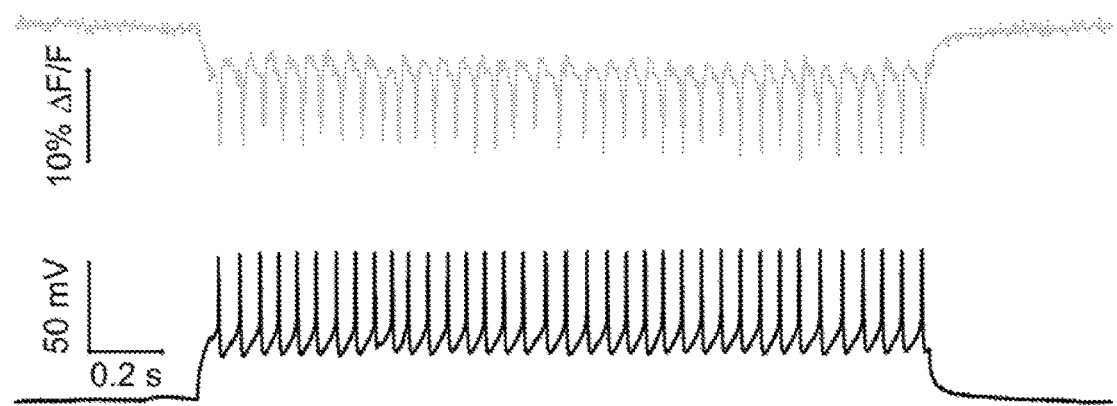
Figure 14A:
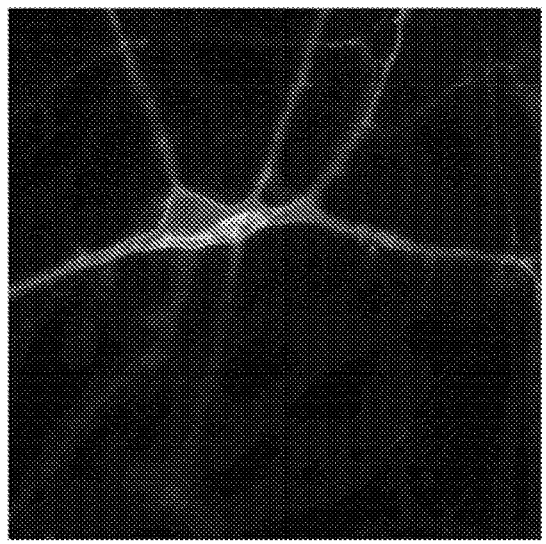
FIGS. 14A-C show graphs and images illustrating fluorescence of rat hippocampal neuron expressing Ace2N-HaloTag labeled with JF$_{549}$. (A) Fluorescence micrograph of rat hippocampal neuron in culture expressing Ace2N-HaloTag labeled with JF$_{549}$. (B) Fluorescence versus voltage for cells like in (A). (C) Fluorescence (top) compared with voltage (bottom, as measured with a whole-cell patch clamp pipette) from neurons like in (A) showing action potential spikes and subthreshold depolarizations.
Figure 14B:
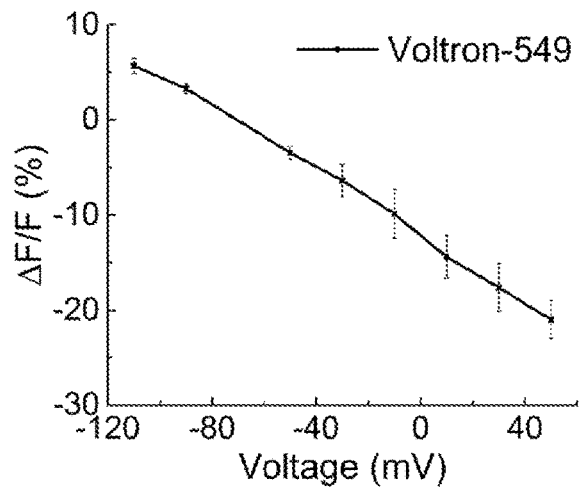
Figure 14C:
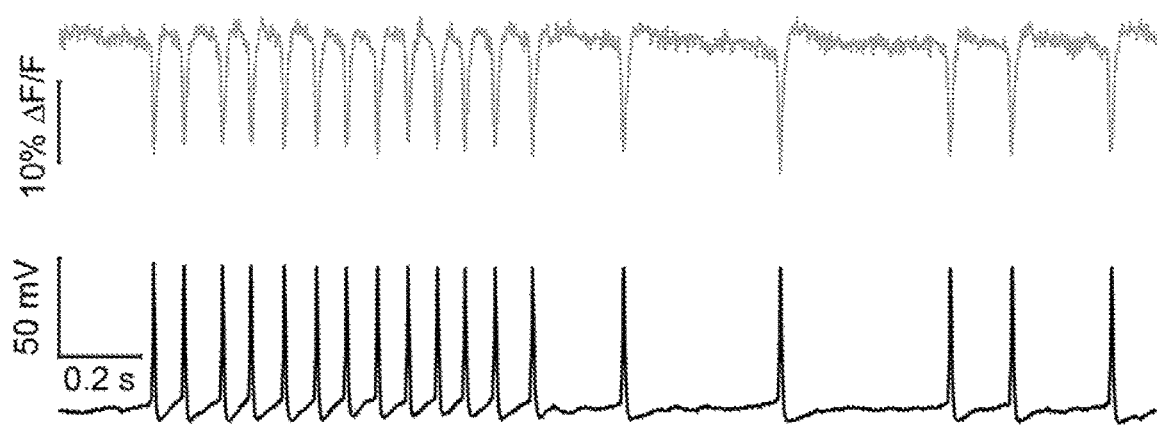
Figure 15C:
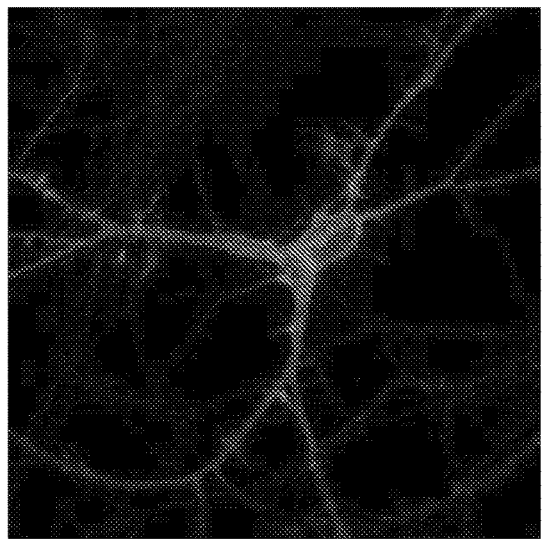
Figure 15C:
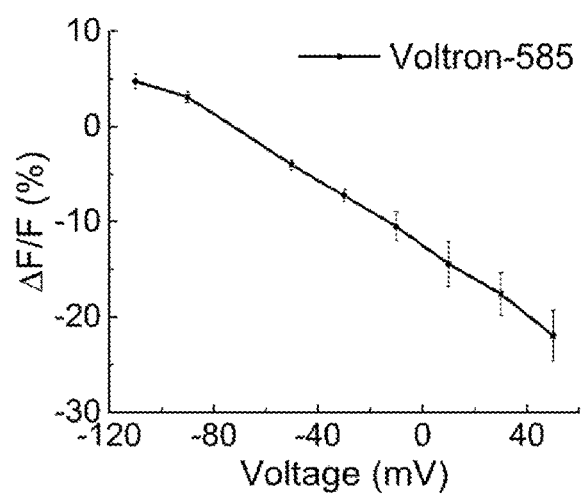
Figure 15C:
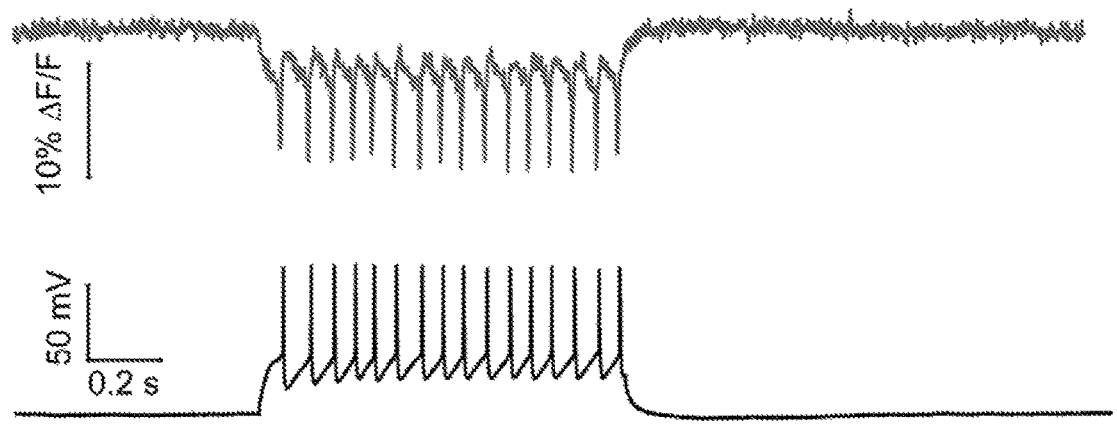
Figure 16A:
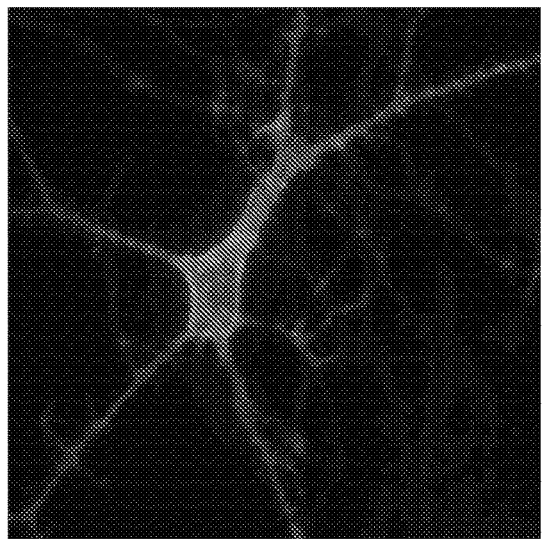
FIGS. 16A-C show graphs and images illustrating fluorescence of rat hippocampal neuron expressing Ace2N-HaloTag labeled with JF$_{635}$. (A) Fluorescence micrograph of rat hippocampal neuron in culture expressing Ace2N-HaloTag labeled with JF$_{635}$. (B) Fluorescence versus voltage for cells like in (A). (C) Fluorescence (top) compared with voltage (bottom, as measured with a whole-cell patch clamp pipette) from neurons like in (A) showing action potential spikes and subthreshold depolarizations.
Figure 16B:
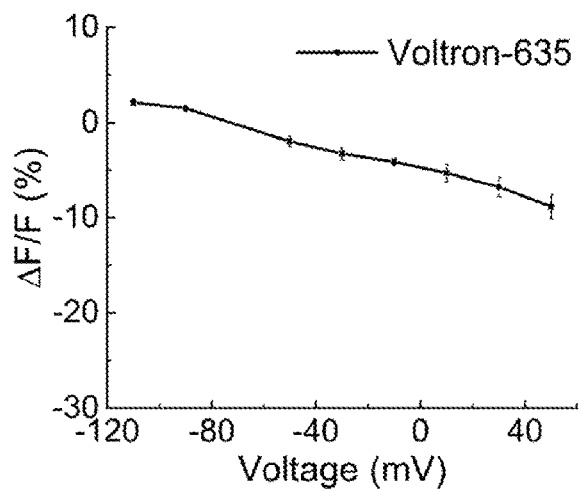
Figure 16C:
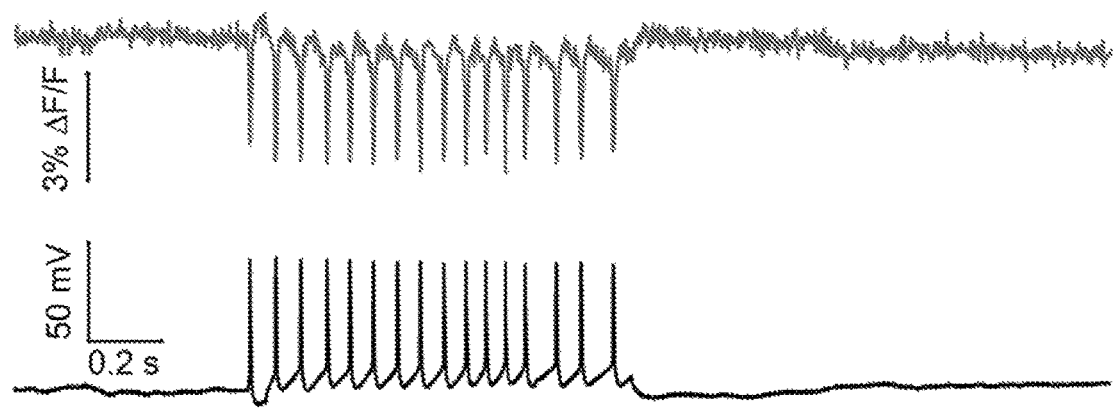

In one study, the sensors disclosed herein were used to image fluorescence voltage signals from 12 neurons simultaneously in an awake, behaving larval zebrafish for several minutes continuously. More specifically, FIGS. 10A-D show the fluorescence from neurons in zebrafish larvae expressing Ace2N-HaloTag labeled with JF$_{525}$. FIG. 11 shows fluorescence response to voltage steps of Ace2N-HaloTag labeled with JF$_{525}$ in rat hippocampal neurons in culture. FIGS. 12A-C show fluorescence of rat hippocampal neuron in culture expressing Ace2N-HaloTag labeled with JF$_{505}$ (FIG. 12A), fluorescence versus voltage (FIG. 12B), and fluorescence compared with voltage showing action potential spikes and subthreshold depolarizations (FIG. 12C). FIGS. 13A-C show fluorescence of rat hippocampal neuron in culture expressing Ace2N-HaloTag labeled with JF$_{525}$ (FIG. 13A), fluorescence versus voltage (FIG. 13B), and fluorescence compared with voltage showing action potential spikes and subthreshold depolarizations (FIG. 13C). FIGS. 14A-C show fluorescence of rat hippocampal neuron in culture expressing Ace2N-HaloTag labeled with JF$_{549}$ (FIG. 14A), fluorescence versus voltage (FIG. 14B), and fluorescence compared with voltage showing action potential spikes and subthreshold depolarizations (FIG. 14C). FIGS. 15A-C show fluorescence of rat hippocampal neuron in culture expressing Ace2N-HaloTag labeled with JF$_{585}$ (FIG. 15A), fluorescence versus voltage (FIG. 15B), and fluorescence compared with voltage showing action potential spikes and subthreshold depolarizations (FIG. 15C). FIGS. 16A-C show fluorescence of rat hippocampal neuron in culture expressing Ace2N-HaloTag labeled with JF$_{635}$ (FIG. 16A), fluorescence versus voltage (FIG. 16B), and fluorescence compared with voltage showing action potential spikes and subthreshold depolarizations (FIG. 16C).

Example 3

Figure 17A:
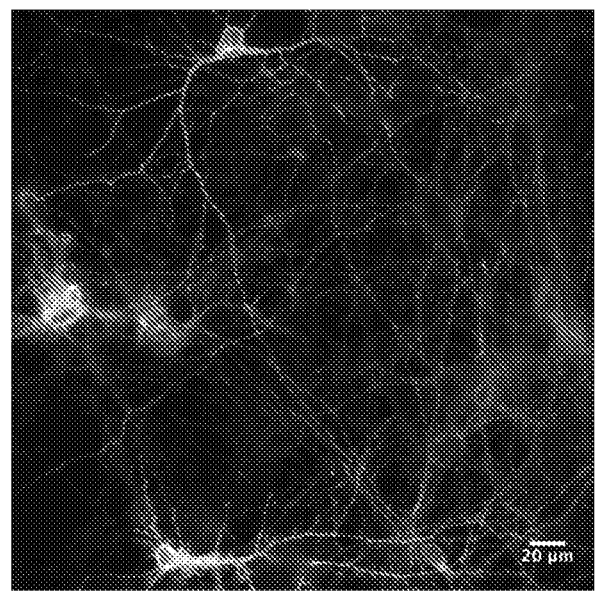
FIGS. 17A-B show graphs and images illustrating fluorescence of rat hippocampal neuron expressing CiVSD-HaloTag labeled with JF$_{635}$. (A) Fluorescence micrograph of rat hippocampal neurons in culture expressing CiVSD-HaloTag labeled with JF$_{635}$. (B) Fluorescence traces from six regions within the image from (A) showing voltage-dependent fluorescence changes resulting from spontaneous action potentials of the neurons.
Figure 17B:
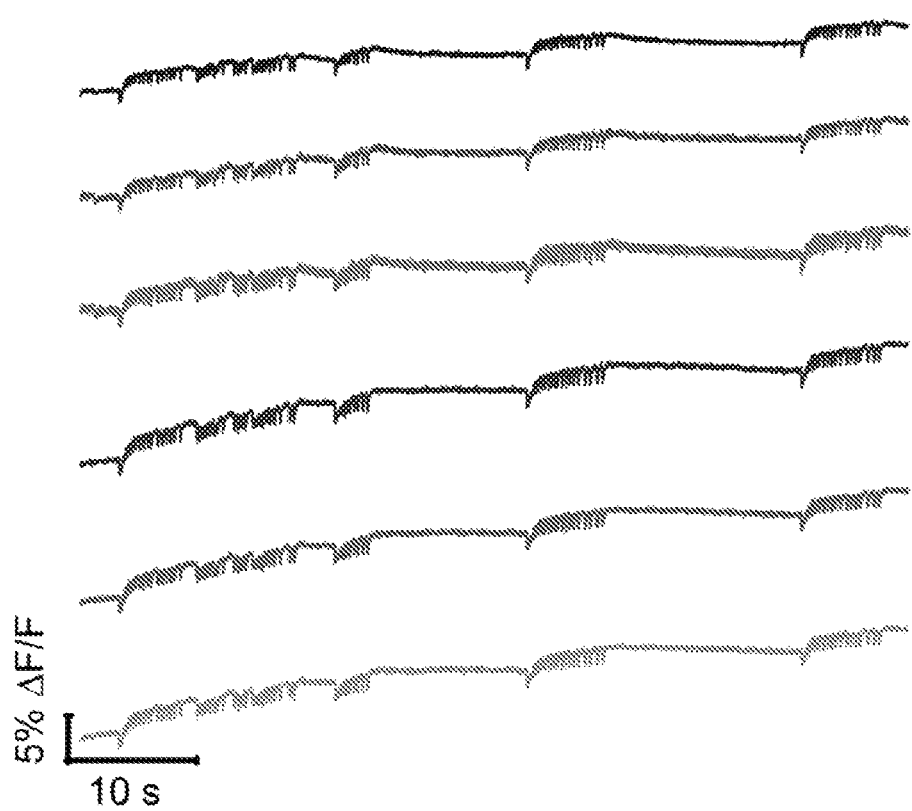
Figure 18A:
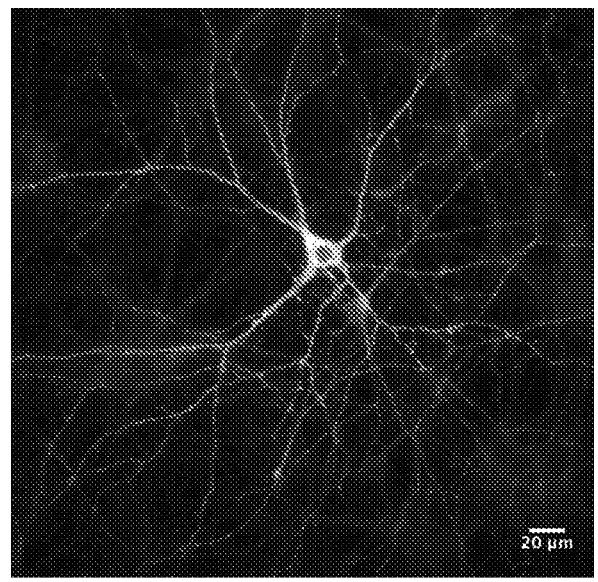
FIGS. 18A-B show graphs and images illustrating fluorescence of rat hippocampal neuron expressing CiVSD-cpHaloTag labeled with JF$_{635}$. (A) Fluorescence micrograph of rat hippocampal neurons in culture expressing CiVSD-cpHaloTag labeled with JF$_{635}$. (B) Fluorescence traces from three regions within the image from (A) showing voltage-dependent fluorescence changes resulting from spontaneous action potentials of the neurons.
Figure 18B:
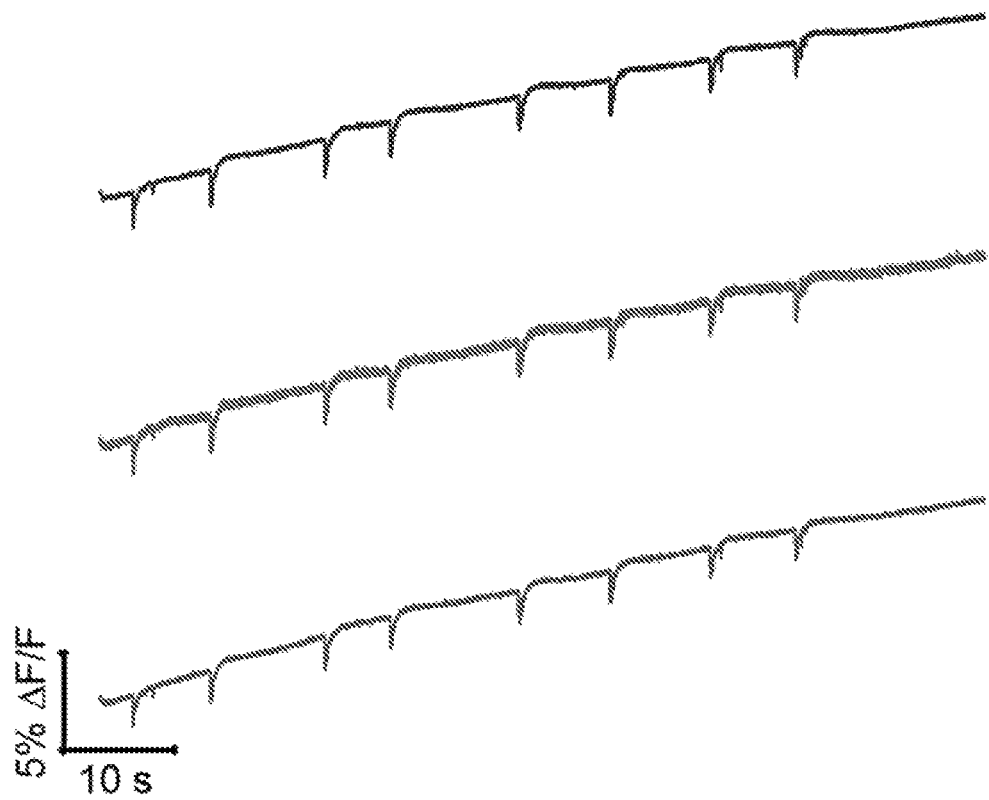
Figure 19A:
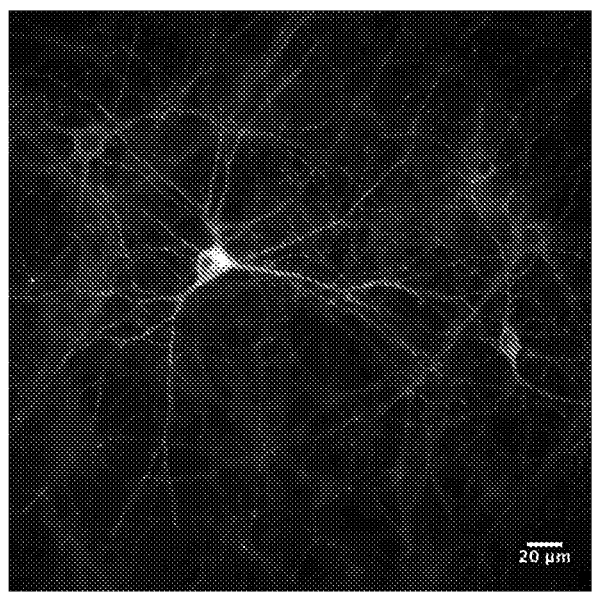
FIGS. 19A-B show graphs and images illustrating fluorescence of rat hippocampal neuron expressing DrVSD-HaloTag labeled with JF$_{635}$. (A) Fluorescence micrograph of rat hippocampal neurons in culture expressing DrVSD-HaloTag labeled with JF$_{635}$. (B) Fluorescence traces from four regions within the image from (A) showing voltage-dependent fluorescence changes resulting from spontaneous action potentials of the neurons.
Figure 19B:
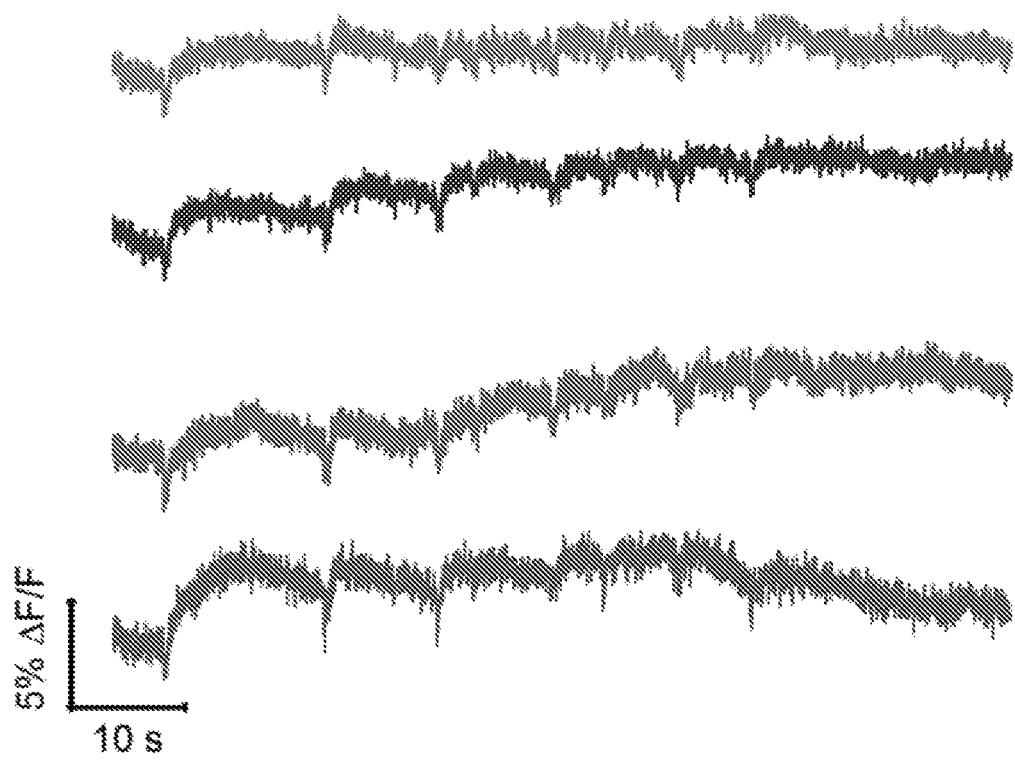
Figure 20A:
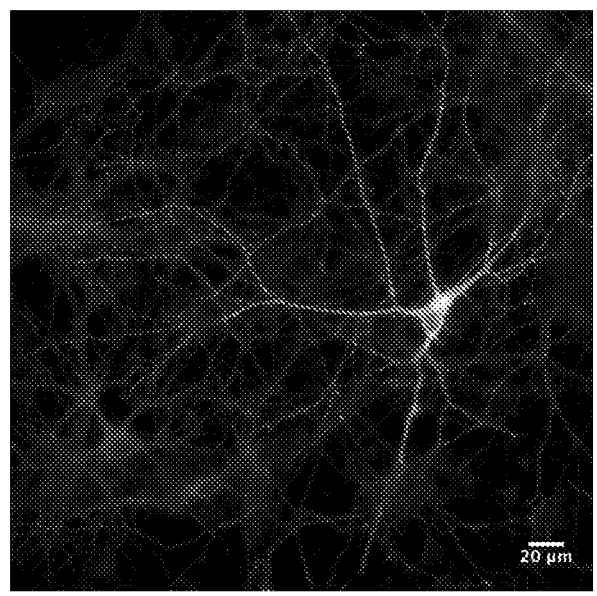
FIGS. 20A-B show graphs and images illustrating fluorescence of rat hippocampal neuron expressing GgVSD-HaloTag labeled with $JF_{635}$. (A) Fluorescence micrograph of rat hippocampal neurons in culture expressing GgVSD-HaloTag labeled with $JF_{635}$. (B) Fluorescence traces from five regions within the image from (A) showing voltage-dependent fluorescence changes resulting from spontaneous action potentials of the neurons.
Figure 20B:
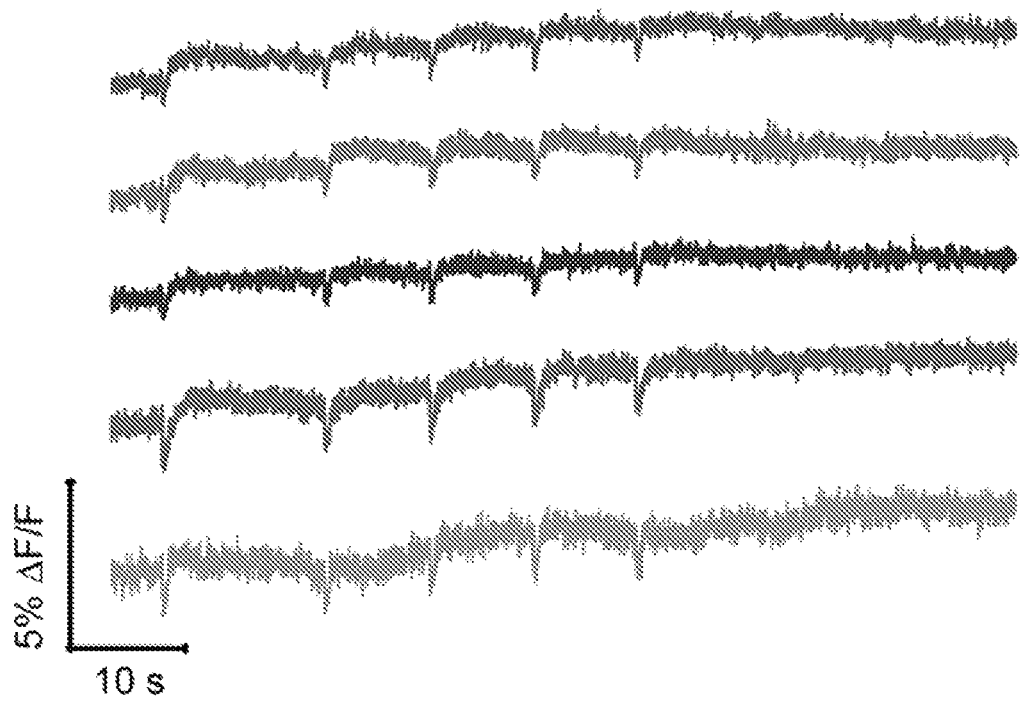

In this example, the fluorescence of JF$_{635}$ labeled HaloTag voltage indicators was measured with various different voltage sensitive proteins. More specifically, FIGS. 17A-B show the fluorescence of rat hippocampal neurons expressing CiVSD-HaloTag (SEQ ID NO: 25 and SEQ ID NO: 26) labeled with JF$_{635}$ (FIG. 17A) and voltage-dependent fluorescence changes resulting from spontaneous action potentials of the neurons (FIG. 17B). FIGS. 18A-B show the fluorescence of rat hippocampal neurons expressing CiVSD-cpHaloTag (SEQ ID NO: 27 and SEQ ID NO: 28) labeled with JF$_{635}$ (FIG. 18A) and voltage-dependent fluorescence changes resulting from spontaneous action potentials of the neurons (FIG. 18B). FIGS. 19A-B show the fluorescence of rat hippocampal neurons expressing DrVSD-HaloTag (SEQ ID NO: 29 and SEQ ID NO: 30) labeled with JF$_{635}$ (FIG. 19A) and voltage-dependent fluorescence changes resulting from spontaneous action potentials of the neurons (FIG. 19B). FIGS. 20A-B show the fluorescence of rat hippocampal neurons expressing GgVSD-HaloTag (SEQ ID NO: 31 and SEQ ID NO: 32) labeled with JF$_{635}$ (FIG. 20A) and voltage-dependent fluorescence changes resulting from spontaneous action potentials of the neurons (FIG. 20B).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Grimm, J. B. et al. A general method to fine-tune fluorophores for live-cell and in vivo imaging. *Nat. Methods* 14, 987 (2017).
2. Platisa, J., Vasan, G., Yang, A. & Pieribone, V. A. Directed Evolution of Key Residues in Fluorescent Protein Inverses the Polarity of Voltage Sensitivity in the Genetically Encoded Indicator ArcLight. *ACS Chem. Neurosci.* 8, 513-523 (2017).
3. Chamberland, S. et al. Fast two-photon imaging of subcellular voltage dynamics in neuronal tissue with genetically encoded indicators. *Elife* 6, e25690 (2017).
4. Abdelfattah, A. S. et al. A bright and fast red fluorescent protein voltage indicator that reports neuronal activity in organotypic brain slices. *J. Neurosci.* 36, 2458-2472 (2016).
5. Abdelfattah, A. S., Rancic, V., Rawal, B., Ballanyi, K. & Campbell, R. E. Ratiometric and photoconvertible fluorescent protein-based voltage indicator prototypes. *Chem. Commun.* 104, 40-50 (2016).
6. Gong, Y. et al. High-speed recording of neural spikes in awake mice and flies with a fluorescent voltage sensor. *Science (80-.).* 350, 1361-1366 (2015).
7. Grimm, J. B. et al. A general method to improve fluorophores for live-cell and single-molecule microscopy. *Nat. Methods* 12, 244-250 (2015).
8. Woodford, C. R. et al. Improved PeT molecules for optically sensing voltage in neurons. *J. Am. Chem. Soc.* 137, 1817-1824 (2015).
9. Grenier, V., Walker, A. S. & Miller, E. W. A Small-Molecule Photoactivatable Optical Sensor of Transmembrane Potential. *J. Am. Chem. Soc.* 137, 10894-10897 (2015).
10. Huang, Y. L., Walker, A. S. & Miller, E. W. A Photostable Silicon Rhodamine Platform for Optical Voltage Sensing. *J. Am. Chem. Soc.* 137, 10767-10776 (2015).
11. Zou, P. et al. Bright and fast multicoloured voltage reporters via electrochromic FRET. *Nat. Commun.* 5, 4625 (2014).
12. St-Pierre, F. et al. High-fidelity optical reporting of neuronal electrical activity with an ultrafast fluorescent voltage sensor. *Nat. Neurosci.* 17, 884-889 (2014).
13. Hochbaum, D. R. et al. All-optical electrophysiology in mammalian neurons using engineered microbial rhodopsins. *Nat. Methods* 11, 825-833 (2014).
14. Gong, Y., Wagner, M. J., Zhong Li, J. & Schnitzer, M. J. Imaging neural spiking in brain tissue using FRET-opsin protein voltage sensors. *Nat. Commun.* 5, 3674 (2014).
15. Treger, J. S., Priest, M. F., Iezzi, R. & Bezanilla, F. Real-time imaging of electrical signals with an infrared FDA-approved dye. *Biophys. J* 107, L09-L012 (2014).
16. Han, Z. et al. Fluorescent protein voltage probes derived from ArcLight that respond to membrane voltage changes with fast kinetics. *PLoS One* 8, e81295 (2013).

17. Gong, Y., Li, J. Z. & Schnitzer, M. J. Enhanced Archaerhodopsin Fluorescent Protein Voltage Indicators. *PLoS One* 8, e66959 (2013).
18. Barnett, L., Platisa, J., Popovic, M., Pieribone, V. A. & Hughes, T. A fluorescent, genetically-encoded voltage probe capable of resolving action potentials. *PLoS One* 7, e43454 (2012).
19. Akemann, W. et al. Imaging neural circuit dynamics with a voltage-sensitive fluorescent protein. *J. Neurophysiol.* 108, 2323-2337 (2012).
20. Encell, L. P. et al. Development of a dehalogenase-based protein fusion tag capable of rapid, selective and covalent attachment to customizable ligands. *Curr. Chem. Genomics* 6, 55-71 (2012).
21. Jin, L. et al. Single action potentials and subthreshold electrical events imaged in neurons with a fluorescent protein voltage probe. *Neuron* 75, 779-785 (2012).
22. Yan, P. et al. Palette of fluorinated voltage-sensitive hemicyanine dyes. *Proc. Natl. Acad. Sci.* 109, 20443-20448 (2012).
23. Miller, E. W. et al. Optically monitoring voltage in neurons by photo-induced electron transfer through molecular wires. *Proc. Natl. Acad. Sci.* 109, 2114-2119 (2012).
24. Kralj, J. M., Hochbaum, D. R., Douglass, A. D. & Cohen, A. E. Electrical spiking in *Escherichia coli* probed with a fluorescent voltage-indicating protein. *Science (80-.).* 333, 345-348 (2011).
25. Kralj, J. M., Douglass, A. D., Hochbaum, D. R., Maclaurin, D. & Cohen, A. E. Optical recording of action potentials in mammalian neurons using a microbial rhodopsin. *Nat. Methods* 9, 90-95 (2011).
26. Lebeuf, R., Férézou, I., Rossier, J., Arseniyadis, S. & Cossy, J. Straightforward synthesis of the near-Infrared fluorescent voltagesensitive dye RH1691 and analogues thereof. *Org. Lett.* 11, 4822-4825 (2009).
27. Bradley, J., Luo, R., Otis, T. S. & DiGregorio, D. A. Submillisecond Optical Reporting of Membrane Potential In Situ Using a Neuronal Tracer Dye. *J. Neurosci.* 29, 9197-9209 (2009).
28. Gautier, A. et al. An Engineered Protein Tag for Multiprotein Labeling in Living Cells. *Chem. Biol.* 15, 128-136 (2008).
29. Los, G. V. et al. HaloTag: A novel protein labeling technology for cell imaging and protein analysis. *ACS Chem. Biol.* 3, 373-382 (2008).
30. Fromherz, P., Hübener, G., Kuhn, B. & Hinner, M. J. ANNINE-6plus, a voltage-sensitive dye with good solubility, strong membrane binding and high sensitivity. *Eur. Biophys. J.* 37, 509-514 (2008).
31. Sjulson, L. & Miesenbock, G. Rational Optimization and Imaging In Vivo of a Genetically Encoded Optical Voltage Reporter. *J. Neurosci.* 28, 5582-5593 (2008).
32. Knopfel, T., Tomita, K., Shimazaki, R. & Sakai, R. Optical recordings of membrane potential using genetically targeted voltage-sensitive fluorescent proteins. *Methods* 30, 42-48 (2003).
33. Guerrero, G., Siegel, M. S., Roska, B., Loots, E. & Isacoff, E. Y. Tuning FlaSh: redesign of the dynamics, voltage range, and color of the genetically encoded optical sensor of membrane potential. *Biophys. J.* 83, 3607-3618 (2002).
34. Ataka, K. & Pieribone, V. A. A genetically targetable fluorescent probe of channel gating with rapid kinetics. *Biophys. J.* 82, 509-516 (2002).
35. Keppler, A. et al. A general method for the covalent labeling of fusion proteins with small molecules in vivo. *Nat. Biotechnol.* 21, 86-89 (2002).
37. Siegel, M. S. & Isacoff, E. Y. A genetically encoded optical probe of membrane voltage. *Neuron* 19, 735-741 (1997).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A voltage indicator comprising a membrane-localized voltage sensitive protein coupled to a capture protein, wherein the capture protein is covalently or noncovalently labeled with one or more cell permeable fluorescent dyes.

2. The voltage indicator of claim 1, where the one or more cell permeable fluorescent dyes are azetidine-containing dyes.

3. The voltage indicator of claim 2, wherein the one or more azetidine-containing dyes are selected from the group consisting of

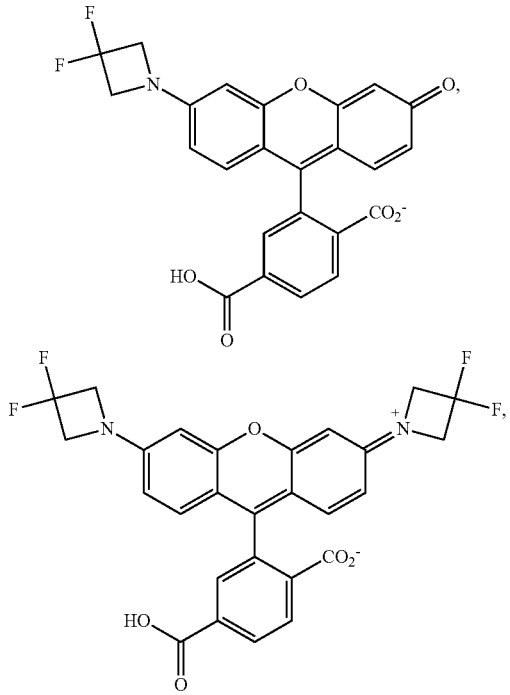

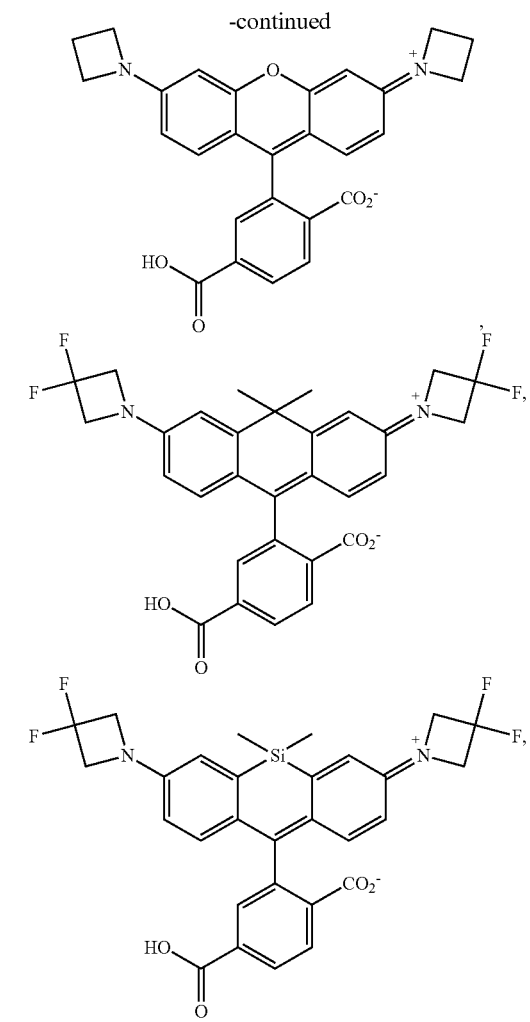

and combinations thereof.

4. The voltage indicator of claim 1, wherein the voltage sensitive protein is an opsin.

5. The voltage indicator of claim 4, wherein the opsin is a microbial opsin.

6. The voltage indicator of claim 5, wherein the microbial opsin is selected from the group consisting of QuasAr2, Ace2N, or a combination thereof.

7. The voltage indicator of claim 1, wherein the capture protein is covalently labeled by the one or more fluorescent dyes.

8. The voltage indicator of claim 7, wherein the covalent capture protein is a self-labeling protein tag.

9. The voltage indicator of claim 1, wherein the capture protein is non-covalently labeled by the one or more fluorescent dyes.

10. The voltage indicator of claim 9, where in the capture protein is biotin-avidin.

11. The voltage indicator of claim 1, wherein the membrane-localized voltage sensitive protein comprises at least one voltage sensitive domain selected from the group consisting of an opsin, *Ciona intestinalis* voltage-sensing domain (CiVSD), *Dario rerio* voltage-sensing domain (DrVSD), *Gallus* voltage-sensing domain (GgVSD), and a combination thereof.

12. A method of measuring voltage, the method comprising administering one or more cell permeable fluorescent dyes and a voltage indicator comprising a membrane-localized voltage sensitive protein coupled to a capture protein and determining measuring changes in fluorescence when the one or more cell permeable fluorescent dye are captured by the covalent-capture protein of the voltage.

13. The method of claim 12, wherein changes in fluorescence are observed with a microscope.

14. The method of claim 12, wherein the voltage indicator further comprises a linker between the voltage-sensitive protein and the capture protein.

15. The method of claim 14, further comprising modifying a length of the linker.

16. The method of claim 15, wherein modifying the length of the linker comprises removing at least one amino acid residue.

17. The method of claim 16, wherein removing at least one amino acid residue comprises removing between 1 and 22 amino acid residues.

18. The method of claim 15, wherein modifying the length of the linker modifies the size of a fluorescence response.

19. The method of claim 12, further comprising measuring changes in voltage based upon changes in fluorescence.

20. The method of claim 12, wherein the membrane-localized voltage sensitive protein comprises at least one voltage sensitive domain selected from the group consisting of an opsin, *Ciona intestinalis* voltage-sensing domain (CiVSD), *Dario rerio* voltage-sensing domain (DrVSD), *Gallus* voltage-sensing domain (GgVSD), and a combination thereof.

* * * * *

UNITED STATES PATENT AND TRADEMARK OFFICE
CERTIFICATE OF CORRECTION

PATENT NO. : 11,385,236 B2
APPLICATION NO. : 16/347765
DATED : July 12, 2022
INVENTOR(S) : Eric R. Schreiter, Luke D. Lavis and Ahmed Abdelfattah It is certified that error appears in the above-identified patent and that said Letters Patent is hereby corrected as shown below:

In the Claims

Claim 12, Column 88, Line 1, delete "determining"

Claim 12, Column 88, Line 2, replace "dye" with "dyes"

Claim 12, Column 88, Line 3, replace "voltage" with "voltage indicator"

Signed and Sealed this
Thirtieth Day of August, 2022

Katherine Kelly Vidal
*Director of the United States Patent and Trademark Office*